United States Patent
Drmanac et al.

(10) Patent No.: US 12,071,659 B2
(45) Date of Patent: *Aug. 27, 2024

(54) MULTIPLE TAGGING OF LONG DNA FRAGMENTS

(71) Applicant: Complete Genomics, Inc., San Jose, CA (US)

(72) Inventors: Radoje Drmanac, Los Altos Hills, CA (US); Brock A. Peters, San Francisco, CA (US); Andrei Alexeev, Woodland, CA (US)

(73) Assignee: Complete Genomics, Inc., San Jose, CA (US)

( * ) Notice: Subject to any disclaimer, the term of this patent is extended or adjusted under 35 U.S.C. 154(b) by 38 days.

This patent is subject to a terminal disclaimer.

(21) Appl. No.: 15/936,123

(22) Filed: Mar. 26, 2018

(65) Prior Publication Data

US 2019/0002969 A1  Jan. 3, 2019

Related U.S. Application Data

(63) Continuation of application No. 14/782,307, filed as application No. PCT/US2014/030649 on Mar. 17, 2014, now Pat. No. 10,557,166, which is a continuation-in-part of application No. 14/205,145, filed on Mar. 11, 2014, now Pat. No. 9,328,382.

(60) Provisional application No. 61/801,052, filed on Mar. 15, 2013.

(51) Int. Cl.
*C12Q 1/6869* (2018.01)
*C12N 15/10* (2006.01)
*C12Q 1/6806* (2018.01)

(52) U.S. Cl.
CPC ......... *C12Q 1/6869* (2013.01); *C12Q 1/6806* (2013.01); *C12N 15/1065* (2013.01); *C12Q 2525/204* (2013.01)

(58) Field of Classification Search
CPC .................................................. C12N 15/1065
See application file for complete search history.

(56) References Cited

U.S. PATENT DOCUMENTS

| | | |
|---|---|---|
| 6,451,996 B1 | 9/2002 | Drmanac et al. |
| 6,593,113 B1 | 7/2003 | Tenkanen et al. |
| 7,371,851 B1 | 5/2008 | Lexow |
| 7,897,344 B2 | 3/2011 | Dahl et al. |
| 7,901,890 B2 | 3/2011 | Dahl et al. |
| 7,910,354 B2 | 3/2011 | Drmanac et al. |
| 8,034,566 B2 | 10/2011 | Drmanac et al. |
| 8,278,039 B2 | 10/2012 | Drmanac |
| 8,445,197 B2 | 5/2013 | Drmanac et al. |
| 8,518,640 B2 | 8/2013 | Drmanac et al. |
| 8,551,702 B2 | 10/2013 | Drmanac et al. |
| 8,592,150 B2 | 11/2013 | Drmanac et al. |
| 8,609,335 B2 | 12/2013 | Drmanac et al. |
| 8,615,365 B2 | 12/2013 | Halpern et al. |
| 8,658,368 B2 | 2/2014 | Quake et al. |
| 8,673,562 B2 | 3/2014 | Drmanac |
| 8,722,326 B2 | 5/2014 | Drmanac et al. |
| 8,765,382 B2 | 7/2014 | Drmanac |
| 8,785,127 B2 | 7/2014 | Drmanac |
| 9,040,256 B2 | 5/2015 | Grunenwald et al. |
| 9,328,382 B2 | 5/2016 | Drmanac et al. |
| 9,683,230 B2* | 6/2017 | Gormley ............. C12Q 1/6834 |
| 10,023,910 B2* | 7/2018 | Drmanac ............. C12Q 1/6869 |
| 10,557,166 B2* | 2/2020 | Drmanac ............. C12Q 1/6806 |
| 2003/0040620 A1* | 2/2003 | Langmore ............. C12Q 1/6844 536/24.3 |
| 2007/0072208 A1 | 3/2007 | Drmanac |
| 2007/0269817 A1 | 11/2007 | Shapero |
| 2008/0242560 A1 | 10/2008 | Gunderson et al. |
| 2009/0176652 A1 | 7/2009 | Dahl et al. |
| 2009/0203551 A1 | 8/2009 | Dahl et al. |
| 2009/0233814 A1* | 9/2009 | Bashkirov ............. C12Q 1/6806 536/25.41 |
| 2009/0270273 A1 | 10/2009 | Burns et al. |
| 2009/0311691 A1 | 12/2009 | Drmanac |
| 2010/0028888 A1 | 2/2010 | Smith et al. |
| 2010/0069263 A1 | 3/2010 | Shendure et al. |
| 2010/0105052 A1 | 4/2010 | Drmanac et al. |
| 2010/0143908 A1 | 6/2010 | Glllevet |
| 2010/0298170 A1 | 11/2010 | Heredia et al. |
| 2011/0014623 A1 | 1/2011 | Becker et al. |
| 2012/0003657 A1 | 1/2012 | Myllykangas et al. |
| 2012/0100534 A1 | 4/2012 | Drmanac et al. |

(Continued)

FOREIGN PATENT DOCUMENTS

| | | |
|---|---|---|
| CA | 3128098 A1 | 8/2020 |
| CN | 1193357 A | 9/1998 |

(Continued)

OTHER PUBLICATIONS

Barbee et al. (2008) Magnetic Assembly of High-Density DNA Arrays for Genomic Analyses. Analytical Chemistry, 80:2149-2154) (Year: 2008).*
Dunne et al., Next-generation and whole-genome sequencing in the diagnostic clinical microbiology laboratory. Eur J Microbiol Infect Dis (2012), 31: 1719-1726, published Jun. 8, 2012 (Year: 2012).*
Levy et al., The Diploid Genome Sequence of an Individual Human. PLOS Biology (2007), 5(10): 2113-2144 (Year: 2007).*

(Continued)

*Primary Examiner* — Celine X Qian
*Assistant Examiner* — Catherine Konopka
(74) *Attorney, Agent, or Firm* — Kilpatrick Townsend & Stockton LLP

(57) ABSTRACT

The present invention provides methods and compositions for tagging long fragments of a target nucleic acid for sequencing and analyzing the resulting sequence information in order to reduce errors and perform haplotype phasing, for example.

24 Claims, 21 Drawing Sheets
Specification includes a Sequence Listing.

(56) References Cited

U.S. PATENT DOCUMENTS

| | | |
|---|---|---|
| 2012/0157322 A1 | 6/2012 | Myllykangas et al. |
| 2012/0165202 A1 | 6/2012 | Porreca et al. |
| 2012/0208705 A1 | 8/2012 | Steemers et al. |
| 2012/0208724 A1 | 8/2012 | Steemers et al. |
| 2012/0258892 A1 | 10/2012 | Wang |
| 2012/0301925 A1 | 11/2012 | Belyaev |
| 2012/0301926 A1* | 11/2012 | Chen ............... C12P 19/40 536/23.1 |
| 2013/0124100 A1 | 5/2013 | Drmanac et al. |
| 2013/0281305 A1 | 10/2013 | Peck et al. |
| 2014/0051588 A9 | 2/2014 | Drmanac et al. |
| 2014/0152793 A1 | 6/2014 | Staker et al. |
| 2014/0323316 A1 | 10/2014 | Drmanac et al. |
| 2015/0368638 A1 | 12/2015 | Steemers et al. |
| 2016/0046985 A1 | 2/2016 | Drmanac et al. |
| 2016/0376647 A1 | 12/2016 | Travers et al. |
| 2017/0022554 A1 | 1/2017 | Drmanac et al. |
| 2018/0044667 A1 | 2/2018 | Geng |
| 2018/0044668 A1 | 2/2018 | Jiang et al. |
| 2019/0002970 A1 | 1/2019 | Drmanac et al. |

FOREIGN PATENT DOCUMENTS

| | | | |
|---|---|---|---|
| CN | 101278058 A | 10/2008 | |
| CN | 101432439 A | 5/2009 | |
| CN | 102084001 A | 6/2011 | |
| CN | 105593683 A | 5/2016 | |
| CN | 106795651 A | 5/2017 | |
| CN | 107686842 A | 2/2018 | |
| HK | 1218412 A1 | 2/2017 | |
| WO | 95/23875 A1 | 9/1995 | |
| WO | 2010/048605 A1 | 4/2010 | |
| WO | 2012025250 A1 | 3/2012 | |
| WO | WO-2012061832 A1 * | 5/2012 | ......... C12N 15/1065 |
| WO | 2012/106546 A2 | 8/2012 | |
| WO | 2012/166425 A2 | 12/2012 | |
| WO | 2014/108810 A2 | 7/2014 | |
| WO | 2015051006 | 4/2015 | |
| WO | 2015085274 A1 | 6/2015 | |
| WO | 2016058517 A1 | 4/2016 | |
| WO | 2016061517 A2 | 4/2016 | |
| WO | 2016109604 A2 | 7/2016 | |
| WO | 2017151828 A1 | 9/2017 | |
| WO | 2018118971 A1 | 6/2018 | |
| WO | 2019217452 A1 | 11/2019 | |

OTHER PUBLICATIONS

Levin and Moran. Dynamic interactions between transposable elements and their hosts. Nature Reviews Genetics (2011) 12: 615-627 (Year: 2011).*

Adey et al., "In vitro, long-range sequence information for de novo genome assembly via transposase contiguity", Genome Res., vol. 24, Oct. 2014, pp. 2041-2049.

Adey et al., "The haplotype-resolved genome and epigenome of the aneuploid He La cancer cell line", Nature, vol. 500, Aug. 2013, pp. 207-211.

Adey et al., Rapid, low-input, low-bias construction of shotgun fragment libraries by high-density in vitro transposition, Genome Biology, Biomed Central Ltd.XP021091768, Dec. 8, 2010, pp. 1-17.

Amini et al., Haplotype-resolved whole-genome sequencing by contiguitypreserving transposition and combinatorial indexing, Nature Genetics, vol. 46, No. 12, Oct. 19, 2014, pp. 1343-1349.

U.S. Appl. No. 61/623,676, filed Apr. 13, 2012 entitled, "Identification of DNA Fragments and Structural Variations".

Ason et al., "DNA sequence bias during Tn5 transposition", J. Mol. Biol., vol. 335, Jan. 2004, pp. 1213-1225.

Barbee, K. et al. Magnetic Assembly of High-Density DNA Arrays for Genomic Analyses. Anal. Chem, vol. 80. Published Mar. 2008. pp. 2149-2154.

Bansal et al., An MCMC algorithm for haplotype assembly from whole-genome sequence data, Genome Research, 18: 2008, 1336-1346.

Bansal et al., "The next phase in human genetics", Nat. Biotechnol., vol. 29, Jan. 2011, pp. 38-39.

Bentley et al., "Accurate Whole Human Genome Sequencing Using Reversible Terminator Chemistry", Nature, vol. 456, No. 7218, Nov. 6, 2008, pp. 53-59.

Browning et al., "Haplotype phasing: existing methods and new developments", Nature Reviews Genetics, vol. 12, Sep. 2011, pp. 703-714.

Bryne et al., "JASPAR, the open access database of transcription factor-binding profiles: new content and tools in the 2008 update", Nucleic Acids Research; vol. 36: 2008, pp. D102-D106.

Burton et al., "Chromosome-scale scaffolding of de novo genome assemblies based on chromatin interactions", Nat. Biotechnol., vol. 31, Dec. 2013, pp. 1119-1125.

Cao et al., "De novo assembly of a haplotype resolved human genome", Nat. Biotechnol., vol. 33, May 2015, pp. 617-622.

Cusanovich et al., "Multiplex single cell profiling of chromatin accessibility by combinatorial cellular indexing", Science, vol. 348, May 2015, pp. 910-914.

Dear et al., "Happy mapping: a proposal for linkage mapping the human genome", Nucleic Acids Res., vol. 17, Sep. 1989, pp. 6795-6807.

Drmanac R. et al., "Human genome sequencing using unchained base reads on self-assembling DNA nanoarrays". Science; 327(5961): 2010, pp. 78-81.

European Application No. EP14764477.7, Extended European Search Report dated Nov. 17, 2016, 11 pages.

Fan et al., "Whole-Genome Molecular Haplotyping of Single Cells", Nature Biotechnology, vol. 29, No. 1, Jan. 2011, pp. 51-57.

Feuk, "Structural variation in the human genome", Nat. Rev. Genet., vol. 7, Feb. 2006, pp. 85-97.

Furka et al., "General method for rapid synthesis of multicomponent peptide mixtures", Int. J. Pept. Protein Res., vol. 37, Jun. 1991, pp. 487-493.

Goodwin et al., "Oxford Nanopore Sequencing and de novo assembly of a eukaryotic genome", Preprint at bioRxiv http,;:i/doi.org/10.1101/01.3490, Jan. 2015, 15 pages.

International Search Report and Written Opinion dated Oct. 7, 2014 for PCT Patent Application No. PCT/US14/30649, 26 pages.

Kaper et al., "Whole-genome haplotyping by dilution, amplification and sequencing", Proc. Natl. Acad. Sci. USA, vol. 110, Apr. 2013, pp. 5552-5557.

Kitzman et al., "Haplotype-Resolved Genome Sequencing of a Gujarati Indian Individual", Nature Biotechnology vol. 29, No. 1, Dec. 19, 2011, pp. 59-64.

Kremsky et al., "Immobilization of DNA via oligonucleotides containing an aldehyde or carboxylic acid group at the 5' terminus", Nucleic Acids Res., vol. 15, Apr. 1987, pp. 2891-2909.

Kuleshov et al., "Whole-genome haplotyping using long reads and statistical methods", Nat. Biotechnol., vol. 32, Sep. 2014, pp. 261-266.

Lander et al., "Initial sequencing and analysis of the human genome", Nature, vol. 409, No. 6822, Feb. 2001, pp. 860-921.

Lebl et al., "Automatic oligonucleotide synthesizer utilizing the concept of parallel processing", Collect. Symp. Ser., vol. 12, Jun. 2011, pp. 264-267.

Levy et al., "The diploid genome sequence of an individual human", PLoS Biol., vol. 5, Sep. 2007, pp. 2113-2144.

Li et al., "The Sequence Alignment/Map format and SAM tools", Bioinformatics, vol. 25, No. 16, Jun. 8, 2009, pp. 2078-2079.

Loman et al., "A complete bacterial genome assembled de novo using only nanopore sequencing data", Nat. Methods, vol. 12, Jun. 2015, pp. 733-735.

Medvedev et al., "Computational Methods for Discovering Structural Variation with Next Generation Sequencing", Nature Methods, vol. 6, No. 11, Nov. 2009, pp. S13-S20.

Moncunill et al., "Comprehensive characterization of complex structural variations in cancer by directly comparing genome sequence reads", Nat. Biotechnol., vol. 32, Nov. 2014, pp. 1106-1112.

Nalls et al., "Large-scale meta-analysis of genome-wide association data identifies six new risk loci for Parkinson's disease", Nat. Genet., vol. 46, Sep. 2014, pp. 989-993.

(56) References Cited

OTHER PUBLICATIONS

Pendleton et al., "Assembly and diploid architecture of an individual human genome via single-molecule technologies", Nat. Methods, vol. 12, Jun. 2015, pp. 780-786.
Peters et al., "Co•barcoded sequence reads from long DNA fragments: a cost-effective solution for "perfect genome" sequencing", Front. Genet., vol. 5, Jan. 2015, 8 pages.
Peters et al., "Detection and phasing of single base de novo mutations in biopsies from human in vitro fertilized embryos by advanced whole-genome sequencing", Genome Res., vol. 25, Feb. 2015, pp. 426-434.
Peters et al., "Accurate whole genome sequencing and haplotyping from 10-20 human cells", Nature; 487(7406): 2012, pp. 190-195.
Raczy et al., "Isaac: ultra-fast whole-genome secondary analysis on Illumina sequencing platforms", Bioinformatics, vol. 29, Jun. 2013, pp. 2041-2043.
Ripke et al., "Genome-wide association analysis identifies 13 new risk loci for schizophrenia", Nat. Genet., vol. 45, Aug. 2013, pp. 1150-1159.
Sandelin et al., "JASPAR: an open-access database for eukaryotic transcription factor binding profiles", Nucleic Acids Research, vol. 32: 2004, pp. D91-D94.
Schwartz et al., Capturing native long-range contiguity by in situ library construction and optical sequencing, proceedings of the national academy of sciences, vol. 109. No. 46 XP055139553, Nov. 13, 2012, pp. 18749-18754.
Snyder et al., "Haplotype-resolved genome sequencing: experimental methods and applications", Nat. Rev. Genet., vol. 16, No. 6, Jun. 2015, pp. 344-358.
Steemers et al., "Whole-genome genotyping with the single-base extension assay", Nat. Methods, vol. 3, Jan. 2006, pp. 31-33.
Steinberg et al., "Strategies for covalent attachment of DNA to beads", Biopolymers, vol. 73, Apr. 2004, pp. 597-605.
Tarasov et al., "Fast processing of NGS alignment formats", Bioinformatics, vol. 31, Feb. 2015, pp. 2032-2034.
Venter et al., "The Sequence of the Human Genome", Science, vol. 291, Feb. 16, 2001, pp. 1304-1351.
Xie et al., "A fast and accurate algorithm for single individual haplotyping", BMC Syst. Bioi., vol. 6, Suppl. 2, Dec. 2012, 10 pages.
Zong et al., "Genome-wide detection of single nucleotide and copy-number variations of a single human cell", Science, vol. 338, Dec. 2012, pp. 1622-1626.
Chen et al., Tagmentation on Microbeads: Restore Long-Range DNA Sequence Information Using Next Generation Sequencing with Library Prepared by Surface-Immobilized Transposomes, ACS Appl. Mater Interfaces, vol. 10, No. 14, Mar. 15, 2018, pp. 11539-11545.
International Application No. PCT/IB2020/050715, International Search Report and Written Opinion dated Jul. 10, 2020, 11 pages.
International Application No. PCT/US2019/031161, International Search Report and Written Opinion dated Oct. 1, 2019, 14 pages.
U.S. Appl. No. 14/205,145, Non-Final Office Action mailed on Jun. 4, 2015, 11 pages.
U.S. Appl. No. 14/205,145, Notice of Allowance mailed on Mar. 14, 2016, 5 pages.
U.S. Appl. No. 14/782,307, Advisory Action mailed on Feb. 12, 2018, 3 pages.
U.S. Appl. No. 14/782,307, Corrected Notice of Allowance mailed on Apr. 27, 2018, 3 pages.
U.S. Appl. No. 14/782,307, Final Office Action mailed on Jul. 19, 2017, 9 pages.
U.S. Appl. No. 14/782,307, Non-Final Office Action mailed on Oct. 31, 2016, 18 pages.
U.S. Appl. No. 14/782,307, Non-Final Office Action mailed on Dec. 18, 2018, 20 pages.
U.S. Appl. No. 14/782,307, Notice of Allowance mailed on Mar. 20, 2018, 8 pages.
U.S. Appl. No. 14/782,307, Notice of Allowance mailed on Sep. 25, 2019, 9 pages.
U.S. Appl. No. 15/136,780, Non-Final Office Action mailed on Jun. 21, 2017, 11 pages.
U.S. Appl. No. 15/136,780, Notice of Allowance mailed on Apr. 20, 2018, 7 pages.
U.S. Appl. No. 15/136,780, Supplemental Notice of Allowance mailed on Jun. 13, 2018, 2 pages.
U.S. Appl. No. 15/993,418, Non-Final Office Action mailed on Dec. 15, 2021, 28 pages.
U.S. Appl. No. 61/750,682, Sample Preparation on a Solid Support mailed on Jan. 9, 2013, 79 pages.
Communication from European Patent Office concerning Application No. 14764477.7, mailed Nov. 17, 2016, 11 pages.
Communication pursuant to Art. 94(3) EPC from European Patent Office concerning Application No. 14764477.7, mailed Mar. 29, 2018, 6 pages.
Communication pursuant to Art. 94(3) EPC from European Patent Office concerning Application No. 14764477.7, mailed Mar. 18, 2019, 5 pages.
International Preliminary Report on Patentability and Written Opinion of the International Search Authority for PCT/US2014/030649 Mailed Oct. 7, 2014, 21 pages.
Berensmeier, Magnetic Particles for the Separation and Purification of Nucleic Acids, Applied Microbiology and Biotechnology, vol. 73, 2006, pp. 495-504.
Brenner et al., In Vitro Cloning of Complex Mixtures of DNA on Microbeads: Physical Separation of Differentially Expressed cDNAs, PNAS, vol. 97, No. 4, 2000, pp. 1665-1670.
Bronner et al., Improved Protocols for Illumina Sequencing, Current Protocols in Human Genetics, Jul. 2009, pp. 1-46.
Chen et al., Tagmentation on Microbeads: Restore Long-Range DNA Sequence Information Using Next Generation Sequencing with Library Prepared by Surface-Immobilized Transposomes, ACS Appl. Mater Interfaces, vol. 10, No. 14, Mar. 15, 2018, p. 11539-11545.
Chen et al., Ultralow-Input Single-Tube Linked-Read Library Method Enables Short-read Second-generation Sequencing Systems to Routinely Generate Highly Accurate and Economical Long-range Sequencing Information, Genome Research, vol. 30, Available Online at: https://genome.cshlp.org/content/30/6/898.short, 2020, pp. 898-909.
Dressman et al., Transforming Single DNA Molecules into Fluorescent Magnetic Particles for Detection and Enumeration of Genetic Variations, Proceedings of the National Academy of Sciences of the United States of America, vol. 100, No. 15, Jul. 22, 2003, pp. 8817-8822.
European Application No. 14764477.7, Notice of Opposition mailed on Jan. 27, 2021, 44 pages.
Jo et al., Elongation and Migration of Single DNA Molecules in Microchannels Using Oscillatory Shear Flows, Lab on a Chip, vol. 9, 2009, pp. 2348-2355.
International Application No. PCT/IB2020/050715, International Search Report and Written Opinion mailed on Jul. 10, 2020, 11 pages.
International Application No. PCT/US2019/031161, International Search Report and Written Opinion mailed on Oct. 1, 2019, 14 pages.
Radler et al., Structure of DNA-Cationic Liposome Complexes: DNA Intercalation in Multilamellar Membranes in Distinct Interhelical Packing Regimes, Science, vol. 275, No. 5301, Feb. 7, 1997, pp. 810-814.
Reznikoff, Tn5 as a Model for Understanding DNA Transposition, Molecular Microbiology, vol. 47, No. 5, 2003, pp. 1199-1206.
Shendure et al., Accurate Multiplex Polony Sequencing of an Evolved Bacterial Genome, Science, vol. 309, No. 5741, Sep. 9, 2005, pp. 1728-1732.
Wang et al., 3' Branch Ligation: A Novel Method to Ligate Non-complementary DNA to Recessed or Internal 3'OH Ends in DNA or RNA, DNA Research, vol. 26, No. 1, 2019, pp. 45-53.
Wang et al., Efficient and Unique Cobarcoding Of Second-Generation Sequencing Reads from Long DNA Molecules Enabling Cost-effective and Accurate Sequencing, Haplotyping, And De Novo Assembly, Genome Research, vol. 29, No. 5, Apr. 2, 2019, pp. 798-808.

(56) References Cited

OTHER PUBLICATIONS

Wang et al., Single Tube Bead-Based DNA Co-Barcoding for Cost Effective and Accurate Sequencing, Haplotyping, And Assembly, bioRxiv, Available online at https://doi.org/10.1101/324392, May 17, 2018, 17 pages.

Zhang et al., Haplotype Phasing of Whole Human Genomes Using Bead-Based Barcode Partitioning in a Single Tube, Nature Biotechnology, vol. 35, No. 9, Sep. 2017, pp. 852-857.

Zheng et al., Haplotyping Gemnline and Cancer Genomes Using High-Throughput Linked-Read Sequencing, Nature Biotechnology, vol. 34, No. 3, 2016, 13 pages.

Zinchenko et al., Single-Chain Compaction of Long Duplex DNA by Cationic Nanoparticles: Modes of Interaction and Comparison with Chromatin, The Journal of Physical Chemistry B, vol. 111, 2007, pp. 3019-3031.

EP14764477.7 Communication of Notices of Opposition, 1 page, Feb. 3, 2021.

European Patent No. EP 2 969 847, Patentee's Response to Opposition, Jun. 11, 2021, 54 pages.

European Application No. 20749055.8, Partial Supplementary European Search Report mailed on Sep. 19, 2022, 12 pages.

Johne et al., Rolling-Circle Amplification of Viral DNA Genomes using Phi29 Polymerase, Trends in Microbiology, vol. 17, No. 5, May 2009, pp. 205-211.

Lou et al., High-Throughput DNA Sequencing Errors are Reduced by Orders of Magnitude Using Circle Sequencing, Proceedings of the National Academy of Sciences, vol. 110, No. 49, Dec. 3, 2013, p. 19872 - 19877.

Salk et al., Enhancing the Accuracy of Next-Generation Sequencing for Detecting Rare and Subclonal Mutations, Nature Reviews Genetics, vol. 19, No. 5, Mar. 2018, pp. 269-285.

Schmitt et al., Risks of Double-Counting in Deep Sequencing, Proceedings of the National Academy of Sciences of the United States of America, vol. 111, No. 16, Apr. 22, 2014, 1 page.

Zhang et al., Haplotype Phasing of Whole Human Genomes Using Bead-based Barcode Partitioning in a Single Tube, Nature Biotechnology, vol. 35, No. 9, Jun. 26, 2017, 9 pages.

European Application No. 19799951.9, Extended European Search Report mailed on Nov. 30, 2021, 5 pages.

European Application No. 20170317.0, Extended European Search Report mailed on Oct. 6, 2020, 9 pages.

European Application No. 20749055.8, Extended European Search Report mailed on Dec. 21, 2022, 12 pages.

European Application No. 14764477.7, Summons to Attend Oral Proceedings mailed on Feb. 7, 2023, 70 pages.

Lamble et al., Improved Workflows for High Throughput Library Preparation Using the Transposome-based Nextera System, BMC Biotechnology, vol. 13, No. 104, Nov. 20, 2013, pp. 1-10.

Application No. EP23168214.7, Extended European Search Report, Mailed on Sep. 12, 2023, 6 pages.

\* cited by examiner

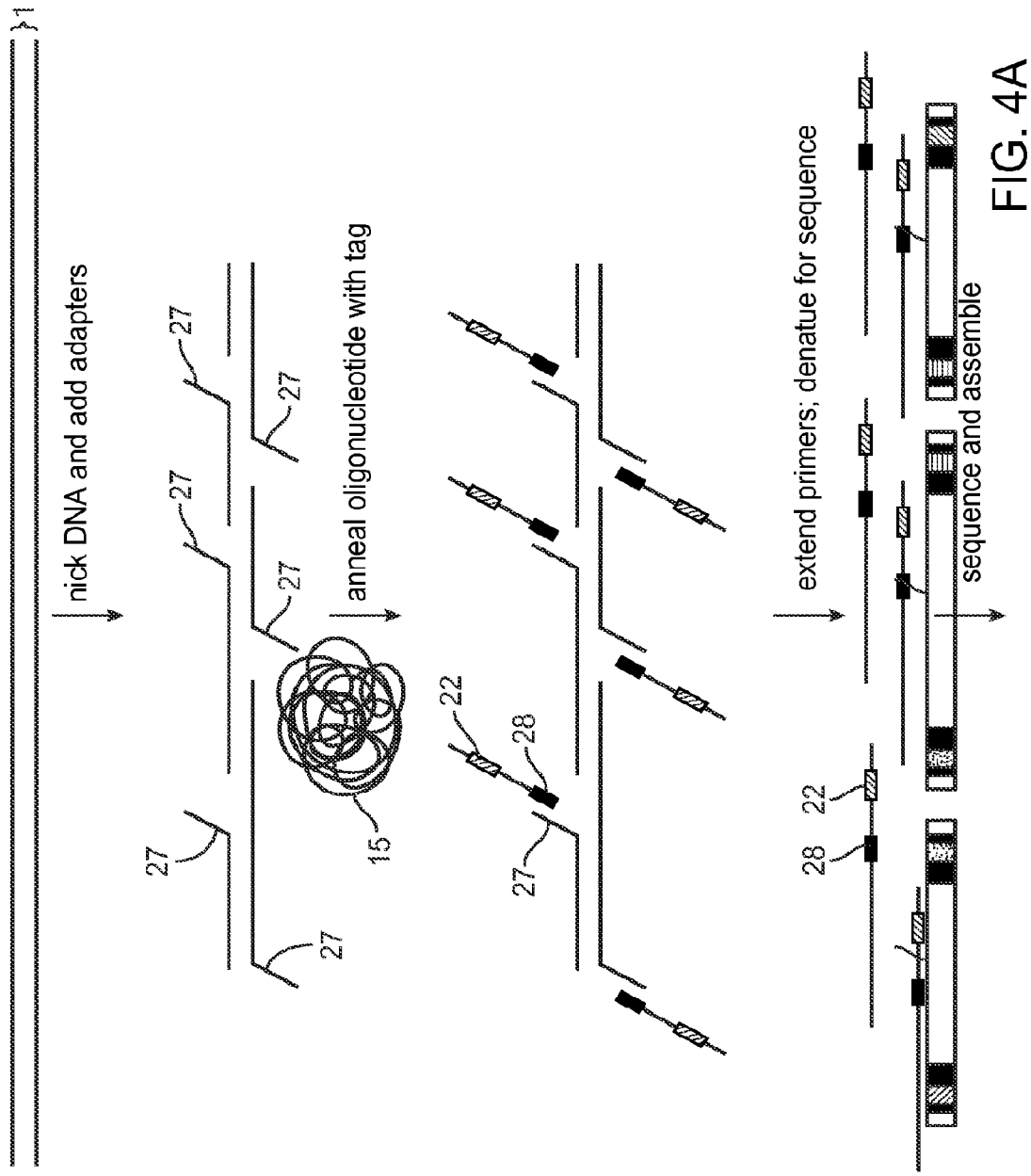

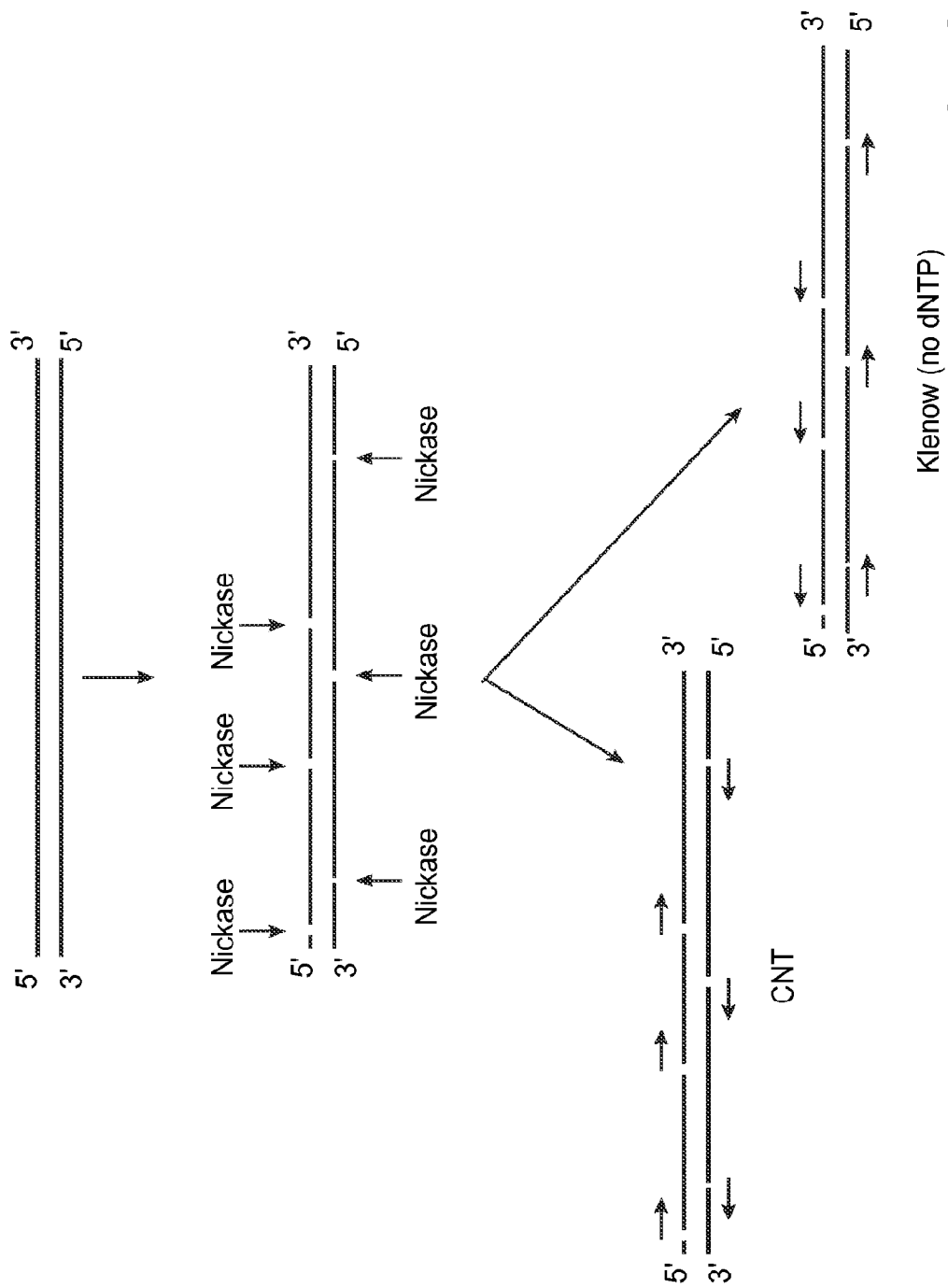

| | |
|---|---|
| Graph Construction via LFR | • Make a graph of all the het pairs that are within the expected distance. |
| Graph Construction via Mate Pairs | • Optionally, populate the graph of all the het pairs that are within the expected distance using mate pair data. |
| Graph Combination | • Combine the LFR-generated and Mate-pair generated graphs. |
| Graph Trimming | • Optionally, trim the graph using heuristics. |
| Graph Optimization | • Optimize the graph by making the minimum-spanning tree. |
| Contig Building | • Assemble contigs using the optimized graph. |
| Universal Phasing | • Use trio phasing to assign contigs to the parents. |

*FIG. 7*

Parent1: C-CGCAG
Parent2: G-ATTTA

Contig Phasing

Universal Phasing

Mom: C-CGCAG
Dad: G-ATTTA

MULTIPLE TAGGING OF LONG DNA FRAGMENTS

RELATED APPLICATIONS

This disclosure claims priority to U.S. patent application Ser. No. 14/782,307, filed Oct. 2, 2015, which a 371 National Phase of PCT/US2014/030649, filed Mar. 17, 2014, which claims priority to U.S. patent application Ser. No. 14/205,145, filed Mar. 11, 2014, and to U.S. provisional application No. 61/801,052, filed Mar. 15, 2013. Each application is hereby incorporated herein by reference in its entirety for all purposes.

REFERENCE TO A SEQUENCE LISTING SUBMITTED AS ASCII TEXT FILES VIA EFS-WEB

The Sequence Listing written in file 092171-1082726-5043-US-2 SequenceListing.txt, created Sep. 24, 2018, 792 bytes, machine format IBM-PC, MS-Windows operating system, is hereby incorporated by reference.

FIELD

This disclosure relates to analysis of nucleic acids, such as genomic DNA, including sequencing and haplotype determination.

BACKGROUND OF THE INVENTION

There is a need for improved methods for determining the parental contribution to the genomes of higher organisms, i.e., haplotype phasing of genomes. Methods for haplotype phasing, including computational methods and experimental phasing, are reviewed in Browning and Browning, Nature Reviews Genetics 12:703-7014, 2011.

Most mammals, including humans, are diploid, with half of the homologous chromosomes being derived from each parent. Many plants have genomes that are polyploid. For example, wheat (*Triticum* spp.) have a ploidy ranging from diploid (*Einkom* wheat) to quadriploid (emmer and durum wheat) to hexaploid (spelt wheat and common wheat [*T. aestivum*]).

The context in which variations occur on each individual chromosome can have profound effects on the expression and regulation of genes and other transcribed regions of the genome. Further, determining if two potentially detrimental mutations occur within one or both alleles of a gene is of paramount clinical importance. For plant species, knowledge of the parental genetic contribution is helpful for breeding progeny with desirable traits.

Some of the current methods for whole-genome sequencing lack the ability to separately assemble parental chromosomes in a cost-effective way and describe the context (haplotypes) in which variations co-occur. Simulation experiments show that chromosome-level haplotyping requires allele linkage information across a range of at least 70-100 kb.

Single molecule sequencing of greater than 100 kb DNA fragments would be useful for haplotyping if processing such long molecules were feasible, if the accuracy of single molecule sequencing were high, and detection/instrument costs were low. This is very difficult to achieve on short molecules with high yield, let alone on 100 kb fragments.

Most recent human genome sequencing has been performed on short read-length (<200 bp), highly parallelized systems starting with hundreds of nanograms of DNA. These technologies are excellent at generating large volumes of data quickly and economically. Unfortunately, short reads, often paired with small mate-gap sizes (500 bp-10 kb), eliminate most SNP phase information beyond a few kilobases (McKernan et al., Genome Res. 19:1527, 2009). Furthermore, it is very difficult to maintain long DNA fragments in multiple processing steps without fragmenting as a result of shearing.

Until recently, only about three personal genomes have been sequenced and assembled as diploid: those of J. Craig Venter (Levy et al., PLoS Biol. 5:e254, 2007), a Gujarati Indian (HapMap sample NA20847; Kitzman et al., Nat. Biotechnol. 29:59, 2011), and two Europeans (Max Planck One [MP1]; Suk et al., Genome Res., 2011; and HapMap Sample NA 12878; Dultama et al., Nucl. Acids Res. 40:2041-2053, 2012). All have involved cloning long DNA fragments into constructs in a process similar to the bacterial artificial chromosome (BAC) sequencing used during construction of the human reference genome (Venter et al., Science 291:1304, 2001; Lander et al., Nature 409:860, 2001). While these processes generate long phased contigs (N50s of 350 kb [Levy et al., PLoS Biol. 5:e254, 2007], 386 kb [Kitzman et al., Nat. Biotechnol. 2959-63, 2011] and 1 Mb [Suk et al., Genome Res. 21:1672-1685, 2011]) they require a large amount of initial DNA, extensive library processing, and are too expensive to use in a routine clinical environment.

Additionally, whole chromosome haplotyping has been demonstrated through direct isolation of metaphase chromosomes (Zhang et al., Nat. Genet. 38:382-387, 2006; Ma et al., Nat. Methods 7:299-301, 2010; Fan et al., Nat. Biotechnol. 29:51-57, 2011; Yang et al., Proc. Natl. Acad. Sci. USA 108:12-17, 2011). These methods are useful for long-range haplotyping but have yet to be used for whole-genome sequencing; they require preparation and isolation of whole metaphase chromosomes, which can be challenging for some clinical samples.

There is also a need for improved methods for obtaining sequence information from mixtures of organisms such as in metagenomics (e.g., gut bacteria or other microbiomes). There is also a need for improved methods for genome sequencing and assembly, including de novo assembly with no or minimal use of a reference sequence), or assembly of genomes that include various types of repeat sequences, including resolution of pseudogenes, copy number variations and structural variations, especially in cancer genomes.

We have described long fragment read (LFR) methods that provide enable an accurate assembly of separate sequences of parental chromosomes (i.e., complete haplotyping) in diploid genomes at significantly reduced experimental and computational costs and without cloning into vectors and cell-based replication. LFR is based on the physical separation of long fragments of genomic DNA (or other nucleic acids) across many different aliquots such that there is a low probability of any given region of the genome of both the maternal and paternal component being represented in the same aliquot By placing a unique identifier in each aliquot and analyzing many aliquots in the aggregate, DNA sequence data can be assembled into a diploid genome, e.g., the sequence of each parental chromosome can be determined. LFR does not require cloning fragments of a complex nucleic acid into a vector, as in haplotyping approaches using large-fragment (e.g., BAC) libraries. Nor does LFR require direct isolation of individual chromosomes of an organism. In addition, LFR can be performed on an individual organism and does not require a population of the organism in order to accomplish haplotype phasing.

LFR methods have been described in U.S. patent application Ser. Nos. 12/329,365 and 13/447,087, U.S. Pat. Publications US 2011-0033854 and 2009-0176234, and U.S. Pat. Nos. 7,901,890, 7,897,344, 7,906,285, 7,901,891, and 7,709,197, all of which are hereby incorporated by reference In their entirety.

SUMMARY OF THE INVENTION

The invention provides methods and compositions for Multiple Tagging of Individual Long DNA Fragments (referred to herein by the abbreviation Multiple Tagging, or MT). MT is useful for analysis of nucleic acids, such as genomic DNA, including sequencing and for analyzing the resulting sequence information to reduce errors perform haplotype phasing, among other things, and perform accurate variant calling, especially for heterozygotes.

Methods are provided in this disclosure for sequencing a target nucleic acid by: (a) combining in a single reaction vessel (i) a plurality of long fragments of the target nucleic acid, and (ii) a population of polynucleotides, wherein each polynucleotide comprises a tag and a majority of the polynucleotides comprise a different tag; (b) introducing into a majority of the long fragments tag-containing sequences from said population of polynucleotides to produced tagged long fragments, wherein each of the tagged long fragments comprises a plurality of the tag-containing sequences at a selected average spacing, and each tag-containing sequence comprises a tag; and (c) producing a plurality of subfragments from each tagged long fragment, wherein each subfragment comprises one or more tags. Such methods are suitable for preparing a target nucleic acid for nucleic acid sequencing, and may comprise sequencing the subfragments to produce a plurality of sequence reads; assigning a majority of the sequence read to corresponding long fragments; and assembling the sequence reads to produce an assembled sequence of the target nucleic acid.

Producing the tagged subfragments by such methods may comprise performing an amplification reaction to produce a plurality of amplicons from each long fragment Each amplicon may comprise a tag from each of the adjacent introduced sequences and a region of the long fragment between the adjacent introduced sequences. Such methods may comprise combining the long fragments with an excess of the population of tag-containing sequences; and/or combining the long fragments with the tag-containing solution under conditions that are suitable for introduction of a single tag-containing sequence into a majority of the long fragments.

Such methods may comprise combining the long fragments with the tag-containing solution under conditions that are suitable for introduction of a different tag-containing sequences into a majority of the long fragments. The population of tag-containing sequences may comprise a population of beads, wherein each bead comprises multiple copies of a single tag-containing sequence, or a concatemer comprising multiple copies of a single tag-containing sequence. In such methods the tag-containing sequences typically comprise transposon ends, the method typically comprising combining the long fragments and the tag-containing sequences under conditions that are suitable for transposition of the tag-containing sequences into each of the long fragments. Alternatively, the tag-containing sequences may be a hairpin sequence. The target nucleic acid may be a complex nucleic acid, such as a genome of an organism.

Such methods may be done for determining a haplotype of the genome, or for any other worthwhile purpose.

Unless otherwise stated or required, any method for analyzing or sequencing according to this invention may comprise amplifying portions of the target nucleic acid to form the initial fragments. This can be done, for example, by inserting transposons into the target nucleic acid; and replicating the target nucleic acid using primers that bind within the transposons, thereby forming the initial fragments. The amplifying may therefore comprise the steps of ligating adapter oligonucleotides into a plurality of the nicks or gaps; and replicating the target nucleic acid using primers that bind within the adaptor oligonucleotides, thereby forming the initial fragments. The amplifying may be conducted with transposons, nicks, or gaps introduced into the target polynucleotide at a frequency of one in about every 3 to 20 kb, or as exemplified elsewhere in this disclosure.

The target nucleic acid may be a complex nucleic acid, such as a genome of an organism. The analyzing can include determining the haplotype of a genome, determining methylation patterns of a genome; and/or determining copy number variation in a cell sample present, for example in the biopsy sample taken from a cancer patient. The methods of this invention can be used for diagnosing or assessing cancer in a patient, or for pre-implantation genetic diagnosis.

This invention also provides products for carrying out a method of this invention. Such products include any new nucleic acid construct or complex described below or shown in the figures, optionally in combination with other components useful for sequencing or analysis of complex DNA. Such components may include a starting substrate or reagent, an intermediate, or a final product of a method of the invention as described below. For example, this invention provides a system for sequencing or analyzing a target nucleic acid. The system includes (a) fragments of the target nucleic acid that of a specific size (for example, about 2 to 5 or about 5 to 750 base pairs in length), a plurality of which each contain or are annealed with multiple copies of an insert sequence comprising a particular tag, wherein different fragments contain insert sequences with a different tag and a common primer sequence; and (b) a set of primers comprising a sequence that specifically anneals to the common primer sequence.

In an aspect the invention provides a method for sequence analysis of a target nucleic acid comprising: (a) combining a plurality of long DNA fragments of the target nucleic acid with a population of tag-containing sequences, wherein the population comprises at least 1000 different tag sequences; (b) producing tagged long fragments, wherein each tagged long fragment comprises target nucleic acid sequence and multiple interspersed tag sequences, wherein the multiple interspersed tag sequences in an individual tagged long fragment may be the same or different; (c) producing from each tagged long fragment a plurality of tagged subfragments, wherein the tagged subfragments each comprise one or more tag sequences; (d) obtaining sequence of individual tagged subfragments, wherein the obtained sequence includes target nucleic acid sequence and at least one tag sequence; (e) combining sequences obtained in (d) to produce assembled sequence(s) of the target nucleic acid, wherein the combining comprises (i) determining that sequences obtained in (d) originated from the same long DNA fragment if said sequences comprise the same tag sequence and/or (ii) identifying pairs of sequences as being adjacent sequences in the target nucleic acid if the pair comprise the same tag sequence. In an aspect, steps (a)-(c) are carried out in a single vessel or mixture. In an aspect, steps the plurality of long DNA fragments are genomic DNA sequence. In an aspect, steps the plurality of long DNA fragments are at least 50 kb, optionally at least 100 kb, in length, or are in the range 50 kb to 200 kb. In some embodiments the tagged long fragments comprise a plurality of the tag-containing sequences at a selected average spacing. In some embodiments the average spacing is in the range 100 to 5000 bases. In some embodiments the average spacing is in the range 200 and 1500 bases. In some embodiments the average spacing is in the range 250 and 1000 bases.

In an aspect, Steps (a)-(c) are carried out in a single vessel or mixture and the single vessel or mixture comprises more than a haploid (N) amount of genomic DNA. In some embodiments the genomic DNA is from a single organism. In some embodiments the genomic DNA comprises fetal DNA and maternal DNA. In some embodiments the genomic DNA is DNA from 1-100 eukaryotic cells.

In some embodiments the genomic DNA is DNA from 2-10 eukaryotic cells. In some embodiments the genomic DNA is DNA from more than 50 eukaryotic cells. In some embodiments the genomic DNA is obtained from a mixture comprising more than one cell type. In some embodiments the DNA is obtained from a mixture comprising more than one cell type from the same species. In some embodiments the cells are (i) fetal cells and maternal cells or (ii) tumor cells and normal cells.

In some embodiments the long DNA fragments are fragments of chromosomal DNA. In some embodiments the long DNA fragments are amplicons of cellular DNA. In some embodiments the long DNA fragments are products of whole genome amplification. In some embodiments comprises amplifying portions of the target nucleic acid to form the long DNA fragments used in Step (a).

In an aspect the tag-containing sequences are clonal tags and the population of tag-containing sequences is a population of sources of clonal tags. In some embodiments the sources of clonal tags comprise beads or other carriers, wherein each bead or carrier has multiple copies of a single tag sequence immobilized thereupon. In some embodiments the sources of clonal tags each comprise at least 1000 copies of a single tag sequence. In some embodiments the population of tag-containing sequences comprises a population of concatemers, each concatemer comprising multiple copies of a single tag-containing sequence. In some embodiments the tag-containing sequences comprise transposon ends. In some embodiments the tag-containing sequences comprise transposon ends. In some embodiments the tag-containing sequences are oligonucleotides that adopt a hairpin conformation. In some embodiments each oligonucleotide comprises two tag sequences. In some embodiments the two tag sequences are the same. In some embodiments the tag-containing sequences of the population comprise primer binding sequences. In some embodiments each of the tag-containing sequences of the population comprise the same primer binding sequences or combination of primer binding sequences.

In an aspect Step (a) comprises combining the long DNA fragments and the tag-containing sequences under conditions that are suitable for transposition of the tag sequences into the long DNA fragments. In a related aspect Step (a) comprises combining the long DNA fragments and a population of sources of clonal tags. In some embodiments the method comprises combining the long DNA fragments with an excess of tag-containing sequences or sources of tag containing sequences.

In an aspect the invention comprised combining the long DNA fragments with the tag-containing sequences under conditions that are suitable for introduction of multiple copies of a single tag sequence into the long DNA fragments, wherein at least 20% of the long DNA fragments comprise only one tag sequence. In some embodiments the conditions are such that a majority of long DNA fragments into which a tag sequence is introduced comprise a unique introduced tag sequence.

In an aspect, on average, each tagged long fragment that comprises interspersed tag sequences comprises at least 10 tag sequences. In some embodiments the multiple interspersed tag sequences in an individual tagged long fragment are the same. In some embodiments, more than 10% the DNA length of a long DNA fragment is represented tagged subfragments.

In some embodiments Step (b) comprises annealing multiple hairpin oligonucleotides onto a plurality of the long DNA initial fragments, wherein each hairpin contains at least two copies of a tag sequence. In some embodiments different hairpins inserted Into one of the initial fragments have different tag sequences. In some embodiments Step (b) comprises (i) annealing multiple hairpin oligonucleotides onto single strands of a plurality of the long DNA fragments; (iii) filling in gaps between hairpin oligonucleotides annealed to the single strands by polymerase extension and ligation.

In some embodiments Steps (b) and (c) comprise: (i) creating nicks or gaps in the long DNA fragments producing free 3' termini, (ii) ligating a 3' common adaptor sequence to the free 3' termini (iii) annealing oligonucleotides to the 3' common adaptor sequence, wherein the oligonucleotides each comprise a tag sequence; and then (iv) extending the first oligonucleotide to form tagged subfragments. In some embodiments in Step (b), transposons, nicks, or gaps are introduced into the long DNA fragment at a frequency of one in about every 300 to 1000 bases.

In an aspect producing the subfragments comprises performing an amplification reaction to produce amplicons from the tagged long fragments. In some embodiments the amplification reaction is PCR. In some embodiments each amplicon comprises a tag from each of the adjacent introduced sequences and a region of the tagged long fragment between the adjacent introduced sequences.

In some embodiments Step (c) comprises forming multiple tagged subfragments that each contain a portion of a tagged transposon and a portion of the long DNA fragment. In some embodiments the tagged transposons have a tag sequence at or near one end that is the same as a tag or sequence at or near the other end.

In an aspect tagged subfragments are formed by amplification, using a primer or primers that anneal to a sequence or sequences within a tag-containing sequence(s).

In an aspect the method comprises: (i) providing primers that each comprise a tag sequence and a random probe sequence: (ii) annealing the primers by way of their respective probe sequences to the long DNA fragments; and (iii) extending the primers to form multiple tagged subfragments. In some embodiments step (i) comprises: annealing copies of a common adaptor oligonucleotide to a tag sequence on each of a plurality of concatemers or beads that is different from tag sequences on other concatemers or beads; and annealing the copies to a plurality of different random probe sequences; and extending the copies to form said primers. In some embodiments formation of the nick or gap and release of tag sequences from the concatemers or beads is done in the same reaction mixture.

In an aspect tagged subfragments are formed by cleaving between two barcodes present in the same tag-containing sequence.

In an aspects of the invention, the sequence of individual tagged subfragments is obtained by sequencing by hybridization, sequencing by ligation, sequencing by synthesis, single-molecule sequencing, optical sequence detection, electro-magnetic sequence detection, or voltage-change sequence detection.

In some embodiments, combining in Step (e) comprises determining that sequences obtained In (d) originated from the same long DNA fragment if said sequences comprise the same tag sequence. In some embodiments, combining in Step (e) comprises identifying pairs of sequences as being adjacent sequences In the target nucleic acid if the pair comprise the same tag sequence.

In aspects of the invention, the method comprises determining a haplotype of the genome. In aspects of the invention, the method comprises methylation analysis of a genome. In aspects of the invention, the method comprises determining copy number variation in cancer cells. In aspects of the invention, the method comprises pre-implantation genetic diagnosis.

In aspects of the invention, the target nucleic acid is genomic DNA of an organism. In some embodiments, the genomic DNA is from a plant or animal. In some embodiments the animal is a mammal. In some embodiments the animal is a human.

In an aspect the invention provides a method for sequence analysis of one or more target nucleic acid molecules comprising: (a) producing a population of subfragments of a single tagged long fragment of the target nucleic acid, wherein the tagged long fragment comprises target nucleic acid sequence and multiple interspersed tag sequences, wherein a majority of the subfragments comprise target nucleic acid sequence and at least one tag sequence; (b) obtaining sequence of individual tagged subfragments, wherein the obtained sequence includes target nucleic acid sequence and at least one tag sequence; (c) combining sequences obtained in (d) to produce assembled sequence(s) of the target nucleic acid, wherein the combining comprises (i) determining that sequences obtained in (d) originated from the same long DNA fragment If said sequences comprise the same tag sequence and/or (ii) identifying pairs of sequences as being adjacent sequences in the target nucleic acid if the pair comprise the same tag sequence.

In an aspect the invention provides a method for sequence analysis of one or more target nucleic acid molecules comprising: (a) obtaining a population of subfragments of a tagged long fragment of the target nucleic acid, wherein the tagged long fragment comprises target nucleic acid sequence and multiple interspersed tag sequences, wherein a majority of the subfragments comprise target nucleic acid sequence and at least one tag sequence; (b) obtaining sequence of individual tagged subfragments, wherein the obtained sequence includes target nucleic acid sequence and at least one tag sequence; (c) combining sequences obtained In (d) to produce assembled sequence(s) of the target nucleic acid, wherein the combining comprises (i) determining that sequences obtained in (d) originated from the same long DNA fragment if said sequences comprise the same tag sequence and/or (ii) identifying pairs of sequences as being adjacent sequences in the target nucleic acid if the pair comprise the same tag sequence.

In an aspect the invention provides a method for sequence analysis of one or more target nucleic acid molecules comprising: (a) obtaining sequence reads from subfragments of a tagged long fragment of the target nucleic acid, wherein the subfragments from which sequence reads are obtained comprise a target nucleic acid sequence and a tag sequence; (b) assembling the sequence reads to produce assembled sequence(s) of the target nucleic acid(s), wherein the assembling comprises assembling adjacent target sequences based on the presence of common tag sequences in pairs of reads corresponding to pairs of adjacent target sequences.

In an aspect the invention provides a method of sequencing a target nucleic acid comprising: combining in a single reaction vessel (i) a plurality of long fragments of the target nucleic acid, and (ii) a population of polynucleotides, wherein each polynucleotide comprises a tag and a majority of the polynucleotides comprise a different tag; Introducing into a majority of the long fragments tag-containing sequences from said population of polynucleotides to produced tagged long fragments, wherein each of the tagged long fragments comprises a plurality of the tag-containing sequences at a selected average spacing, and each tag-containing sequence comprises a tag. In an aspect the invention provides a method for sequence analysis of a target nucleic acid comprising: (a) combining a plurality of long DNA fragments of the target nucleic acid with a population of tag-containing sequences; (b) producing tagged long fragments, wherein each tagged long fragment comprises target nucleic acid sequence and multiple interspersed tag sequences, wherein the multiple interspersed tag sequences in an individual tagged long fragment may be the same or different. In some embodiments Steps (a) and (b) are carried out in a single tube or mixture. In an aspect the method include (c) producing from each tagged long fragment a plurality of tagged subfragments, wherein the tagged subfragments each comprise one or more tag sequences.

In an aspect the invention provides a method of sequencing a target nucleic acid comprising: combining in a single reaction vessel (i) a plurality of long fragments of the target nucleic acid, and (ii) a population of polynucleotides, wherein each polynucleotide comprises a tag and a majority of the polynucleotides comprise a different tag; introducing into a majority of the long fragments tag-containing sequences from said population of polynucleotides to produced tagged long fragments, wherein each of the tagged long fragments comprises a plurality of the tag-containing sequences at a selected average spacing, and each tag-containing sequence comprises a tag; producing a plurality of subfragments from each tagged long fragment, wherein each subfragment comprises one or more tags; sequencing the subfragments to produce a plurality of sequence reads; assign a majority of the sequence read to corresponding long fragments; and assembling the sequence reads to produce an assembled sequence of the target nucleic acid. In some embodiments producing the subfragments comprises performing an amplification reaction to produce a plurality of amplicons from each long fragment. In some embodiments each amplicon comprises a tag from each of the adjacent introduced sequences and a region of the long fragment between the adjacent introduced sequences. In some embodiments the method comprises combining the long fragments with an excess of the population of tag-containing sequences. In some embodiments the method comprises combining the long fragments with the tag-containing solution under conditions that are suitable for introduction of a single tag-containing sequence into a majority of the long fragments. In some embodiments the method comprises combining the long fragments with the tag-containing solution under conditions that are suitable for introduction of a different tag-containing sequences into a majority of the long fragments. In some embodiments the population of tag-containing sequences comprises a population of beads, wherein each bead comprises multiple copies of a single tag-containing sequence. In some embodiments the population of tag-containing sequences comprises a population of concatemers, each concatemer comprising multiple copies of a single tag-containing sequence. In some embodiments the tag-containing sequences comprise transposon ends, the method comprising combining the long fragments and the tag-containing sequences under conditions that are suitable for transposition of the tag-containing sequences into each of the long fragments. In some embodiments the tag-containing sequences comprise a hairpin sequence. In some embodiments the target nucleic acid is a complex nucleic acid. In some embodiments the target nucleic acid is a genome of an organism. In some embodiments the method comprises determining a haplotype of the genome. In some embodiments the population of tag-containing sequences comprises at least 10,000 different tag sequences. In some embodiments the population of tag-containing sequences comprises at least 100.000 different tag sequences.

In an aspect the invention provides a composition in comprising at least $10^3$ different tag-containing nucleic acid elements and at least one of (i) genomic DNA and (ii) primers that bind the tag-containing nucleic acid elements. In some embodiments the composition comprises at least 5 genome equivalents of genomic DNA. In some embodiments the composition comprises both genomic DNA and primers. In some embodiments the composition that comprises tagged long fragments comprising genomic nucleic acid sequence and multiple interspersed tag sequences.

In an aspect the invention provides a kit comprising a library comprising $10^3$ or more distinct bar codes or sources of clonal bar codes: i) a library of barcodes associated with transposon ends, and optionally adaptor sequences; ii) a library of clonal barcodes, optionally with adaptor sequences, comprising a plurality of $10^4$ or more distinct sources of clonal bar codes; iii) a library of concatemers comprising monomers, wherein the monomers comprise bar codes; iv) a library of templates suitable for rolling circle amplification, wherein the templates comprise a monomer as described in (iii); and/or v) a library of hairpin oligonucleotides, each oligonucleotide comprising two copies of a barcode sequence, wherein the library comprises a plurality of at least about $10^4$ barcodes. In some embodiments the kit comprises an enzyme selected from a transposase, a polymerase, a ligase, an endonuclease and an exonuclease. In some embodiments the kit comprises at least about $10^4$, at least about $10^5$, at least about $10^6$, or at least about $10^7$ different barcodes. In some embodiments the kit comprises at least about $10^4$, at least about $10^5$, at least about $10^6$, or at least about $10^7$ different barcodes or sources of clonal barcodes. In some embodiments the library members comprise one or two common sequences for primer binding. In some embodiments the kit comprises a primer or primers that anneal to a sequence or sequences within tag-containing sequence.

Other aspects of the invention will be apparent from the description that follows.

BRIEF DESCRIPTION OF THE DRAWINGS

FIG. 4A shows a method for tagging long fragments of a target nucleic acid using a tagged adaptor. Nickase and Klenow 3-5' exonuclease, without dNTPS, are used to create random sites along long dsDNA for ligation of 3' common adaptor. Similar results can be obtained using any other nicking enzyme and/or exonuclease activity. DNBs or beads with many copies of the tag and complementarity to 3' common adapter are added and fragmented with restriction endonuclease. DNB or bead is close to dsDNA and so most tag copies do not diffuse away, but instead hybridize to 3' adaptor. Long dsDNA and DNB or bead can both be tagged on one end to force interaction if necessary. Primer extension creates tagged genomic DNA fragment. Additional primer extension creates dsDNA that can be ligated and PCR amplified and sequenced. In-silico assembly into long DNA fragments is similar to FIG. 3.

FIG. 4G shows a method for tagging long fragments of a target nucleic acid using controlled nick translation.

FIG. 7 shows the general architecture of the MT algorithm.

DETAILED DESCRIPTION

Figure 1A:
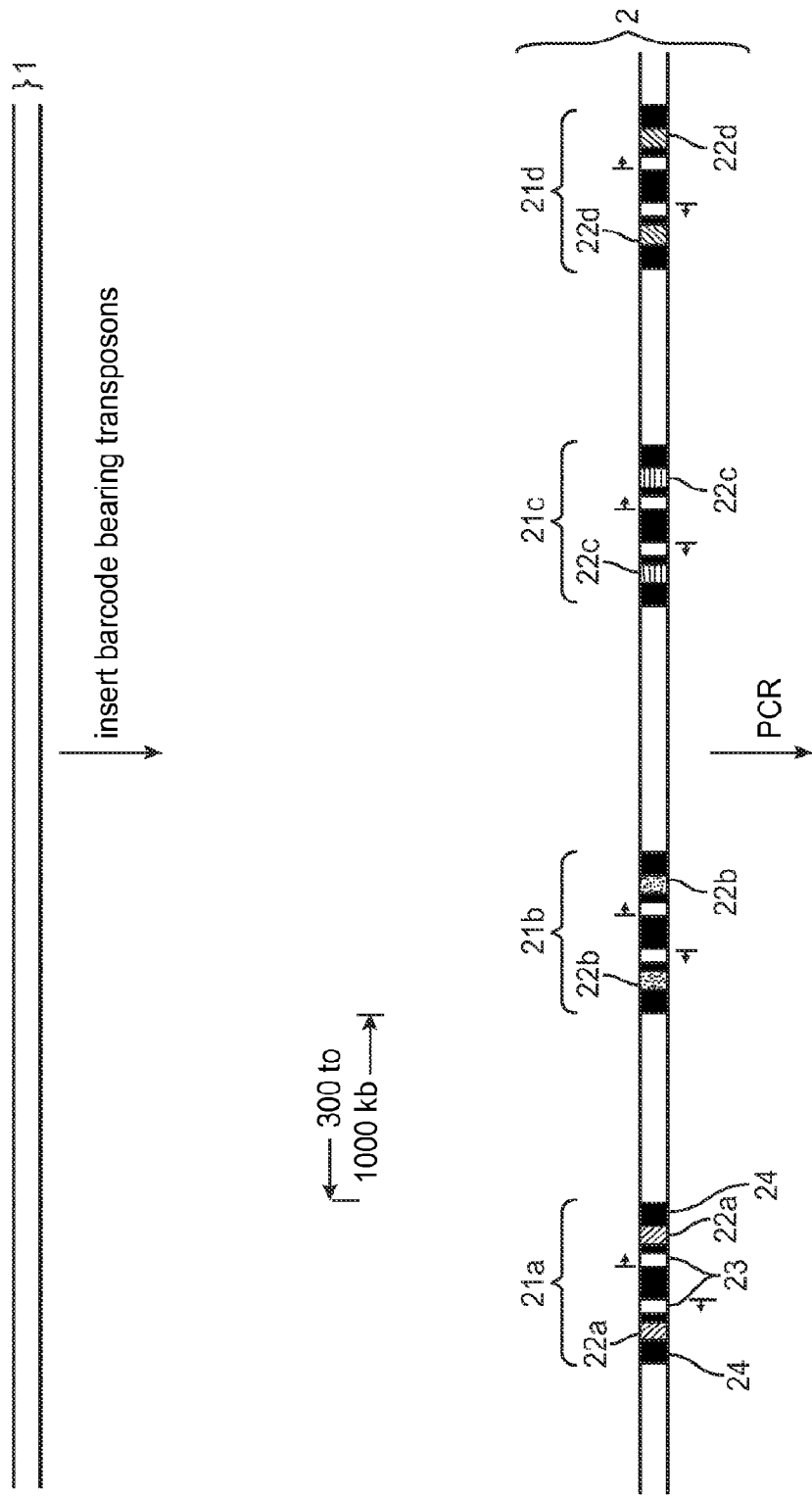
FIGS. 1A and 1B show a method for tagging and fragmenting of long fragments of a target nucleic acid with transposon-mediated barcodes.

As used herein and in the appended claims, the singular forms "a," "an," and "the" include plural referents unless the context clearly dictates otherwise. Thus, for example, reference to "a polymerase" refers to one agent or mixtures of such agents, and reference to "the method" includes reference to equivalent steps and/or methods known to those skilled in the art, and so forth.

Unless defined otherwise, all technical and scientific terms used herein have the same meaning as commonly understood by one of ordinary skill in the art to which this invention belongs. All publications mentioned herein are incorporated herein by reference for the purpose of describing and disclosing devices, compositions, formulations and methodologies which are described in the publication and which might be used in connection with the presently described invention.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

In the following description, numerous specific details are set forth to provide a more thorough understanding of the present invention. However, it will be apparent to one of skill in the art that the present invention may be practiced without one or more of these specific details. In other instances, well-known features and procedures well known to those skilled in the art have not been described in order to avoid obscuring the invention.

Although the present invention is described primarily with reference to specific embodiments, it is also envisioned that other embodiments will become apparent to those skilled in the art upon reading the present disclosure, and it is intended that such embodiments be contained within the present inventive methods.

The practice of the present invention may employ, unless otherwise indicated, conventional techniques and descriptions of organic chemistry, polymer technology, molecular biology (including recombinant techniques), cell biology, biochemistry, and immunology, which are within the skill of the art. Such conventional techniques include polymer array synthesis, hybridization, ligation, and detection of hybridization using a label. Specific illustrations of suitable techniques can be had by reference to the example herein below. However, other equivalent conventional procedures can, of course, also be used. Such conventional techniques and descriptions can be found in standard laboratory manuals such as Genome Analysis: A Laboratory Manual Series (Vols. I-IV), Using Antibodies: A Laboratory Manual, Cells: A Laboratory Manual, PCR Primer: A Laboratory Manual, and Molecular Cloning: A Laboratory Manual (all from Cold Spring Harbor Laboratory Press). Stryer, L. (1995) Biochemistry (4th Ed.) Freeman, New York, Gait, "Oligonucleotide Synthesis: A Practical Approach" 1984, IRL Press, London, Nelson and Cox (2000), Lehninger. Principles of Biochemistry 3rd Ed., W. H. Freeman Pub., New York, N.Y. and Berg et al. (2002) Biochemistry, 5th Ed., W. H. Freeman Pub., New York, N.Y., all of which are herein incorporated in their entirety by reference for all purposes.

Overview

According to one aspect of the invention, methods are provided for multiple tagging of individual long fragments of target nucleic acids, or polynucleotides, including without limitation complex nucleic acids. Long fragments of a target nucleic acid or polynucleotide are tagged by a method that introduces a tag or barcode into multiple sites in each long fragment. In principle, each fragment may have introduced into it multiple copies of one unique tag—a fragment-specific tag—or a unique pattern of insertion of multiple tags—a fragment-specific tag pattern. However, this is not required. As discussed below, in some embodiments some long fragments may have no tag inserted. Further, in some embodiments, a long fragment may have inserted into it more than one distinct tag, and two or more fragments may have inserted into them the same tag.

"Long fragments" are polynucleotides greater than 10 kb In length, more often greater than 20 kb in length, even more often greater than 50 kb in length, and very often 100 kb or longer. For haplotyping, long fragments 100 kb or longer are particularly useful.

After tagging, subfragments of the long fragments are produced. In principle, each subfragment may include at least one tag. Again, this is not required. As discussed below, in some embodiments some subfragments may have no tag inserted.

Commonly, the tag-containing subfragments are amplified (e.g., by PCR). The subfragments, including the tags that are part of each subfragment, are then sequenced. The tag sequence permits the sequence data obtained from each subfragment to be assigned to the long fragment from which the subfragment is derived. This facilitates sequence mapping and assembly and the ordering of alleles (or hets) into a haplotype of the target nucleic acids.

Attaching or inserting barcodes into long DNA fragments can be performed in a single mixture or container (e.g., single tube or single well in a multi-well plate) and the process may be automated. Using MT, the single mixture in which tagging occurs contains more than one genome equivalent. In various embodiments the mixture may comprise at least 5 genome equivalents, at least 10 genome equivalents, at least 25 genome equivalents, at least 50 genome equivalents, at least 100 genome equivalents, at least 500 genome equivalents, or at least 1000 genome equivalents, such as from 5-20 genome equivalents, such as from 5-100 genome equivalents, such as from 50-1000 genome equivalents.

In some applications, a single cell may be analyzed in a single MT mixture, providing only two complementary strands (i.e., two genome equivalents) for discriminating natural variation from errors introduced by DNA processing, e.g. amplification of sub-fragments.

According to one embodiment, a majority of the subfragments, or 60%, 70%, 80%, 90% or more, or substantially all of the subfragments, include a tag sequence. In one aspect, this invention provides a system for tagging of long DNA fragments using clonal barcodes. As is detailed below, "clonal barcodes" refers to a plurality of barcodes or tags that have a common sequence and which are physically associated with each other (rather than physically separate and, for example, free to diffuse in solution). In this approach, a source of clonal tags can be associated with a single long DNA fragment. The result is that a plurality of identifiable clonal tags or barcodes may be associated with one DNA fragment and not with others. The clonal tags or barcodes may be kept together in the form of, without limitation, concatemers, dendrimers, or on a carrier such as a polymer (e.g., DNA fragment) or micro-size beads. Using clonal barcodes allows preparation of millions of distinct barcodes at relatively modest expense for use in "single-tube" MT.

In one aspect MT involves (a) providing (i) a library of clonal barcodes and (ii) long DNA fragments; (b) preparing (by nicking-gaping, random primer extension or transposon insertion) the DNA fragments for attaching barcodes (e.g., at predefined average distance on the long DNA fragments): (c) attaching multiple barcode copies per long DNA molecule (e.g., at the predetermined average distance); (d) preparing (by primer extension or PCR or DNA fragmenting) multiple short DNA fragments from a long fragment tagged with copies of the same barcode. Before step (c)

individual barcode copies are produced from, e.g., released from, a concatemer (DNB) or support (i.e., a bead or other carrier).

In another aspect, MT involves (a) providing (i) a library of barcodes and (ii) long DNA fragments; (b) incorporating the barcode sequences into the long DNA sequences (e.g., at predefined average distance on the long DNA fragments); (c) preparing multiple subfragments in which sequences that are from the same long fragment, such as sequences that are adjacent to each other in the long fragment sequence, are tagged with copies of the same barcode. In one approach, a library of copy-paste transposons containing barcodes is used to get multiple barcode copies per one long DNA fragment. A copy-paste transposon with a barcode attached to the end of a long DNA fragment is able to insert copy of barcode and associated sequences at multiple places in the long fragment.

For accurate clinical sequencing and haplotyping of Individual human genomes from a small number of cells, long genomic fragments (~100 kb or longer) are preferable, although shorter fragments may be used. Assuming 100 kb fragments, a human genome would have about $6 \times 10^4$ fragments per cell, and ~18 cells would generate about 1 million fragments. DNA tags that are 12 bases long (12-mers) or longer have enough sequence diversity (16 million to over one billion) to tag each fragment with a unique tag.

We provide several illustrative methods for associating copies of the same long tag to hundreds of ~1 kb sub-regions of ~100 kb genomic fragments in a homogenous reaction without any physical compartmentalization (e.g., droplets in an emulsion). It will be recognized that the MT is not limited to these particular methods.

In some embodiments of the invention, such methods lead to a majority (e.g., 50%) or 60%, 70%, 80%, 90% or more of the long fragments of a target nucleic acid being tagged with multiple tag-containing sequences that include the same tag sequence. Such methods minimize tagging with different tag sequences, for example: selecting the proper ratio of tag-containing sequences to long fragments; selecting the proper dilution or DNA concentration; minimizing molecule movement after initiation of the tagging process, for example, by mixing DNA fragments, tag-containing sequences, and enzymes and buffers at low temperature, waiting for liquid movements to stop, and then increasing the temperature of the mixture in order to activate enzymatic processes); tethering a single tag-containing sequence to a single long DNA fragment by covalent or non-covalent binding; and other techniques. There are several ways to attach or tether a single bead or nanoball with multiple copies of a particular tag-containing sequence to a single long fragment of a target nucleic acid. For example, a homopolymer sequence (e.g., and A-tail) may be added to the long fragment using terminal transferase or an adaptor with a selected sequence may be ligated to an end or ends of the long fragment. A complementary sequence may be added to the end of or included within the tag-containing sequence or nanoball such that, under selected appropriate conditions, the tag-containing sequence or tag assembly anneals with the corresponding complementary sequence on the long fragment. Preferably, a long fragment can anneal to only one tag-containing sequence or tag assembly.

MT avoids subcloning of fragments of a complex nucleic acid into a vector and subsequent replication in a host cell, or the need to isolate individual chromosomes (e.g., metaphase chromosomes). It also does not require aliquoting fragments of a target nucleic acid. MT can be fully automated, making it suitable for high-throughput, cost-effective applications. Tagging ~1 kb sub-regions of long (~100 kb or longer) genomic fragments with the same unique tag has many applications, including haplotyping diploid or polyploid genomes, efficient de novo genome sequence assembly, resolving genomic repeats, accurate variant calling, and error correction.

The advantages of MT include:
   A practically unlimited number of individual DNA fragments can be uniquely tagged, providing maximal information for de novo assembly, for example.
   MT may be performed in a single reaction vessel (e.g., tube, well in a multi-well plate, etc.) in a small number of steps and is easy to scale and automate; there is no need for a large number of aliquots or nanodrops.
   One MT method, which employs nicking and a primer-ligation process, uses both strands of the dsDNA, thereby doubling the sequence coverage per fragment (longer mate-pairs for the same read-length).
   MT reduces the computational demands and associated costs of sequence mapping and assembly.
   Substantial reduction In errors or questionable base calls that can result from current sequencing technologies, including, for example, systematic errors that are characteristic of a given sequencing platform or mutations introduced by DNA amplification. MT thereby provides a highly accurate sequence of a human genome or other complex nucleic acid, minimizing the need for follow up confirmation of detected variants and facilitates adoption of human genome sequencing for diagnostic applications.

MT can be used as a preprocessing method with any known sequencing technology, including both short-read and longer-read methods. For example 1-10 kb tagged subfragments can be sequenced with single molecule methods, without a need to make mate-pairs, and used in accurate genome assembly or genetic variant detection in spite of having high error rate in raw-reads. MT also can be used in conjunction with various types of analysis, including, for example, analysis of the transcriptome, methylome, etc. Because it requires very little input DNA, MT can be used for sequencing and haplotyping one or a small number of cells, which can be particularly useful for cancer, prenatal diagnostics, and personalized medicine. This can facilitate the identification of familial genetic disease, etc. By making it possible to distinguish calls from the two sets of chromosomes in a diploid sample, MT also allows higher confidence calling of variant and non-variant positions at low coverage. Additional applications of MT include resolution of extensive rearrangements in cancer genomes and full-length sequencing of alternatively spliced transcripts.

MT can be used to process and analyze complex nucleic acids, including but not limited to genomic DNA, that is purified or unpurified, including cells and tissues that are gently disrupted to release such complex nucleic acids without shearing and overly fragmenting such complex nucleic acids.

In one aspect, MT produces virtual read lengths of approximately 100-1000 kb or longer in length, for example.

In addition to being applicable to all sequencing platforms, MT-based sequencing is suitable for a wide variety of applications, including without limitation the study of structural rearrangements in cancer genomes, full methylome analysis including the haplotypes of methylated sites, and de novo assembly applications for individual human genomes, metagenomics or novel genome sequencing, even of complex polyploid genomes such as those found in plants.

MT provides the ability to obtain actual sequences of individual chromosomes as opposed to just the consensus sequences of parental or related chromosomes (in spite of their high similarities and presence of long repeats and segmental duplications). To generate this type of data, the continuity of sequence is in general established over long DNA ranges.

A further aspect of the invention includes software and algorithms for efficiently utilizing MT data for whole chromosome haplotype and structural variation mapping and false positive/negative error correction.

Controlled primer extension and controlled nick translation can be used to randomize ends of clonal fragments generated by initial amplification of tagged DNA.

One or more of the following features may be part of the MT protocol:

1) Minimizing instances In which more than one different barcode is inserted per long DNA fragment, by selecting appropriate concentrations (i.e., appropriate dilution) of clonal barcodes and long DNA fragments so that less than 0.1%, less than 1%, or less than 10% of long DNA fragments are tagged with multiple barcodes sequences. There optimal dilutions will depend on factors such as the amount of target DNA available. For example, an excess of long DNA fragments over barcodes may be used when DNA is not limiting (e.g., using a blood or saliva sample), while an excess of barcodes over DNA may be used we the starting material is limited to a few cells and it is desirable to tag every fragment. When DNA is not limiting (e.g., more than 20, more than 50, more than 100 or more than 500 genome equivalents In the reaction mixture) it is not necessary to optimally tag every single fragment. Instead, it may be advantageous to sacrifice some yield to minimize the tagging of a DNA fragment with different barcodes. In one approach DNA fragments are present in excess amount relative to clonal barcodes. Using an excess of DNA fragments over the number of different clonal barcodes increases the likelihood that only one or a few DNA fragments are close to any one barcode to allow tagging. It also allows to have more space between clonal barcodes to minimize having two different barcodes per one DNA fragment. An excess of about 3-, 10-, 30-, 100- or even 300-fold may be used in different reaction configurations. More than 10,000, more than 100,000, or more than 1,000,000 different barcodes may be used.

2) A gel-like medium (e.g. low melting agarose gel blocks or other polymers such as PEG) may be used to minimize movement of liquid, limiting mixing and interactions of different clonal barcodes and different long DNA molecules.

3) Using pre-gaped DNA, where, before mixing DNA with clonal barcodes, gaps are introduced in DNA e.g. by transposon and ready for barcode ligation. In this approach, gapped-DNA is prepared (e.g., by nicking and gapping), followed by addition of barcodes and a tagging (ligation) step performed on pre-gapped DNA. This approach reduces the enzymatic complexity of the reaction mixture.

4) In-gap ligating of adapter-barcode to 3' DNA end without complementarity to target DNA or to 5' end using 2-8 degenerated bases; and/or 5) Long DNA gaping, releasing individual barcode copies and attaching of barcodes to DNA is done as one reaction (i.e. all need enzymes, clonal barcodes and long DNA present in the mix before starting incubation). Alternatively, only barcode releasing and attaching is done as one reaction; DNA gapping is done as a preceding step.

6) When copy-paste transposons are used the DNA concentration should be appropriately low to minimize "jumping" transposons between long DNA fragments. A molecule of copy-paste transposon with a barcode sequence provides clonal barcodes within one long DNA fragment and not the other DNA fragments if such DNA fragments are separated enough to prevent transposon jumping from one DNA to the other.

In one approach, a small amount of DNA (e.g., from 10 cells) is tagged in a single container. Clonal tags are interacted with DNA in a small volume to give high probability that almost all long DNA fragments will find a clonal barcode (DNB or a bead with DNB or a bead with a clonally amplified adapter-barcode oligonucleotide). An excess of DNA binding capacity is provided by the clonal barcodes and associated carriers. DNA binding capacity is defined by the number of DNBs or beads or other carrier and the number of DNA fragments that can be bound per DNB or bead or other carrier. For illustration, the genomes of 10 human cells are equivalent to 1 million 60 kb-fragments. If an excess of clonal barcode DNBs is used, such as 10 million DNBs, this would correspond to the number of DNBs per ~10 µl reaction to tag ~10 million fragments (as described in the example of using 100-fold excess of DNA or one billion fragments). Note that even for the case of having excess of DNA and the need to tag 10 million fragments, if carrier can bind multiple DNA fragments, then ~106 clonal tags may be sufficient.

Almost all long DNA fragments from a limited DNA amount (e.g. 3-30 human cells) can be tagged with multiple copies of the same barcode per long DNA fragment. This can be done by: (a) providing >10K or 100K or 1M clonal barcodes and a small amount of long DNA fragments, wherein total DNA binding capacity of "clonal barcode entities" exceeds provided amount of DNA; (b) associating almost all long DNA fragment(s) in high concentration to the carrier of the clonal barcodes or modified clonal barcode entities (for certain applications, each clonal barcode entity has limited DNA binding capacity of <100 kb, <300 kb, less than 1 Mb); (c) diluting or spacing clonal barcode entities before barcode cutting/releasing and DNA tagging (to minimize having more than one distinct barcode per DNA); (d) tagging long DNA fragments (at predefined average distance) with barcode copies from the associated clonal barcode entity. In some embodiments, longer sequence reads, such as 2×100-300 bases or entire 1-3 kb sub-fragments, are preferred, so that more bases are read per each long fragment.

Using excess of clonal-barcode particles or excess of total binding capacity can help ensure that almost all DNA fragments are used and that either (i) it is rare that more than one fragment is bound to the same clonal-barcode carrier or (ii) a predefined average number of fragments is bound to the same clonal barcode entity. The clonal or synthetic barcodes can be attached on a surface such that there is no dilution after DNA binding to barcode spots. Surface bound spaced clonal barcodes can be arranged as follows: A 1 cm$^2$ chip with 10$^6$ distinct tags bound to spots that are ~0.5-2 µm in size and spaced at 10 um, with total binding capacity >66 pg DNA, preferably >100 pg, more than 300 pg, or >1 ng. DNA is loaded from 10 cells in 5-10 µl volume. With proper incubation time and optional mixing most of DNA fragments may bind to clonal barcode spots. Barcodes on such chip can be prepared by oligo synthesis instead of by cloning process. The surface is configured such that long DNA does not attach to the surface between spots.

This invention provides products for advanced DNA barcoding. Such products include a barcoded DNA library (optionally prepared in a single reaction) comprising >10K, >100 k, >1M, or >10M barcodes and on average >15%, >20%, >25%, >30%, 40%, or >50% of sequence of a long DNA fragment are represented in barcoded fragments (optionally, the long DNA fragments are not amplified). The long fragment is represented in short DNA fragments tagged with the copies of the same barcode. Tagged DNA fragments can be amplified and optionally one or both fragment ends are randomized. As few as 100, 50, 30, 20, or 10 cells or fewer are used to make the library.

Preparing Long Nucleic Acid Fragments

Target nucleic acids, including but not limited to complex nucleic acids, may be isolated using conventional techniques, for example as disclosed in Sambrook and Russell, *Molecular Cloning: A Laboratory Manual*, cited supra. In some cases, particularly if small amounts of the nucleic acids are employed in a particular step, it is advantageous to provide carrier DNA, e.g., unrelated circular synthetic double-stranded DNA, to be mixed and used with the sample nucleic acids whenever only small amounts of sample nucleic acids are available and there is danger of losses through nonspecific binding, e.g., to container walls and the like.

According to some embodiments of the invention, genomic DNA or other complex nucleic acids are obtained from an individual cell or small number of cells with or without purification, by any known method.

Long fragments are desirable for the methods of the present invention. Long fragments of genomic DNA can be isolated from a cell by any known method. A protocol for isolation of long genomic DNA fragments from human cells is described, for example, in Peters et al., *Nature* 487:190-195 (2012). In one embodiment, cells are lysed and the intact nuclei are pelleted with a gentle centrifugation step. The genomic DNA is then released through proteinase K and RNase digestion for several hours. The material can be treated to lower the concentration of remaining cellular waste, e.g., by dialysis for a period of time (i.e., from 2-16 hours) and/or dilution. Since such methods need not employ many disruptive processes (such as ethanol precipitation, centrifugation, and vortexing), the genomic nucleic acid remains largely intact, yielding a majority of fragments that have lengths in excess of 150 kilobases. In some embodiments, the fragments are from about 5 to about 750 kilobases in lengths. In further embodiments, the fragments are from about 150 to about 600, about 200 to about 500, about 250 to about 400, and about 300 to about 350 kilobases in length. The smallest fragment that can be used for haplotyping is one containing at least two hats (approximately 2-5 kb); there is no maximum theoretical size, although fragment length can be limited by shearing resulting from manipulation of the starting nucleic acid preparation.

In other embodiments, long DNA fragments are isolated and manipulated in a manner that minimizes shearing or absorption of the DNA to a vessel, including, for example, isolating cells in agarose in agarose gel plugs, or oil, or using specially coated tubes and plates.

A controlled use of a 5 exonuclease (either before or during amplification) can promote multiple replications of the original DNA from a single cell and thus minimize propagation of early errors through copying of copies.

Fragmented DNA from a single cell can be duplicated by ligating an adaptor with single stranded priming overhang and using an adaptor-specific primer and phi29 polymerase to make two copies from each long fragment. This can generate four cells-worth of DNA from a single cell.

According to one embodiment of the invention, one starts with more long fragments than are needed for sequencing to achieve adequate sequence coverage and tags only a only a portion of the long fragments with a limited number of tag-containing sequences, or tag assemblies—which include many, perhaps hundreds, of copies of one tag sequence—to increase the probability of unique tagging of the long fragments. Non-tagged subfragments lacking introduced sequences that provide primer-binding or capture-oligo binding and may be eliminated in downstream processing. Such tag assemblies include, for example, end-to-end concatemers of tag-containing sequences created by rolling circle replication (DNA nanoballs), beads to which are attached many copies of the tag-containing sequences, or other embodiments.

According to another embodiment, in order to obtain uniform genome coverage in the case of samples with a small number of cells (e.g., 1, 2, 3, 4, 5, 10, 10, 15, 20, 30, 40, 50 or 100 cells from a microbiopsy or circulating tumor or fetal cells, for example), all long fragments obtained from the cells are tagged.

Preserving Fragment Ends

Once the DNA is isolated, it is advantageous to avoid loss of sequences from the ends of each fragment, since loss of such material can result in gaps in the final genome assembly. In one embodiment, sequence loss is avoided through use of an infrequent nicking enzyme, which creates starting sites for a polymerase, such as phi29 polymerase, at distances of approximately 100 kb from each other. As the polymerase creates a new DNA strand, it displaces the old strand, creating overlapping sequences near the sites of polymerase initiation. As a result, there are very few deletions of sequence.

MT can be Carried Out Using Clonal Barcodes, Including Synthetically Made Clonal Barcodes The terms "barcode", "tag", "barcode sequence". "tag sequence", and obvious variations of these are used interchangeably, have the normal meaning in the art, and refer generally to an identifiable (usually unique) or sequence of nucleotides, heterologous to the target sequence. In a population or library of tags, unique barcodes are sometimes associated with common adaptor sequences, on one or both sides of the barcode, that may be shared by many or all members of the population or library.

Tagging" refers to associating (e.g., inserting) a tag sequence with a polynucleotide. Tagging long fragments involves introducing into long fragments multiple copies of sequences (adaptors, transposons, etc.) that include tags. Such "introduced sequences" are spaced apart on the fragment. Typically the average spacing between adjacent introduced sequences is selected to permit the creation of tag-containing subfragments of the long fragments. Subfragments can be made by any suitable method, e.g. by PCR amplification using primers that have primer binding sites in adjacent introduced sequences; by restriction digestion; or by other methods known in the art. Subsequently, sequence reads are generated by sequencing subfragments of the tagged long fragments. Such sequence reads can be assigned to the individual long fragment from which they are ultimately derived.

In some embodiments of MT, a source of clonal tags or barcodes is used. By "clonal" is meant tags or barcodes containing (i.e., comprising) the same sequence and physically associated with each other (rather than separate and free to diffuse in solution) such that a source of clonal tags can be associated with a single long DNA fragment. The result is that a plurality of identifiable clonal tags or barcodes may be associated with one DNA fragment and not with others. The clonal tags or barcodes may be kept together in the form of concatemers, dendrimers, or on a carrier such as a polymer (e.g., DNA fragment) or micro-size beads. The terms "particle" and "source of clonal barcodes" are also used in this disclosure to refer to a delivery system for multiple copies, of a tag sequence.

An example of a source of clonal barcodes is a concatemer, the monomers of which contain a barcode and optionally other associated sequences, such as transposon sequences, or restriction enzyme recognition sites. In one approach, concatemers are made using RCR, e.g., as described below. The concatemers can be single- or double-stranded. Double-stranded concatemers may be prepared, for example, by primer extension of single stranded concatemers. Sequences can be released from concatemers using, for example, (1) by treatment with restriction or nicking enzymes that recognize sites in each monomer, (2) by treatment with a transposase; (3) by amplification (e.g., PCR amplification) using, for example, primer binding sites in each monomer (4) by delivering a cleaving reagent (e.g. a chemical group or a binding site for a restriction or nicking enzyme cutting downstream from the binding site) on a fully or partially complementary oligonucleotide, or (5) random fragmenting by non-specific endonuclease (which would generate only a fraction of usable barcodes).

Another example of a source of clonal barcodes is a particle (e.g., a bead or other support structure) with a plurality of oligonucleotides immobilized thereon. In one approach the oligonucleotides are covalently attached to the support, e.g., by a cleavable linker. In another one approach the oligonucleotides are non-covalently attached to the support. The oligonucleotides may be released from the support using any suitable method such as treatment with a restriction enzyme that released a fragment of the attached oligonucleotide. Alternatively a linker may be cleaved. In one approach a linker can be nucleic acid with modified bases such as uracil that can be cleaved enzymatically or chemically. Any of a number of methods of disassociating oligonucleotides may be used.

Also contemplated are use of sources with a small number (e.g. 2 or 3) of different tag sequences, such as a bead associated with "sequence a" and "sequence b". In this case it would be recognized that "sequence a" and "sequence b" will be inserted into the same long fragment, and "sequence a" and "sequence b" will be treated as equivalent in the process of sequence assembly.

Making Sources of Clonal Tags or Barcodes

Concatemers (e.g., DNA Nanoballs) of Tag/Transposon Sequences

One source of clonal tags (especially tags including or associated with transposon sequences) is a concatemer, the monomers of which contain the clonal sequence. A circular or circularized (e.g., as with padlock probes) DNA template can be amplified by rolling circle replication (RCR). RCR uses the phi29 DNA polymerase, which is highly processive. The newly synthesized strand is released from the circular template, resulting In a long single-stranded DNA concatemer comprising many head-to-tail copies of the circular DNA template. The concatemer folds into a substantially globular ball of DNA that is called a DNA nanoball (DNB). The length of the DNB and the number of copies of the DNA template can be controlled by the length of the RCR reaction. The nanoballs remain separated from each other in solution.

Tag/Transposon Sequences Associated with Beads or Other Supports

A source of clonal barcodes such as a bead or other support associated with multiple copies of tags can be prepared by emulsion PCR or CPG (controlled-pore glass) or chemical synthesis other particles with copies of an adapted-barcode prepared by. A population of tag-containing DNA sequences can be PCR amplified on beads in an water-in-oil (w/o) emulsion by known methods. See, e.g., Tawfik and Griffiths Nature Biotechnology 16: 652-656 (1998); Dressman et al., Proc. Natl. Acad. Sci. USA 100: 8817-8820, 2003; and Shendure et al., Science 309:1728-1732 (2005). This results in many copies of each single tag-containing sequence on each bead.

Another method for making a source of clonal barcodes is by oligonucleotide synthesis on micro-beads or CPG in a "mix and divide" combinatorial process. Using this process one can create a set of beads each having population of copies of a barcode. For example, to make all $B_{20}N_{15}B_{20}$ where each of about 1 billion is represented In ~1000+ copies on each of 100 beads, on average, one can start with ~100 billion beads, synthesize $B_{20}$ common sequence (adaptor) on all of them and then split them in 1024 synthesis columns to make a different 5-mer in each, then mix them and then split them again in 1024 columns and make additional 5-mer, and then repeat that once again to complete N15, and then mix them and in one big column synthesize the last $B_{20}$ as a second adaptor. Thus, in 3050 syntheses one can make the same "clonal-like" sets of barcodes as in one big emulsion PCR reaction with ~1000 billion beads ($1^{12}$ beads) because only 1 in 10 beads will have a starting template (the other 9 would have none) to prevent having two templates with different barcode per bead.

Characteristics of Tags

According to one embodiment, a barcode- or tag-containing sequence is used that has two, three or more segments of which, one, for example, is the barcode sequence. For example, an introduced sequence may include one or more regions of known sequence and one or more regions of degenerate sequence that serves as the barcode(s) or tag(s). The known sequence (B) may include, for example, PCR primer binding sites, transposon ends, restriction endonuclease recognition sequences (e.g., sites for rare cutters, e.g., Not I, Sac II, Mlu I, BssH II, etc.), or other sequences. The degenerate sequence (N) that serves as the tag is long enough to provide a population of different-sequence tags that is equal to or, preferably, greater than, the number of fragments of a target nucleic acid to be analyzed.

According to one embodiment, the tag-containing sequence comprises one region of known sequence of any selected length. According to another embodiment the tag-containing sequence comprises two regions of known sequence of a selected length that flank a region of degenerate sequence of a selected length, i.e., $B_nN_nB_n$, where N may have any length sufficient for tagging long fragments of a target nucleic acid, including, without limitation, N=10, 11, 12, 13, 14, 15, 16, 17, 18, 19 or 20, and B may have any length that accommodates desired sequences such as transposon ends, primer binding sites, etc. For example, such an embodiment may be $B_{20}N_{15}B_{20}$.

In one embodiment, a two- or three-segment design is utilized for the barcodes used to tag long fragments. This design allows for a wider range of possible barcodes by allowing combinatorial barcode segments to be generated by ligating different barcode segments together to form the full barcode segment or by using a segment as a reagent in oligonucleotide synthesis. This combinatorial design provides a larger repertoire of possible barcodes while reducing the number of full-size barcodes that need to be generated. In further embodiments, unique identification of each long fragment is achieved with 8-12 base pair (or longer) barcodes.

In one embodiment, two different barcode segments are used. A and B segments are easily be modified to each contain a different half-barcode sequence to yield thousands of combinations. In a further embodiment, the barcode sequences are incorporated on the same adapter. This can be achieved by breaking the B adaptor into two parts, each with a half barcode sequence separated by a common overlapping sequence used for ligation. The two tag components have 4-6 bases each. An 8-base (2×4 bases) tag set is capable of uniquely tagging 65,000 sequences. Both 2×5 base and 2×8 base tags may include use of degenerate bases (i.e., "wildcards") to achieve optimal decoding efficiency.

In further embodiments, unique identification of each sequence is achieved with 8-12 base pair error correcting barcodes. Barcodes may have a length, for illustration and not limitation, of from 5-20 informative bases, usually 8-16 informative bases.

Tagging Signal Long Fragments

The methods of the present invention employ various approaches to introduce multiple copies of a tag at multiple spaced-apart sites along a long fragment (e.g., 100 kb or longer) of the target nucleic acid without the need to divide the long fragments into aliquots (as in the long fragment read technology): the entire process can be performed in a single tube or well in a microtiter plate.

According to one embodiment of the invention, tags are introduced at intervals of between about 300 bp and 1000 bp along the fragment. This spacing can be shorter or longer, depending on the desired fragment size for subsequent processing, e.g., library construction and sequencing. After tagging, each subfragment of the long fragment and any sequence information derived from it can be assigned to a single long fragment.

Long Fragments Containing the Same Tag or Barcode

In some embodiments of the invention, such methods result in most (e.g., 50%, 60%, 70%, 80%, 90% or more) of the long fragments of a target nucleic acid being tagged with multiple tag-containing sequences that include the same tag sequence. Steps can be taken to minimize tagging with different tag sequences, for example: selecting the proper ratio of tag-containing sequences to long fragments; selecting the proper dilution or DNA concentration: minimizing molecule movement after initiation of the tagging process, for example, by mixing DNA fragments, tag-containing sequences, and enzymes and buffers at low temperature, waiting for liquid movements to stop, and then increasing the temperature of the mixture In order to activate enzymatic processes); tethering a single tag-containing sequence to a single long DNA fragment by covalent or non-covalent binding; and other techniques.

Long Fragments Containing a Unique Fingerprint

In other embodiments of the invention, rather than maximizing the number of long fragments with a single tag sequence inserted at multiple locations along the long fragment. MT involves providing conditions under which multiple tags with different sequences are inserted at multiple locations, creating a unique pattern or "fingerprint" for each long fragment that is provided by a unique pattern of insertion of the different-sequence tags.

Exemplary methods for tagging single fragments are described below.

(1) Tagging with Transposons

Several approaches to MT make use of transposon sequences and/or transposases. Any suitable transposon/transposase or transposon/integrase system may be used to introduce tagged transposons. Examples include in vitro Mu transposition (Haapa et al., Nucl. Acids Res., 27:2777-2784, 1999; Savilahti et al., EMBO J. 14:4893-4903, 1995); Ty1 (Devine and Boeke, Nucl. Acids Res., 22:3765-3772, 1994; International Patent Application WO 95/23875); Tn7 (Craig, Curr. Topics Microbiol. Immunol. 204:27-48, 1996); Tn 10 and IS 10 (Kleckner et al., Curr. Top. Mlcroblol. Immunol. 204:49-82, 1996); Mariner (Lampe et al., EMBO J. 15:5470-5479, 1996); Tc1 (Vos et al., Genes Dev., 10:755-761, 1996); Tn5 (Park et al., Taehan Misaengmul Hakhoechi 27:381-389, 1992); P element (Kaufman and Rio, Cell 69:27-39, 1992); Tn3 (Ichikawa and Ohtsubo. J. Biol. Chem. 265: 18829-18832, 1990); bacterial insertion sequences (Ohtsubo and Sekine, Curr. Top. Microbiol. Immunol., 204:1-26, 1996); retroviruses (Varmus and Brown, "Retroviruses," in Mobile DNA. Berg and Howe, eds., American Society for Microbiology, Washington, D.C., pp. 53-108, 1989); and yeast retrotransposons (Boeke, "Transposable elements in *Saccharomyces cerevisiae*," in Mobile DNA. Berg and Howe, eds., American Society for Microbiology, Washington, D.C., pp. 53-108, 1989). Other known transposons include, without limitation, AC7, Tn5SEQ1, Tn916, Tn951, Tn1721, Tn 2410, Tn1681, Tn1, Tn2, Tn4, Tn6, Tn9, Tn30, Tn101, Tn903, Tn501, Tn1000 (γ6), Tn1681, Tn2901, AC transposons, Mp transposons, Spm transposons, En transposons, Dotted transposons, Ds transposons, dSpm transposons and I transposons. Modified forms of the transposon ends and/or transposases may be used. e.g., a modified Tn5 transposase as in the Nextera™ technology (Epicentre Biotechnologies. Madison. Wis.).

Many transposases recognize different insertion sequences, and therefore it is to be understood that a transposase-based vector will contain insertion sequences recognized by the particular transposase also found in the transposase-based vector. Transposases and insertion sequences from eukaryotic transposon-based vectors can be modified and used including. However, non-eukaryotic transposon-based elements reduce the likelihood that a eukaryotic transposase in the recipient organism (e.g., human subject) will recognize prokaryotic insertion sequences bracketing the transgene.

Figure 1B:
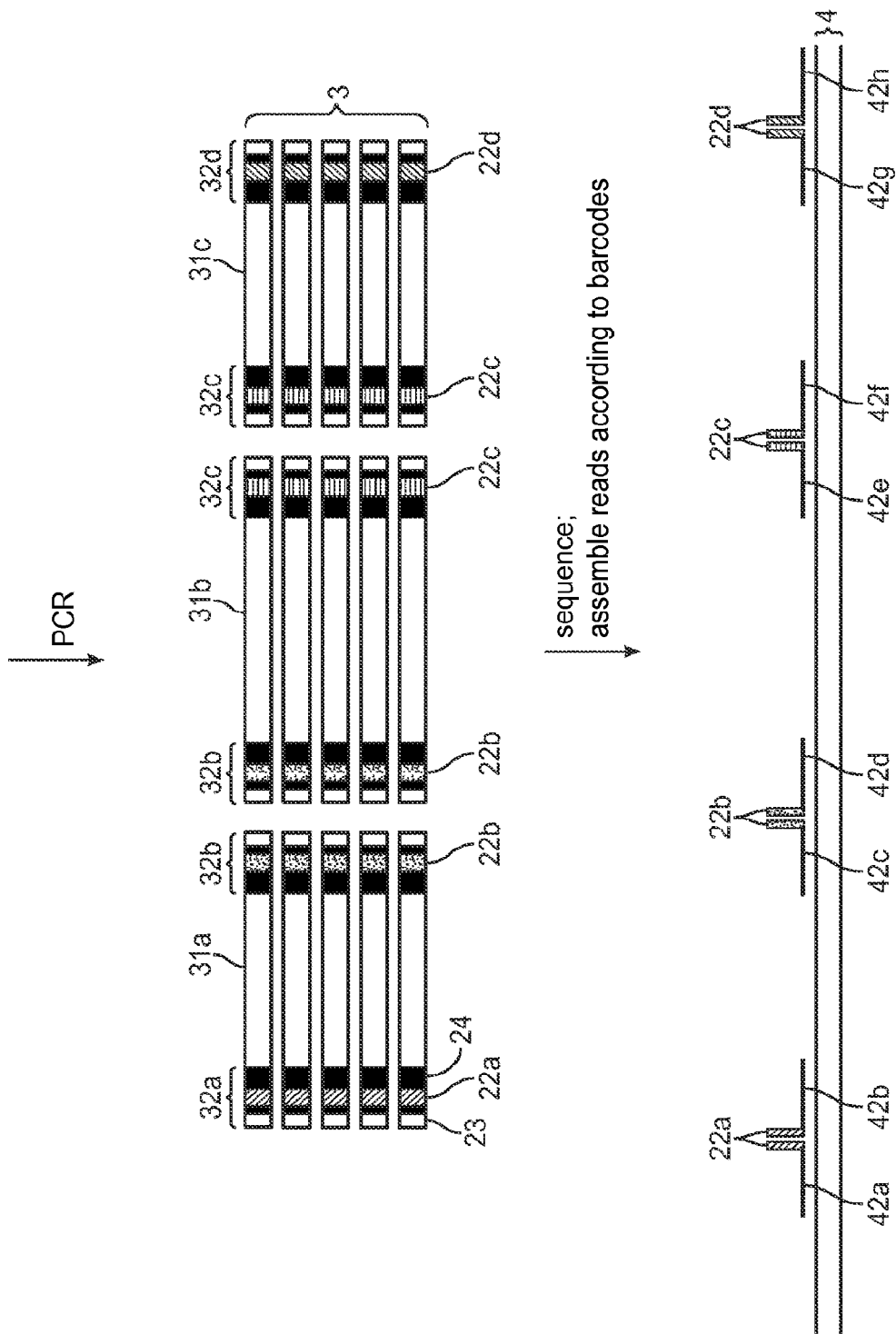

A first approach involves In vitro transposition (see FIGS. 1A and 1B). A population of tagged transposons is used 21*a*, 21*b*, 21*c*, 21*d*. Tagged transposons are DNA constructs that include transposon ends 24, and near each of the ends, pairs of unique tag (barcode) sequences 22*a*, 22*b*, 22*c*, 22*d* (the same tag sequence near both ends), and a common PCR primer binding site 23. The population of transposons is combined with long fragments 1 of a target nucleic acid. Addition of transposase causes in vitro transposition of several of the tagged transposons into the long fragments 2. Each long fragment has a unique pattern of transposon insertion, and each inserted transposon has a unique tag sequence (bar code). In addition, the act of transposition replicates 9 bp of sequence at each end of the transposon that further distinguishes each transposon insertion event (and may be considered another form of "tagging").

PCR is performed using primers that bind to the PCR primer binding sites 23 of each inserted transposon. The resulting PCR amplicons 3 include a portion of the long fragment 31*a*, 31*b*, 31*c*, 31*d* that lies between adjacent transposon portions 32a, 32b, 32c, 32d. At each end of the amplicons (i.e., flanking the target, or long fragment, sequence) are sequences from the end of an adjacent transposon, including the unique tag (barcode) sequence for that transposon 22a, 22b, 22c, 22d.

After sequencing the PCR amplicons, it is possible not only to map the sequence reads to a reference genome, assuming such is available, but to use the tags to build contigs to guide de novo assembly. Each sequence read 42a to 42h is associated with a tag sequence 22a, 22b, 22c, 22d. A particular tag sequence (or pattern of tags, e.g., a pair of tags or a chain of tags) corresponds to a single fragment. Thus, sequence reads from the same fragment should map within the same region of the target nucleic acid. In general, two different amplicons (such as 31a and 31b) have the same unique tag 22b from one transposon at their ends and are thus adjacent to one another in the long fragment from which they are derived.

The sequence reads are assembled using matched adjacent barcodes to build long reads, each comprising a tag sequence 21a to 21d together with a sequence of part 42a, 22b, 42c, 42d, 42e of the initial fragment. Sequence reads are continuous or discontinuous depending on sequence read length. If more than one genome equivalent of long fragments is analyzed (e.g., 2, 3, 4, 5, 10, or 20 or more genome equivalents) building up contigs out of sequence reads derived from overlapping long fragments is straightforward.

(2) Tagging with Hairpins

Figure 2A:
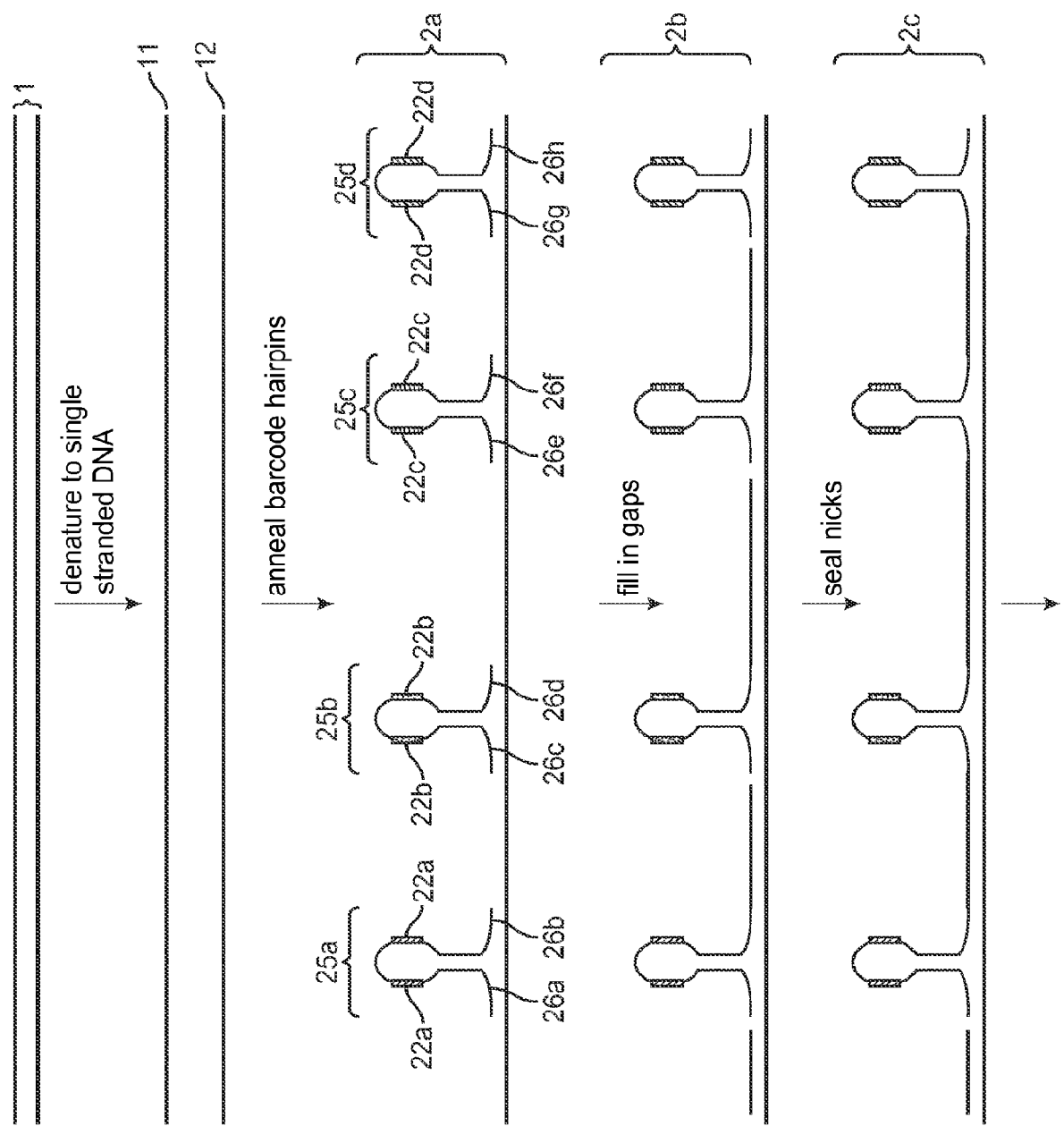
FIGS. 2A and 2B show a method for tagging and fragmenting of long fragments of a target nucleic acid with hairpin-mediated barcodes.
Figure 2B:
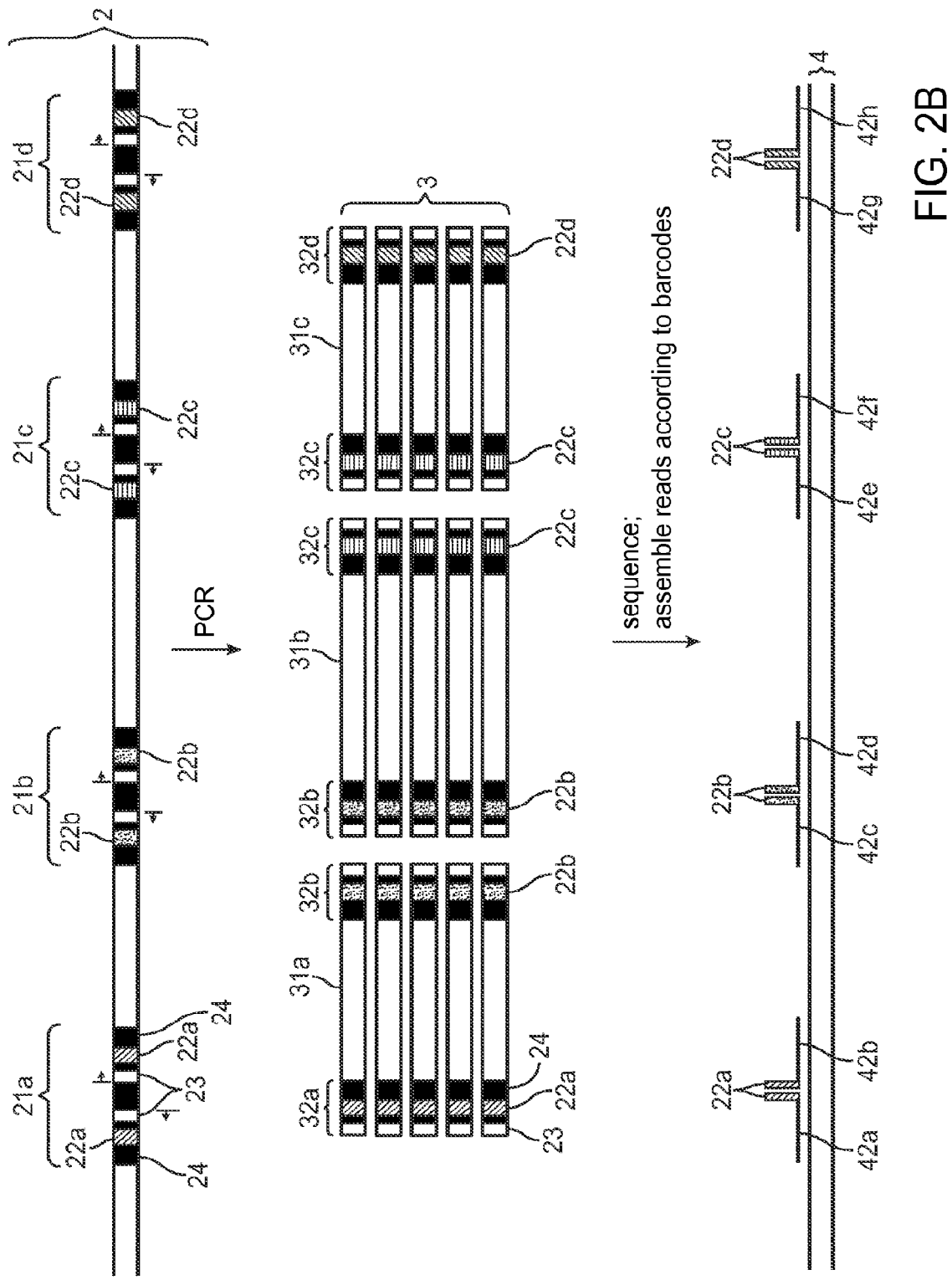

This approach begins with long fragments of a target nucleic acid 1 that are denatured to form two complementary single strands from each fragment 11, 12. See FIGS. 2A and 2B. It also uses a population of oligonucleotides (25a, 25b, 25c, 25d) that form hairpins, each including tag sequences 22a, 22b, 22c, 22d in the loop that flank PCR primer binding sites and having a short stretch of random bases (e.g., 3-5 bases) 26a to 26h at each end. The hairpin oligos are annealed 2a to the single stranded form 11 of the starting long fragments spaced apart, for example, by about 300 to 1000 bp. Each long fragment has a unique pattern of annealed hairpins. After annealing the single stranded region between adjacent hairpins is filled-in 2b with a 5'-3' polymerase that lacks strand displacement, followed by ligase treatment to seal the remaining nick 2c.

PCR amplification 3 using primers that bind to the PCR binding sites 23 between the bar code sequences of each hairpin creates amplicons that have a portion of the long fragment 31a, 31b, 31c, 31d that lies between the binding sites of adjacent hairpin oligonucleotides. At each end such amplicons include sequences from the loop of an adjacent hairpin oligonucleotide, including the unique tag sequence for that oligonucleotide 22a, 22b, 22c, 22d. In the same manner as method (1) above, the bar code sequences at the ends of the PCR amplicons can be used to build contigs 4 to guide de novo mapping and assembly.

(3) Tagging with Transposons on a DNA Nanoball or Bead

This approach, and several others discussed herein, use a particle (such as a DNB or bead) containing many copies of the same tag sequence. In some cases, the tags include transposon sequences. Association of polynucleotides with beads is well known in the art, and is briefly described above. Likewise, production of DNA concatemers (e.g., DNA nanoballs or DNBs) is well known In the art, and is briefly described below.

Figure 3:
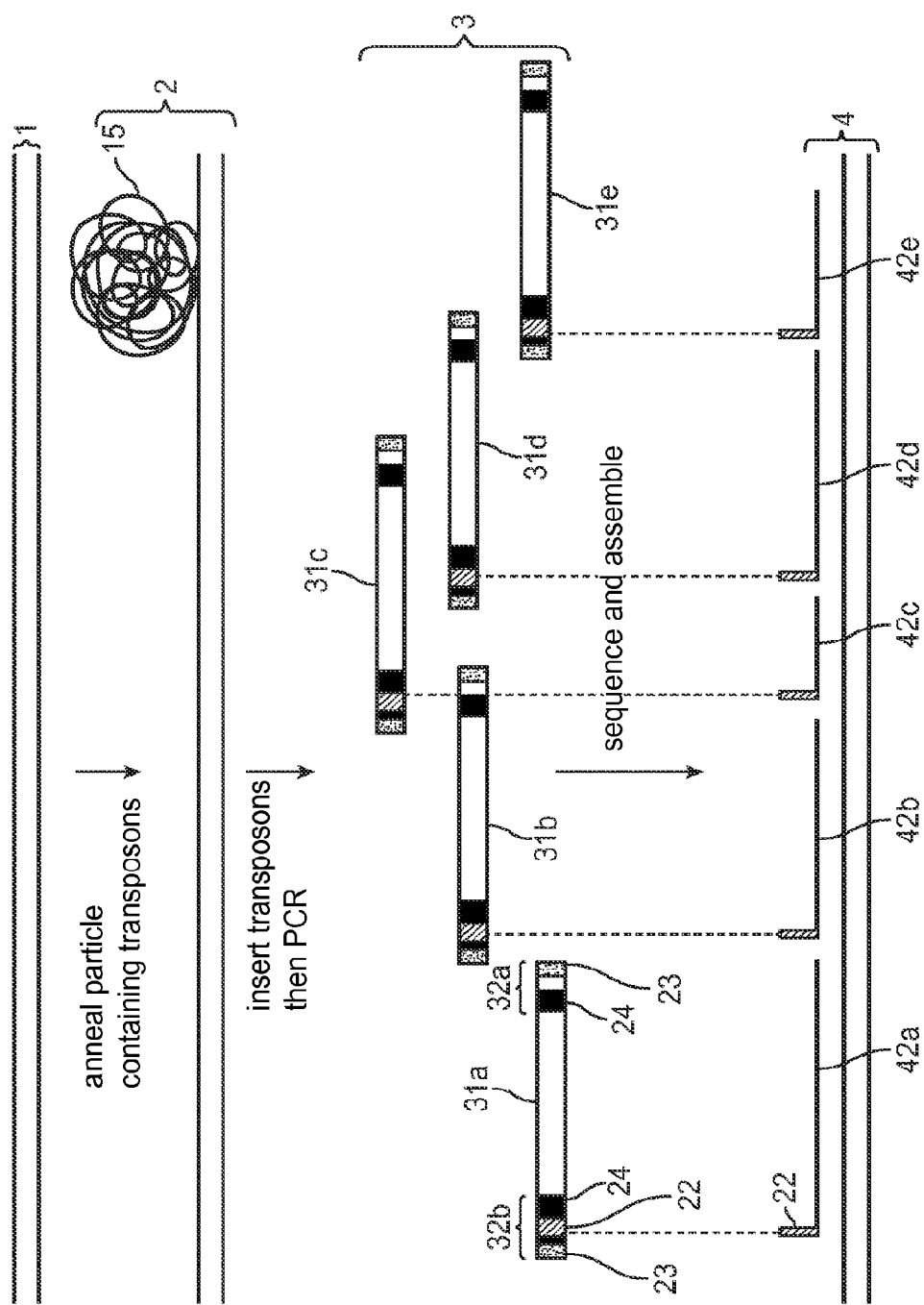
FIG. 3 shows a method for transposon-mediated tagging and fragmenting of long fragments of a target nucleic acid.

The approach illustrated in FIG. 3 employs a particle 15 from which transposon sequences may be released: for example, beads covered with transposon sequences, or a concatemer of transposon sequences created by rolling circle replication of a circular DNA that includes the transposon sequence—a transposon nanoball. As in method (1) above, the "transposon sequences" are DNA constructs that include (i) transposon ends 24 and, (ii) at a selected location in the transposon sequences 31a to 31e between the transposon ends (near each of the transposon ends), tag sequences 22 (optionally, the same tag sequence can be near both ends), and (iii) a common PCR primer binding site 23.

The transposon-containing bead or nanoball 15 is combined with the long fragments 1 of a double stranded target nucleic acid. Conditions are selected to promote the interaction of only one tag assembly, i.e., bead or nanoball bearing a single transposon sequence, with each long fragment. For example, at the correct dilution, only one bead or nanoball 15 interacts with each long fragment in most cases, since diffusion is slow and most transposons don't travel far from a long fragment. Alternatively, the transposon sequence or another sequence on the transposon assembly (e.g., an adaptor ligated to an end of the transposon sequence or concatemer; a homopolymer sequence added by a terminal transferase) can be used to bind by hybridization one oligonucleotide containing one barcode sequence representing one transposon molecule. Upon addition of transposase, transposition occurs (not shown). In most cases, each fragment received multiple copies of the same transposon sequence. A minority of the long fragments may receive copies of more than one transposon. Also, in a minority of cases, a transposon with a particular tag may transpose into more than one long fragment.

As In method (1), PCR amplification is performed using primers that bind to the PCR primer binding sites 23 of each inserted transposon. The resulting PCR amplicons 3 (between about 300 bp and 1000 bp in length) include a portion of the long fragment 31a, 31b, 31c, 31d, 31e that lies between adjacent transposons; at each end such amplicons include sequences from the end of an adjacent transposon 32a, 32b, including the unique tag sequence (barcode) for that transposon 22 in either or both of the transposase portions 32a and 32b. The constructs are amplified and sequenced. After sequencing, sequence reads 42a, 42b, 42c, 42d, 42e are mapped and assembled. The barcode 22 is a label for the particular long fragment 1.

In this method, because most long fragments are tagged with multiple copies of a single transposon, the resulting amplicons have the same tag at each end. The tags permit each sequence read to be associated with the same long fragment, although it is not possible to build up contigs based on the ordering of the tag sequences alone as in methods (1) and (2). If more than one transposon inserts into a single long fragment, it is most likely that all of the transposons that insert into one long fragment insert only into that one long fragment and not into other fragments. As a result, sequence reads associated with each of the inserted tags maps closely together in the genome (or other target nucleic acid). Even if this is not the case, and the same transposon jumps into more than one fragment, the likelihood is high that the fragments into which such transposon is inserted are non-overlapping, in which case the resulting sequence reads map to widely separated regions of the genome. Mapping and assembly software can account for these events and correctly map and assemble the sequence reads into a genome sequence and order sequence polymorphisms (hets) into a haplotype.

(4) Tagging with Tagged Adaptors

Figure 4B:
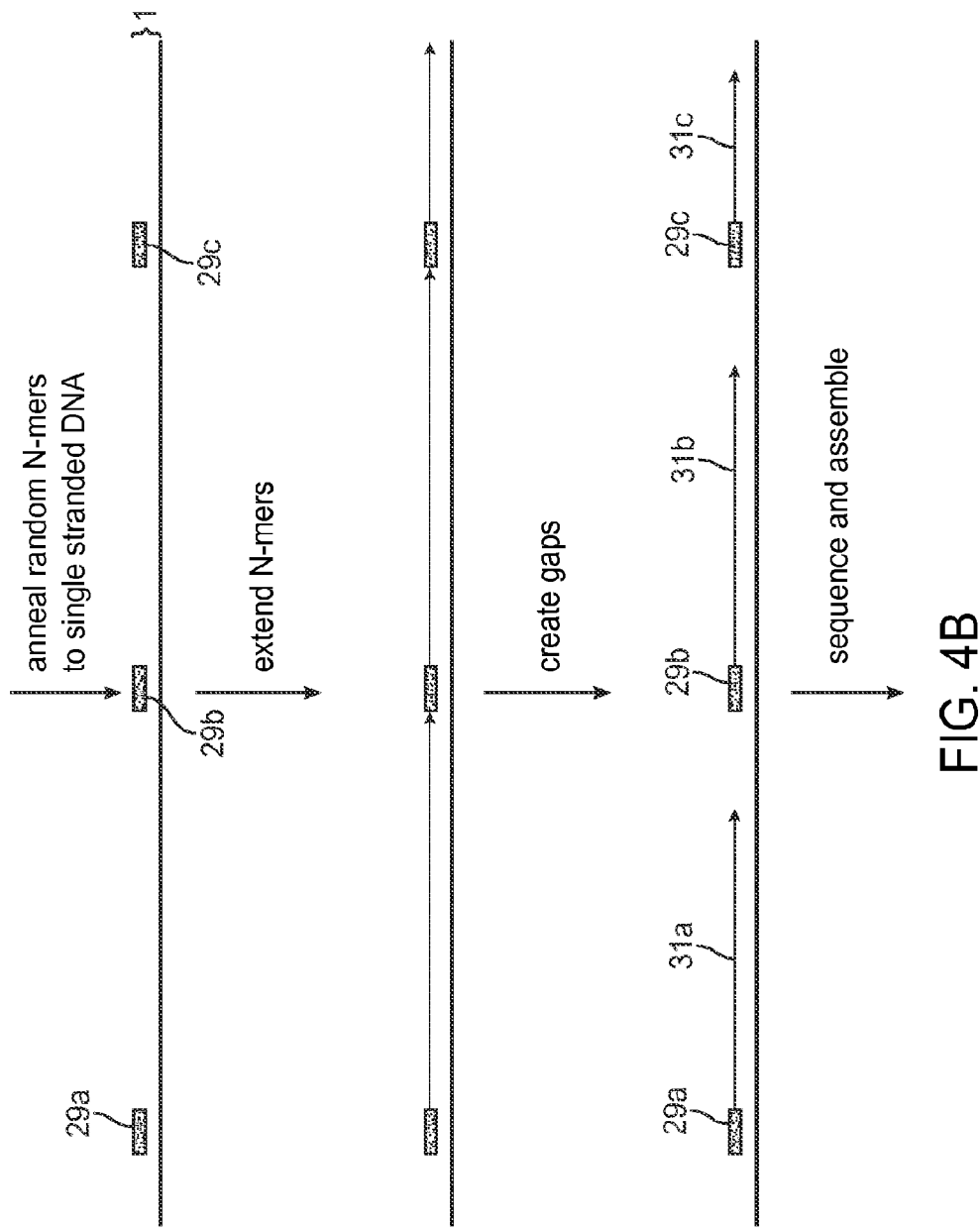
FIG. 4B shows an alternative method for tagging long fragments of a target nucleic acid using a tagged adaptor.

In this method, long double-stranded fragments 1 of a genome (or other target nucleic acid) are nicked at random locations on both strands using an agent such as DNase I that nicks DNA double strands (i.e., a "nickase") and DNA polymerase I large (Klenow) fragment, which retains polymerization and 3'→5' exonuclease activity, but has lost 5'→3' exonuclease activity. See FIG. 4A. No dNTPs are included in the reaction. A 3' common adaptor 27 is ligated to the 3' end of each strand at a nick. A particle 15 (such as a bead or DNA) with many copies of a sequence (e.g., oligonucleotide) that includes (i) the tag sequence 22 and (ii) a sequence 28 that is complementary to the 3' common adapter 27 is added under conditions that permit the 3' common adaptor to hybridize to the complementary sequence. For example, the DNB may be fragmented (e.g., with a restriction endonuclease or nickase) or oligonucleotide released from the bead.

As also described elsewhere herein, at the proper ratio of long fragments to beads or nanoballs and at the proper dilution, most of the fragments are spatially associated with one (or less frequently 2 or more) beads or nanoballs, and copies of the 3' common adaptor hybridize to the complementary sequence on a single bead or nanoball, since a single hybridization event leads to a physical interaction between the long fragment and the bead or nanoball, bringing other complementary sequences into close proximity. In other words, a particle is close to the dsDNA fragment, so most tag copies do not diffuse away, but instead hybridize to 3' adaptor.

Alternatively, and as also described below, the long dsDNA fragments and nanoballs or beads can both be tagged on one end to force interaction if necessary. For example, one can use complementary DNA sequences such as an A-tail on the long fragment and a T-tail or poly-T region on the tag-containing sequences, or other interactive moieties, to force the interaction of the long fragment and tag-containing sequences in order to increase the likelihood that each long fragment has introduced into it multiple copies of a single tag-containing sequence. Next, the tag-containing nucleic acids on the bead or nanoball are fragmented, e.g., with a restriction endonuclease, which results in common adaptors ligated to the long fragment hybridizing to complementary sequences that are included in the nucleic acids released from the bead or nanoball. Primer extension using DNA polymerase I large fragment (Klenow) or a similar DNA polymerase results in the creation of a 3' tagged molecule spaced apart on the long fragment every 300-1000 bp.

The long DNA molecule can then be denatured and an oligonucleotide can be hybridized to the 3' common adaptor; extension with Klenow fragment or a similar polymerase results in a blunt-ended, double-stranded DNA molecule that can be ligated to a 5' common adaptor and PCR amplified. The resulting PCR amplicons (effectively tagged subfragments of the long DNA fragments) are then sequenced, mapped and assembled in a fashion similar to that described in method (3).

Thus, according to this method of the invention, the MT process may comprise:
I) "Clonal" copying of barcode templates and required adapters, for example by (a) rolling circle replication (RCR) to make a concatemer with hundreds of copies of the same tag or by (b) emulsion PCR on beads to create thousands of copies. Optionally, the copied unit may represent a transposon.
II) Mixing long genomic fragments and tag-adapter concatemers or beads in the proper ratio and in proper concentrations to have majority, most or almost all genomic fragments spatially associated with one concatemer and infrequently with two or more.
III) Adding a universal primer to genomic DNA by: (a) nicking of genomic DNA at predefined frequency (e.g., 1 kb) using partial nicking with frequent nicker or other methods; controlled nick translation can be used to further randomize fragment start sites; optionally a small gap may be created at the nicking site, e.g., by exo activity of Pol I or Klenow without dNTPs; (b) ligating a primer by 5' end to 3' end of nicked DNA by providing the primer hybridized with a short complementary dideoxy oligo at the 5' end: this primer is complementary to an adapter next to the barcode. Optionally this step can be done before step two or mixing genomic DNA with clonal tags;
IV) Copying the tag from tag donor (DNA nanoball or bead) and another adapter by primer extension using tag templates. After DNA denaturing this results in ~1 kb ssDNA fragments with an adapter-barcode-adapter extension at 3' end. These fragments can be used as sequencing templates by a primer complementary to the 3' end adapter or converted in dsDNA by the same primer and further process (e.g., ligate an adapter on the other end, amplify, circularize) before sequencing.

Optionally steps 3 and 4 can be replaced by transposon insertion and fragmenting or amplification if concatemers or beads represent clones of tagged transposons.

(5) Insertion without Nicking—Method 1

An alternative approach to inserting tag-containing sequences does not rely on nicking. See FIG. 4B. Long fragments 1 are denatured (e.g., by heating) to produce complementary single strands. Random primers (N-mers) 29a, 29b, 29c are annealed to the single strands and extended with polymerase. An alkaline phosphatase (e.g., shrimp alkaline phosphatase. SAP) is added, and polymerase having a 3'→5' exonuclease function (e.g., Klenow) is used to create gaps. The resulting partially double-stranded product comprising random N-mers 29a, 29b, 29c in-between portions of the long fragment to be sequenced 31a, 31b, 31c is handled as described above and in FIG. 4A, beginning with 3' ligation of a common adaptor.

(6) Insertion without Nicking—Method 2

Figure 4C:
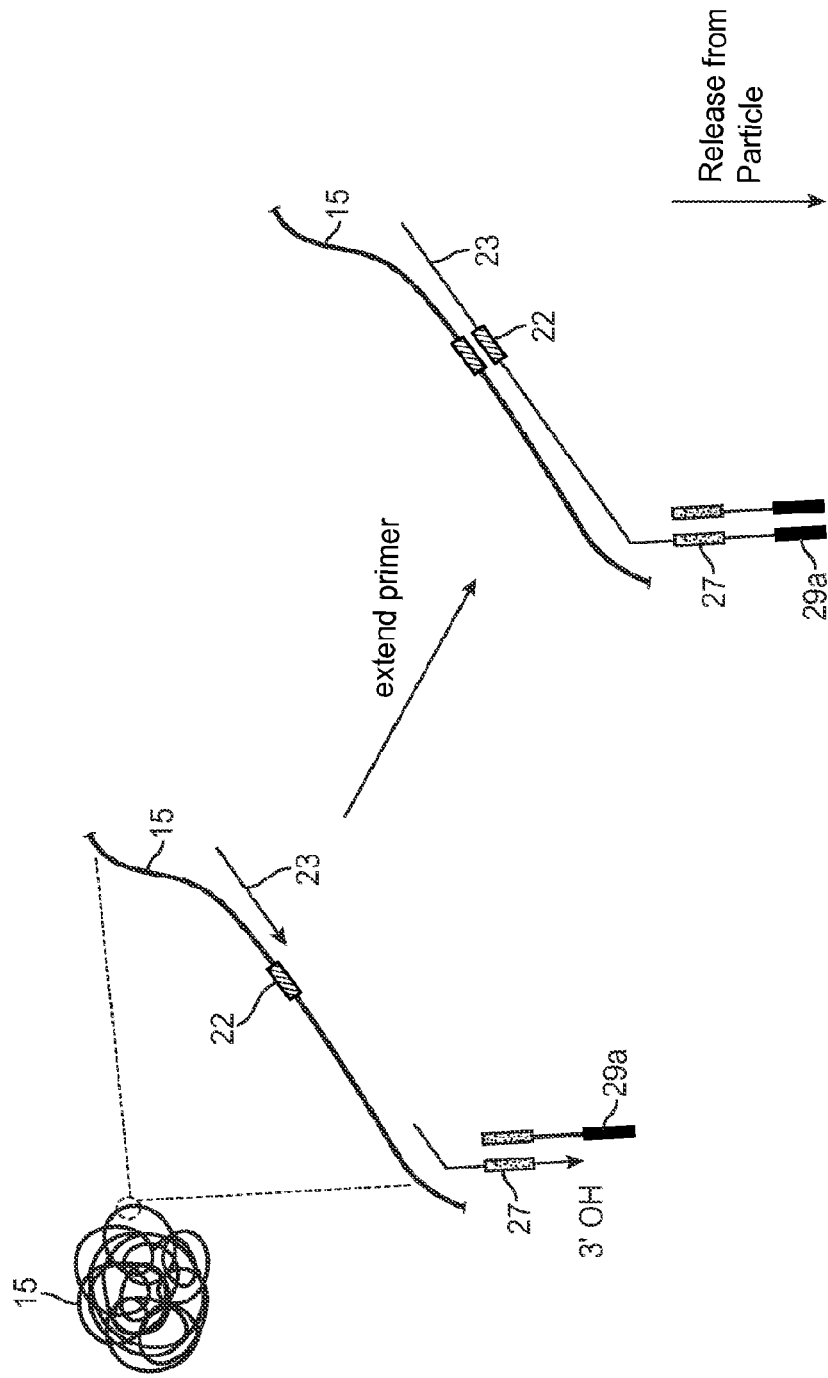
FIGS. 4C and 4D show a second alternative method for tagging long fragments of a target nucleic acid using a tagged adaptor.

A second alternative approach inserts tag-containing sequences without nicking, using a particle. See FIGS. 4C and 4D. In this approach, two oligonucleotides are annealed to a tag-containing sequence carried on a particle 15 such as a bead or as a monomer unit of a DNA concatemer or nanoball: (i) a common primer 23, which is annealed upstream of the tag or barcode sequence 22 and (ii) a common adapter 27 that is annealed downstream of the tag. The primer is extended and ligase is added to ligate the primer extension product to the common adaptor 27. This ligation product thus includes the tag sequence 22 and, at its 3' end, the common adaptor 27.

Figure 4D:
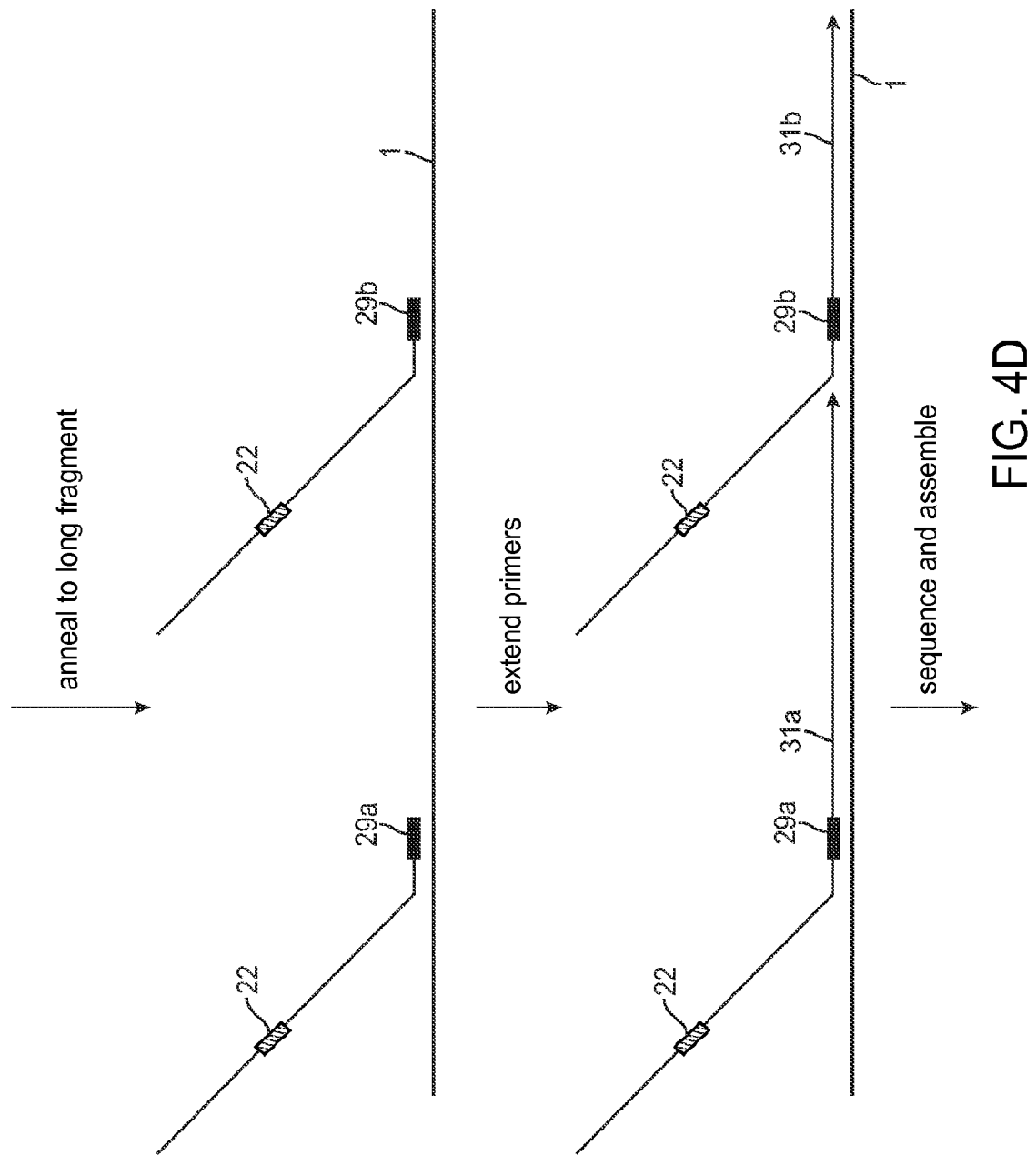

A population of oligonucleotides that includes (i) a degenerate sequence (random N-mer) 29a at its 5' end, (ii) a sequence complementary to the common adaptor 28, and (Iii) noncomplementary sequence (not shown in FIG. 4C) is annealed to the ligation product from the previous step and a primer extension is performed, adding to the 3' end of the ligation product a degenerate sequence 29a complementary to that on each oligonucleotide (which is subsequently removed, for example, by digestion). The resulting product (a population of "tagged adaptors" each with a degenerate sequence 29a at their 3' ends) is then released from the bead or nanoball 15, e.g., by heat denaturation. The tagged adaptors are annealed to a single strand of the long fragment 1 (produced by denaturing the double stranded long fragment); as shown in FIG. 4D, the different degenerate sequences at the ends of various tagged adaptors 29a, 29b anneal to complementary sequences spaced apart along the long fragment 1. As described above, a polymerase is added to extend the tagged adaptor, and the extension product includes a sequence complementary to a region of the long fragment 31a, 31b. The resulting molecules, which include a tagged adaptor joined to a sequence from the long fragment can then be used to create tagged subfragments of the long fragment as described above (FIG. 4A).

(7) Insertion Using Controlled Nick Translation

FIG. 4G illustrates an approach similar to (4), above. Long double-stranded DNA is nicked and then the nicks are opened into short gaps to facilitate the subsequent ligation of adaptor to the 3'-end of the gap. Nicking can be accomplished with by partial digestion with any nicking endonuclease (nickase). One suitable nickase is Nt.CviPII. The recognition site for Nt.CviPII is the short sequence CCD, where D=A, G or T. The gap can be opened either by using the 3'-exo activity of the proofreading polymerase Klenow, which will bind to nicks and degrade the nicked strand in a 3' to 5' direction leaving a short gap in the absence of nucleotide, or by controlled nick translation (CNT), which uses the nick-translating polymerase Pol I and a limited amount of nucleotides to translate the nick a short distance. This reaction leaves a short gap (1-3 bases) instead of a nick.

This nicking approach provides good read coverage per long DNA fragment because it uses both DNA strands. In some embodiments, the processes can be carried out in a gel block (or other polymer block or fill-in at the bottom of a tube or a microtiter plate well), optionally carrying out the enzymatic steps in series. For example, if long DNA fragments and DNBs are entrapped in gel plugs and then controlled nicking is carried out, for example by Vvn, followed by washing out the nickase is performed, one can then do a CNT reaction for 20-100 bases (e.g., about 20 bases) to create a small gap (and further randomize position of nick sites) followed by washing out polymerase. Other ways to create a gap include using Klenow or exonucleases. The resulting product at this stage would be DNA ready for "in-gap" adapter ligation and DNBs still mostly intact. DNA would be fragmented into ~10 kb segments but they would not be able to move significantly in gel plugs. The final step of this in-gel method single tube LFR is a) fragmenting DNBs, creating adapter by hybridization/ligation of components added in solution and b) ligation of such barcoded adapters in the prepared gaps in genomic DNA. This step requires to mix specific nickase for fragmenting DNBs and ligase. The reaction may be stopped by washing out enzymes and or hit kill that would also release DNA from gel plugs. Beads with clonal barcode may be used instead of DNBs in this method. DNBs or beads may be used at distance of 2-40 micrometers, preferably 5-20 um, on average. Long DNA molecules, usually occupying 3D space having about 0.5-2 um$^3$ or more in volume, may be used in concentration creating average distance of 1 to 3 um or even 4-10 um, on average.

Subfragments Series

The methods of (4), (5) and (6) (shown in FIGS. 4A to 4D) result in PCR amplicons that are, effectively, tagged subfragments of the long DNA fragments. This is advantageous if short-read sequencing methods are used. There are a variety of ways to create such a series of fragments.

Figure 4E:
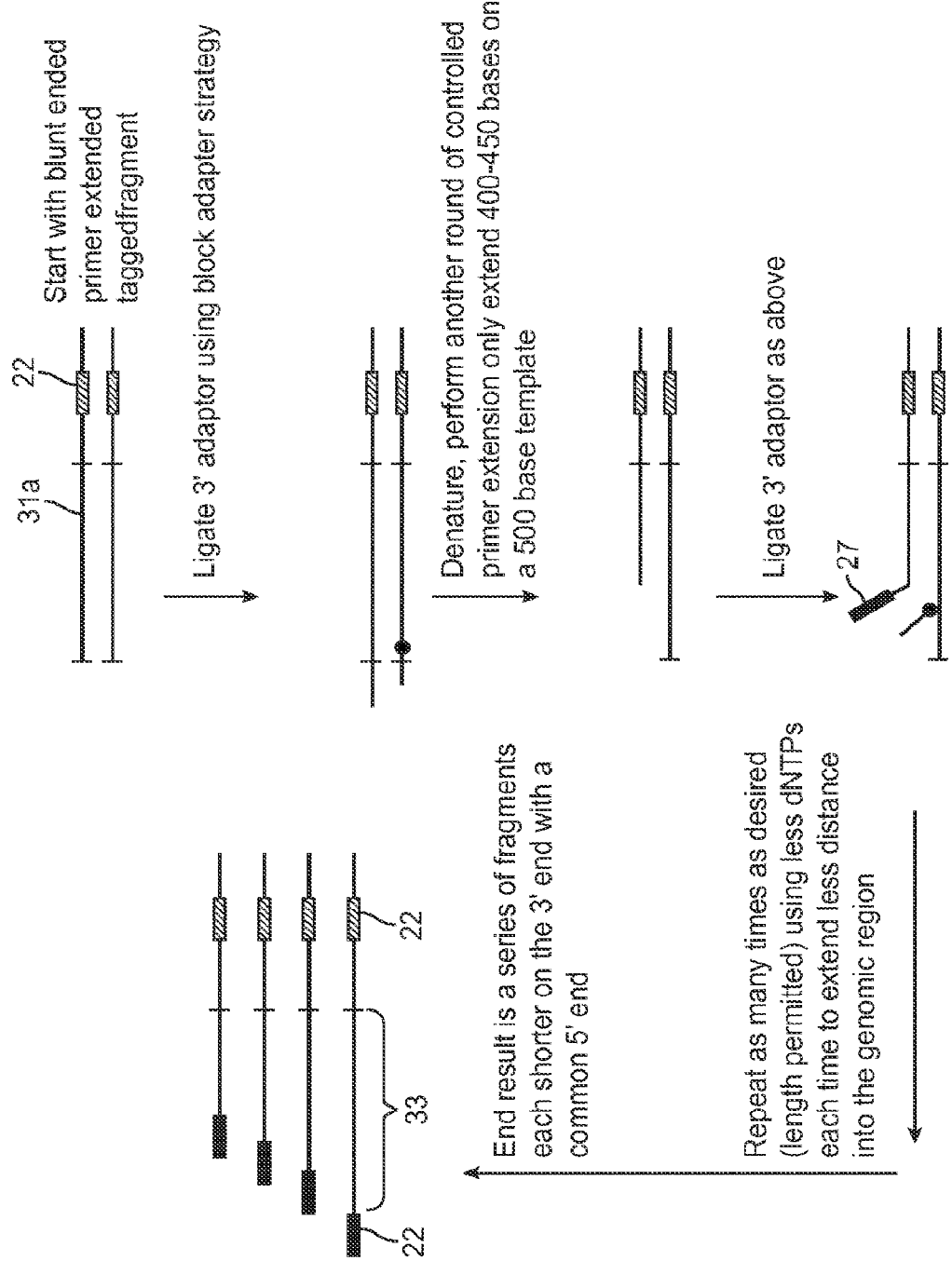
FIGS. 4E and 4F show methods for creating a series of tagged subfragments of with shorter and shorter regions of the long DNA fragments.

For example, it is possible to create a series of such subfragments with shorter and shorter regions of the long DNA fragments as shown in FIG. 4E. This starts with the blunt-ended primer-extended tagged subfragment that results from PCR amplification, comprising a portion 31a of a long fragment joined to a tag sequence 22. A 3' adaptor 27 is ligated to the tagged subfragments. One end of the adaptor includes an overhang; the other end is a blunt end that includes a blocked nucleotide (e.g., a ddNTP). After ligation of the 3' adaptor, the subfragment is denatured and another round of primer extension is performed using controlled nick translation. The primer extension is stopped before completion such that the primer does not extend all the way to the end of the complementary strand. A 3' adaptor 27 is ligated to the end of the extended strand. This process can be repeated as many times as desired with the extent of primer extension varied in order to create a series of fragments 33 having a common 5' end that are shortened on their 3' ends. Details of the blocked adaptor strategy and of controlled nick translation are provided, for example, in U.S. patent application Ser. No. 12/329,365 (published as U.S. 2012-0100534 A1) and Ser. No. 12/573,697 (published as US-2010-0105052-A1).

Figure 4F:
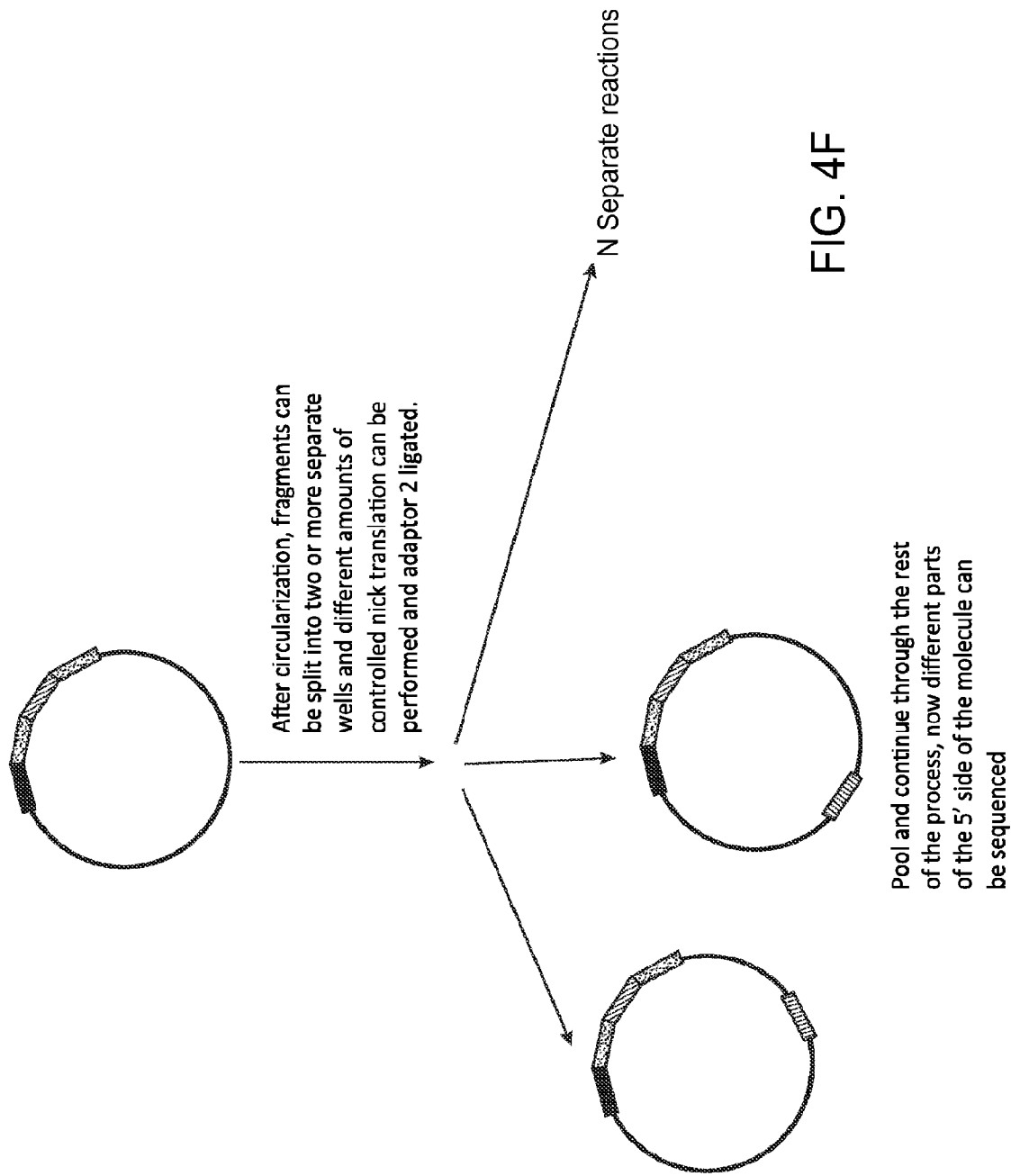

Another approach to creating a series of such subfragments with shorter and shorter regions of the long DNA fragments as shown in FIG. 4F. This approach also uses controlled nick translation. Subfragments are circularized then split into two or more separate wells. Controlled nick translation is performed to a different extent in the various wells in order to create subfragments with a common 5' end that are shortened on their 3' ends to various degrees. The subfragments can then be pooled and the process continued. Another approach uses Exonuclease III, or other exonucleases.

Strategies for Obtaining High Proportion of Long Fragments Labeled with Exactly One Tea Sequence Optimal use of the long fragments occurs when most of them have been tagged. Assembly of reads into full-length sequence or analysis of adjacent regions of the genome is usually easier if, on most or all of the long fragments, there are multiple copies of a single tag sequence that differ from the tag sequence on other long fragments. Thus, after amplification of each of the tagged subfragments, two reads having the same tag sequence would have come from the same long fragment. Sections describing use of excess of DNA fragments or excess of DNA binding capacity on clonal-barcode carries, above, described how to adjust dilutions and ratios of reacting long DNA fragments and introduced clonal tag sequences to optimize tagging.

One strategy for obtaining high proportion of long fragments labeled with exactly one tag sequence involves tethering and other ways of associating particles with single long fragments. There are several ways to attach or tether a single bead or DNA nanoball (DNB) with multiple copies of a particular tag-containing sequence to a single long fragment of a target nucleic acid. For example, a homopolymer sequence (e.g., an A-tail) may be added to the long fragment using terminal transferase or an adaptor with a selected sequence may be ligated to an end or ends of the long fragment. A complementary sequence may be added to the end of or included within the tag-containing sequence or nanoball such that, under selected appropriate conditions, the tag-containing sequence or tag assembly anneals with the corresponding complementary sequence on the long fragment. Preferably, a long fragment can anneal to only one tag-containing sequence or tag assembly.

Various beads used for clonal amplification of adapter-barcode-adapter oligonucleotides can have additional weak temporary DNA binding capacity: e.g. positively charged surface or surface that binds to DNA bases. Different size beads can be used to provide enough barcode copies and also enough surface for binding long DNA fragments. Clonal barcodes and associated adapters (e.g. Ad1-Barcode-Ad2) generated by circle replication as concatemers (DNBs) can be modified by hybridizing a modified oligonucleotide to a segment of an adapter. Alternatives are branched structures that provide sufficient number of positive charge or other chemical groups that provide sufficient binding capacity for long DNA fragments.

Characteristics of Tagged Long Fragments

In one aspect, the invention provides a DNA molecule comprising a genomic sequence (G) and a plurality of discrete introduced sequences (IS), wherein said introduced sequences are not naturally contiguous with the genomic DNA sequence. The DNA molecule is single-stranded or double-stranded. In some embodiments the DNA has a length of at least 2 kb, 5 kb, at least 7.5 kb or at least 10 kb, such as a length in the range 5-20 kb, 7.5-15 kb, or 10-12.5 kb. In some embodiments, the DNA has a length of at least 50 kb, at least 75 kb or at least 100 kb, such as a length in the range 50-200 kb, 75-150 kb, or 100-125 kb. Generally, each fragment comprises at least 5, at least 10, at least 25, or at least 50 introduced sequences wherein each of said introduced sequences has the same sequence or comprises a common subsequence.

The average spacing between introduced sequences is 100 bp, 200 bp, 300 bp, 400 bp, 500 bp, 600 bp, 700 bp, 800 bp, 900 bp, 1000 bp, 1500 bp, 2000 bp, 2500 bp, 3000 bp, 3500 bp, 4000 bp, or 5000 bp. According to another embodiment, the average spacing is between about 100 bp and about 5000 bp, or between about 200 bp and about 4000 bp, or between about 300 bp and about 3000 bp, or between about 300 bp and about 2000 bp, or between about 300 bp and about 1000 bp.

The DNA length, N, is 50-150 kb and the number of introduced sequences, IS, is in the range [(N×1) to (N×4)]. Alternatively, the DNA length, N, is 50-150 kb and the number of introduced sequences, IS, is in the range [(N×2)–(N×10)]. Alternatively, the DNA length, N, is 50-150 kb and the number of introduced sequences, IS, is in the range [(N×1) to (N×0.2)].

In some embodiments, the DNA length. N, is 5-15 kb and the number of introduced sequences, IS, is in the range [(N×1) to (N×4)]. Alternatively, the DNA length, N, is 5-15 kb and the number of introduced sequences, IS, is in the range [(N×2)–(N×10)]. Alternatively, the DNA length, N, Is 5-15 kb and the number of introduced sequences, IS, Is in the range [(N×1) to (N×0.2)].

The genomic DNA sequence may be, for example, from an animal, such as a mammal (e.g., human), a plant, a fungus or bacteria.

The introduced sequences may comprise transposon sequences and/or primer binding sequences.

In one aspect the invention provides a composition comprising a population of DNA molecules as described above. The population may in aggregate represent essentially all (e.g., at least 80%, at least 90%, at least 95%, or at least 99%) genomic sequence of an organism. The composition may further comprise (i) a transposase, (ii) a DNA polymerase, and/or (iii) amplification primers that bind a sequence in the introduced sequence or the complement of a sequence in a the introduced sequence.

In one aspect the invention provides a composition comprising a population of tagged long fragments as described above wherein the population comprises in aggregate at least about $10^4$, at least about $10^5$, at least about $10^6$, or at least about $10^7$ different inserted barcodes.

In one aspect, a majority or essentiality all (e.g., at least 50%, at least 80%, at least 90%, at least 95%, or at least 99%) of the DNA molecules in the population comprise a unique introduced sequence (i.e., an introduced sequence not shared by other molecules). In some cases, the unique introduced sequences share a common subsequence. The common subsequence may be a primer binding sequence.

In some embodiments, more than 10%, more than 20%, more than 30% or more than 50% of the DNA length in a long fragment can be represented in short DNA fragments tagged with the copies of the same barcodes. For example, using a 100 kb long fragment to generate 100 sub-fragments with an average length of 1 kb, would result In 20-50 useful tagged fragments. The other fragments would be lost as untagged or too short or too long.

In some embodiment a substantial number (greater than 25%) or majority (greater than 50%) of long DNA fragments in a composition are tagged with more than one (e.g., two or three) different tags.

Producing Subfragments of Tagged Long Fragments

After tagging, the long fragments of the target nucleic acid are subfragmented to a desired size by amplification (e.g., by PCR, primer extension, RCA), restriction enzyme digestion (e.g., using a rare cutter that has a recognition site within a tag-containing sequence introduced into long fragments), or by other conventional techniques, including enzymatic digestion, shearing, sonication, etc.

Subfragment sizes can vary depending on the source target nucleic acid and the library construction methods used, but for standard whole-genome sequencing such fragments typically range from 50 to 2000 nucleotides in length. In another embodiments, the fragments are 300 to 600 nucleotides in length, 200 to 2000 nucleotides in length, or 1000 to 5000 nucleotides in length. In yet another embodiment, the fragments are 10-100, 50-100, 50-300, 100-200, 200-300, 50400, 100400, 200400, 300-400, 400-500, 400-600, 500-600, 50-1000, 100-1000, 200-1000, 300-1000, 400-1000, 500-1000, 600-1000, 700-1000, 700-900, 700-800, 800-1000, 900-1000, 1500-2000, 1750-2000, and 50-2000 nucleotides in length.

In a further embodiment fragments of a particular size or in a particular range of sizes are isolated. Such methods are well known in the art. For example, gel fractionation can be used to produce a population of fragments of a particular size within a range of base pairs, for example for 500 base pairs+50 base pairs.

Depending on the selection of tagging and post-processing conditions and different sequence read lengths starting with about 5 to about 1,000,000 genome-equivalents of long fragment DNA ensure that the population of long fragments covers the entire genome. Libraries containing nucleic acid templates generated from such a population of overlapping fragments will provide most or all of the sequence of an entire genome.

Characteristics of Subfragments

In one aspect, the invention provides a composition comprising a population of polynucleotides, each comprising (1) sequence corresponding to segment of a genomic DNA; (2) introduced sequences (e.g., clonal barcodes) at one or both termini, wherein the population comprises a plurality of different segments of genomic DNA sequence, and the introduced sequences comprise in aggregate a plurality of different tag or barcode sequences such that some polynucleotides that comprise different genomic DNA segments comprise at least one tag or barcode sequence In common; and (3) the population of polynucleotides comprises at least $10^4$ different barcode sequences, at least $10^5$ different barcode sequences, at least $10^6$ different barcode sequences, or at least $10^7$ different barcode sequences. In some embodiments, the polynucleotide have an average size (in bases or basepairs) in the range of 50-5000, such as 50-100, 100-200, 200-300, 300-500, 500-700, 700-1000, 1000-1500, 1500-2000, 2000-3000, 3000-4000, or 4000-5000. In some embodiments, at least one pair of DNA segments that comprise a tag or barcode in common are adjacent in the genome. In some embodiments, polynucleotides that comprise at least one tag or barcode sequence in common comprise only nonoverlapping genomic DNA segments, where "nonoverlapping" means the segments do not overlap in the genome. Sometimes, the composition comprises a plurality (e.g., at least 10, at least 100, or at least 500) of polynucleotides in one or multiple copies that share the same tag or barcode and are adjacent in the genome. Sometimes, the composition comprises a plurality (e.g., at least 10, at least 100, or at least 500) of polynucleotide pairs that share the same tag or barcode and are adjacent in the target (e.g., genome) sequence. The tag sequences may comprise bar codes in combination with transposon sequences and/or primer binding sites. The introduced sequence is not naturally contiguous with the genomic DNA segment.

The genomic DNA may be from a plant, animal (e.g., a mammal such as a human), bacteria or fungus. For bacteria can be a mixture (meta-genomes, to allow assembly of strains and species genomes without culturing strain by strain) or isolated strains or species. The polynucleotides may be amplicons.

Amplification

Before or after any step outlined herein, an amplification step can be used to ensure that enough of the nucleic acid is available for subsequent steps.

According to one embodiment of the invention, methods are provided for sequencing small quantities of complex nucleic acids, including those of higher organisms, in which such complex nucleic acids are amplified in order to produce sufficient nucleic acids for sequencing by the methods described herein. A single human cell includes approximately 6.6 picograms (pg) of genomic DNA. Sequencing of complex nucleic acids of a higher organism can be accomplished using 1 pg, 5 pg, 10 pg, 30 pg, 50 pg, 100 pg, or 1 ng or more of a complex nucleic acid as the starting material, which is amplified by any nucleic acid amplification method known in the art, to produce, for example, 200 ng, 400 ng, 600 ng, 800 ng, 1 pg, 2 pg, 3 pg, 4 pg, 5 pg, 10 pg or greater quantities of the complex nucleic acid. We also disclose nucleic acid amplification protocols that minimize GC bias. However, the need for amplification and subsequent GC bias can be reduced further simply by isolating one cell or a small number of cells, culturing them for a sufficient time under suitable culture conditions known in the art, and using progeny of the starting cell or cells for sequencing.

Such amplification methods include without limitation: multiple displacement amplification (MDA), polymerase chain reaction (PCR), ligation chain reaction (sometimes referred to as oligonucleotide ligase amplification OLA), cycling probe technology (CPT), strand displacement assay (SDA), transcription mediated amplification (TMA), nucleic acid sequence based amplification (NASBA), rolling circle amplification (RCA) (for circularized fragments), and invasive cleavage technology.

Amplification can be performed after fragmenting or before or after any step outlined herein.

Whole Genome Amplification Protocols

Particular amplification protocols that have been used during the development of this invention include the following.

A first amplification protocol is transposon mediated insertion of adapters for long PCR amplification. To maximize coverage of the genome using short read sequencing, we amplify relatively large fragments of the genome. This allows for shorter overlapping fragments to be generated, which can then be sequenced. Transposons are inserted at a frequency of 3-20 kb in long genomic DNA. Single primer or two primer PCR can then be done for a small number of cycles to generate >10 fold amplification. In one version of this process, only one round of long PCR is performed followed by fragmenting to overlapping ~300 bp to 1.5 kilobases by incorporation of uracil during amplification (CoRE), ultrasonic fragmentation, nuclease digestion, transposon fragmenting, or other suitable method In another version of this process, longer PCR products ~10 kb in size are first generated and <100 fold amplification is performed. A second round of transposon insertion is performed at a frequency of ~3 kb. Additional rounds of PCR amplification are performed to generated >1000 fold amplification. Now fragmentation as described above can be performed.

A second protocol is to insert adaptors into gaps generated in the long fragments. Nicks are first introduced at a frequency of 3-20 kb. The nicks are opened to gaps of >1 bp using nucleases or polymerases in the absence of nucleotides in the buffer. Adapters are then ligated into the 3'-OH and the 5' $PO_4$ of the gap. On the 3' side no hybridization with bases in the gap is necessary. On the 5' side an adapter with N6 on the 3' end will be necessary to first hybridize adjacent to the 5' $PO_4$ prior to ligation. Once ligation is complete, 1 or 2 primer PCR can be performed. Long PCR primers are again fragmented into smaller overlapping 300-1.5 kb fragments as above.

MDA Amplification Protocol with Reduced GC Bias

In one aspect, the present invention provides methods of nucleic acid amplification in which the nucleic acid is faithfully amplified. e.g., approximately 30,000-fold depending on the amount of starting DNA.

According to one embodiment of MT methods of the present invention, MT begins with treatment of genomic nucleic acids, usually genomic DNA, with a 5' exonuclease to create 3' single-stranded overhangs. Such single stranded overhangs serve as MDA initiation sites. Use of the exonuclease also eliminates the need for a heat or alkaline denaturation step prior to amplification without introducing bias into the population of fragments. In another embodiment, alkaline denaturation is combined with the 5' exonuclease treatment, which results in a reduction in bias that is greater than what is seen with either treatment alone. The fragments are then amplified.

In one embodiment, a phi29-based multiple displacement amplification (MDA) is used. Numerous studies have examined the range of unwanted amplification biases, background product formation, and chimeric artifacts introduced via phi29 based MDA, but many of these short comings have occurred under extreme conditions of amplification (greater than 1 million fold). Commonly, MT employs a substantially lower level of amplification and starts with long DNA fragments (e.g., ~100 kb), resulting in efficient MDA and a more acceptable level of amplification biases and other amplification-related problems.

We have developed an improved MDA protocol to overcome problems associated with MDA that uses various additives (e.g., DNA modifying enzymes, sugars, and/or chemicals like DMSO), and/or different components of the reaction conditions for MDA are reduced, increased or substituted to further improve the protocol. To minimize chimeras, reagents can also be included to reduce the availability of the displaced single stranded DNA from acting as an incorrect template for the extending DNA strand, which is a common mechanism for chimera formation. A major source of coverage bias introduced by MDA is caused by differences in amplification between GC-rich verses AT-rich regions. This can be corrected by using different reagents In the MDA reaction and/or by adjusting the primer concentration to create an environment for even priming across all % GC regions of the genome. In some embodiments, random hexamers are used in priming MDA. In other embodiments, other primer designs are utilized to reduce bias. In further embodiments, use of 5' exonuclease before or during MDA can help initiate low-bias successful priming, particularly with longer (i.e., 200 kb to 1 Mb) fragments that are useful for sequencing regions characterized by long segmental duplication (i.e., In some cancer cells) and complex repeats.

In some embodiments, improved, more efficient fragmentation and ligation steps are used that reduce the number of rounds of MDA amplification required for preparing samples by as much as 10,000 fold, which further reduces bias and chimera formation resulting from MDA.

In some embodiments, the MDA reaction is designed to introduce uracils into the amplification products in preparation for CoRE fragmentation. In some embodiments, a standard MDA reaction utilizing random hexamers is used to amplify the fragments in each well; alternatively, random 8-mer primers can be used to reduce amplification bias (e.g., GC-bias) in the population of fragments. In further embodiments, several different enzymes can also be added to the MDA reaction to reduce the bias of the amplification. For example, low concentrations of non-processive 5' exonucleases and/or single-stranded binding proteins can be used to create binding sites for the 8-mers. Chemical agents such as betaine, DMSO, and trehalose can also be used to reduce bias.

After amplification of the nucleic acids in a sample, the amplification products may optionally be fragmented. In some embodiments the CoRE method is used to further fragment the fragments following amplification. In such embodiments, MDA amplification of fragments is designed to incorporate uracils into the MDA products. The MDA product is then treated with a mix of Uracil DNA glycosylase (UDG), DNA glycosylase-lyase Endonuclease VIII, and T4 polynucleotide kinase to excise the uracil bases and create single base gaps with functional 5' phosphate and 3' hydroxyl groups. Nick translation through use of a polymerase such as Taq polymerase results in double stranded blunt-end breaks, resulting in ligatable fragments of a size range dependent on the concentration of dUTP added in the MDA reaction. In some embodiments, the CoRE method used involves removing uracils by polymerization and strand displacement by phi29. The fragmenting of the MDA products can also be achieved via sonication or enzymatic treatment. Enzymatic treatment that could be used in this embodiment includes without limitation DNase I, T7 endonuclease I, micrococcal nuclease, and the like.

Following fragmentation of the MDA products, the ends of the resultant fragments may be repaired. Many fragmentation techniques can result in termini with overhanging ends and termini with functional groups that are not useful in later ligation reactions, such as 3' and 5' hydroxyl groups and/or 3' and 5' phosphate groups. It may be useful to have fragments that are repaired to have blunt ends. It may also be desirable to modify the termini to add or remove phosphate and hydroxyl groups to prevent "polymerization" of the target sequences. For example, a phosphatase can be used to eliminate phosphate groups, such that all ends contain hydroxyl groups. Each end can then be selectively altered to allow ligation between the desired components. One end of the fragments can then be "activated" by treatment with alkaline phosphatase.

Nucleic Acid Sequencing

MT methods described herein can be used as a preprocessing step for sequencing diploid genomes using any sequencing method known in the art, including for example without limitation, polymerase-based sequencing-by-synthesis (e.g., HiSeq 2500 system, Illumina, San Diego, Calif.), ligation-based sequencing (e.g., SOLiD 5500, Life Technologies Corporation, Carlsbad, Calif.), ion semiconductor sequencing (e.g., Ion PGM or Ion Proton sequencers, Life Technologies Corporation. Carlsbad, Calif.), zero-mode waveguides (e.g., PacBio RS sequencer, Pacific Biosciences, Menlo Park, Calif.), nanopore sequencing (e.g., Oxford Nanopore Technologies Ltd., Oxford, United Kingdom), pyrosequencing (e.g., 454 Life Sciences, Branford, Conn.), or other sequencing technologies. Some of these sequencing technologies are short-read technologies, but others produce longer reads. e.g., the GS FLX+ (454 Life Sciences; up to 1000 bp), PacBio RS (Pacific Biosciences; approximately 1000 bp) and nanopore sequencing (Oxford Nanopore Technologies Ltd.; 100 kb). For haplotype phasing, longer reads are advantageous, requiring much less computation, although they tend to have a higher error rate and errors in such long reads may need to be identified and corrected according to methods set forth herein before haplotype phasing.

According to one embodiment, sequencing is performed using combinatorial probe-anchor ligation (cPAL) as described, for example, in U.S. Patent Application Publications 2010/0105052; US2007099208; US 2009/0264299; US 2009/0155781; US 2009/0005252; US 2009/0011943; US 2009-0118488; US 2007/0099208; US 2008/0234136; US 2009/0137404; US 2009/0137414; US 2007/0072208; US 201010081128; US 2008/0318796; US 2009/0143235; US 2008/0213771; US 2008/0171331; US 2007/0037152; US 2009/0005259; US 2009/0036316; US 2009/0011416; US 2009/0075343; US 2009/0111705; US 2009/0111706; US 2009/0203551; US 2009/0105961; US 2008/0221832; US 2009/0318304; US 2009/0111115; US 2009/0176652; US 2009/0311691; US 2009/0176234; US 2009/0263802; US 2011/0004413; and Ser. No. 12/329,365; published international patent application numbers WO2007120208, WO2006073504, and WO2007133831, and U.S. patent application Ser. No. 13/448,279 (published as US 20140051588), Ser. No. 13/447,087, (published as 20130124100) all of which are incorporated herein by reference in their entirety for all purposes.

Exemplary methods for calling variations In a polynucleotide sequence compared to a reference polynucleotide sequence and for polynucleotide sequence assembly (or reassembly), for example, are provided in U.S. patent publication No. 2011-0004413. (application Ser. No. 12/770, 089) which is incorporated herein by reference in its entirety for all purposes. See also Drmanac et al., *Science* 327, 78-81, 2010. Also incorporated by references in their entirety and for all purposes are copending related application No. 61/623,876, entitled "Identification Of DNA Fragments And Structural Variations"; application Ser. No. 13/649,966, published as US Pat Pub. 2013-0096841; and application Ser. No. 13/447,087, entitled "Processing and Analysis of Complex Nucleic Acid Sequence Data" published as US Pat. Pub. 2013/0124100.

By sequencing 50% of each ~1 kb fragment, ~1× sequence coverage would be generated for each genomic fragment because tagged fragments are generated from both strands of dsDNA. If one sequences 25% (½ read coverage per fragment), one would observe the linkage of two regions in 25% of fragments. For the same read budget we can increase the number of fragments two-fold and have only two-fold reduction in the observed linkages. For 25% read (125 bases form each end of 1 kb fragment) and 36 starting cells one will observe nine linkages instead of ~18 linkages for 18 cells if one reads 50% of DNA (250 bases from each end of a ~1 kb fragment. If only ~60 bases can be read from each fragment, it is better to use 300-500 bp fragments that still make very useful mate-pairs.

If sequencing a fraction of DNA from each ~1 kb fragment, more initial fragments are needed. For example, if one sequences one-half, 4× more fragments are required.

Complexity Reduction

In a further aspect, MT techniques of the invention reduce the complexity of DNA to be sequenced to focus on sequence of interests such as a targeted panel of genes for different diseases, exome or rare bacterial strains. Complexity reduction and haplotype separation in >100 kb long DNA can be helpful in more efficiently and cost effective sequence assembly and detection of sequence variations in human and other diploid and polyploid genomes or mixtures of bacterial and other genomes (metagenomes). One way of complexity reduction of tagged DNA fragments is to use capture oligonucleotides for genomic sequences of interest e.g. coding sequences (e.g. exome selection for obtaining "phased" exome variants).

DNA fragments of interest can be enriched by: (a) providing a mixture of DNA fragments tagged by plurality of barcodes, (b) capturing DNA fragments using oligonucleotides complementary at least in part to the barcode sequences of interest, (c) discarding non-captured DNA preferentially having no barcode matching capturing oligonucleotides, thus enriching DNA fragments of interest. The mixture may comprise DNA fragments from more than 30, 100, or 1000 bacterial strains or species in variable representation. A barcode may be used to tag DNA from one or a few bacterial cells. More than 10, 30, 50, 100 or 300 different capture oligonucleotides may be used, each specific for one barcode. In both approaches instead of positive selection, a negative selection can be used to remove unwanted, usually frequent sequences such as Alu repeats In human genome or frequent bacteria in microbiome.

Definitions

As used herein, a "fragment" or subfragment of a target nucleic acid, such as a fragment of genomic DNA, fragment of chromosomal DNA, a long fragment, or a subfragment (of a long fragment, of a target DNA, etc.) refers to the relationship of the sequences, rather than necessarily to a direct physical derivation. A "fragment" of a longer sequence (e.g., a "fragment of a target nucleic acid molecule" or "a subfragment of a tagged long fragment") comprises the sequence of a portion of the longer sequence, or alternatively, comprises the exact complement of a sequence of a portion of the longer sequence, without regard to how the fragment is produced. For example, a "subfragment" of a target nucleic acid or of a long fragment can be produced by amplification or replication of a portion of the target nucleic acid, resulting in a new molecule comprising a sequence that is the same as, or exactly complementary to, the target nucleic acid sequence. In other example, a "subfragment" of a target nucleic acid or of a long fragment can be produced by physical or enzymatic fragmentation of the target nucleic acid or long fragment.

The term "long fragment" is used in this description to refer to a starting nucleic acid polymer that is used in a protocol of this invention for tagging, sequencing, analysis, or further processing. The term does not require that the nucleic acid be obtained from any particular source or by any particular process. The nucleic acid can be any length and have any characteristics that are compatible with the protocol being referred to. It may previously have been amplified, fragmented, recombined, or otherwise processed before the initial step of the protocol being referred to. In some of the illustrations provided in this disclosure, a starting "long fragment" is between about 3 and 20 kb, in other is 10 to 100 kb or 30-300 kb or majority or most are longer than 10 or longer than 20 kb or longer than 30 kb or 50 kb.

As used herein, nucleic acid "amplification" refers to methods in which a polynucleotide copies are produced through cycles of polymerization or ligation, at a geometric or expediential rate, as distinguished from template replication, in which a single copy of a template is made, or in which one or more copies of the template are obtained by RCR.

A fragment of a target nucleic acid to be sequenced and analyzed is sometimes referred to as an "initial fragment". The term is used only to indicate that a fragment having the specified characteristics is a product used early in a particular protocol.

As used herein "inserting," "introducing," and "incorporating" are not limited to physically incorporating one polynucleotide (e.g., a bar-code containing oligonucleotide) into another polynucleotide (e.g. a long DNA). For example, as described hereinabove, a barcode sequence may be introduced into a long DNA fragment by replicating all or part of the long DNA fragment sequence along with interspersed tag sequences. (See, e.g., FIG. 2A.) A barcode sequence may be introduced into a long DNA fragment by physically transposing a barcode sequence into the long DNA molecule. (See, e.g., FIG. 1A.)

As used herein, "interspersed" has its normal meaning in the art. For example, a tagged long fragment containing "target nucleic acid sequence and multiple interspersed tag sequences," is a polynucleotide that comprises a target nucleic acid sequence, such as a genomic sequence, interrupted by multiple tag sequences (e.g., multiple copies of a tag sequence) such that tag sequences lie between target sequences that are contiguous in the target nucleic acid. As discussed above, the average spacing between adjacent introduced tag sequences may be, for example, 100 bp, 200 bp, 300 bp, 400 bp, 500 bp, 600 bp, 700 bp, 800 bp, 900 bp, 1000 bp, 1500 bp, 2000 bp, 2500 bp, 3000 bp, 3500 bp, 4000 bp, or 5000 bp.

The term "transposon", as used herein, refers to a nucleic acid segment that is recognized by a transposase or an integrase enzyme and is capable of transposition.

The term "transposase" as used herein refers to an enzyme that is a component of a functional nucleic acid-protein complex capable of transposition and that mediates transposition. The term "transposase" also refers to integrases from retrotransposons or of retroviral origin.

The expression "transposition reaction" used herein refers to a reaction wherein a transposon inserts into a target nucleic acid. Primary components in a transposition reaction are a transposon and a transposase or an intagrase enzyme.

The term "transposon end sequence" or "transposon ends," as used herein refers to the nucleotide sequences at the distal ends of a transposon. The transposon end sequences are responsible for identifying the transposon for transposition; they are the DNA sequences the transpose enzyme requires in order to form transpososome complex and to perform transposition reaction. A transposable DNA may comprise only one transposon end sequence or more than one transposon end sequence. The transposon end sequence in the transposable DNA sequence is thus not linked to another transposon end sequence by nucleotide sequence, i.e., the transposable DNA contains only one transposase binding sequence. Thus, the transposable DNA comprises a "transposon end" (see. e.g., Savilahti et al., EMBO J. 14:4893-4903, 1995).

The term "transposase binding sequence" or "transposase binding site" as used herein refers to the nucleotide sequences that are always within the transposon end sequence to which a transposase specifically binds when mediating transposition. The transposase binding sequence may comprise more than one site for the binding of transposase subunits.

The term "transposon joining strand" or "joining end" as used herein means the end of that strand of the double-stranded transposon DNA, which is joined by the transposase to the target DNA at the insertion site.

Transposon complexes form between a transposase enzyme and a fragment of double stranded DNA that contains a specific binding sequence for the enzyme, termed a "transposon end". The sequence of the transposon binding site can be modified with other bases, at certain positions, without affecting the ability for transposon complex to form a stable structure that can efficiently transpose into target DNA. By manipulating the sequence of the transposon end, the method provided properties to the fragmented target DNA that can be utilized in downstream applications, particularly when using the method for library preparation before sequencing.

The term "adaptor" or "adaptor tail" as used herein refers to a non-target nucleic acid component, generally DNA, that provides a means of addressing a nucleic acid fragment to which it is joined. For example, in embodiments, an adaptor comprises a nucleotide sequence that permits identification, recognition, and/or molecular or biochemical manipulation of the DNA to which the adaptor is attached (e.g., by providing a site for annealing an oligonucleotide, such as a primer for extension by a DNA polymerase, or an oligonucleotide for capture or for a ligation reaction).

The term "particle" as used in this disclosure refers to a delivery system for multiple copies of a small oligonucleotide, such as a transposon or primer. The oligonucleotide is attached to or incorporated into the particle in a manner that makes it releasable for the purposes of participating in a reaction or recombination—for example, using a restriction nuclease. Non-limiting examples include DNB (nanoballs), which are concatemers of an oligonucleotide, and nanobeads to which multiple copies of an oligonucleotide is attached. The oligonucleotide copies on the particle typically comprises a tag sequence that differs from tag sequences on other particles. When this disclosure refers to a concatemer or bead participating in a reaction, unless otherwise stated or required, the description should be considered to refer broadly to particles of any nature that have releasable oligonucleotides and are compatible with the protocols outlined—exemplified but not limited to the type of particle used for purposes of illustration.

As used herein, the term "complex nucleic acid" refers to large populations of nonidentical nucleic acids or polynucleotides. In certain embodiments, the target nucleic acid is genomic DNA; exome DNA (a subset of whole genomic DNA enriched for transcribed sequences which contains the set of exons in a genome); a transcriptome (i.e., the set of all mRNA transcripts produced in a cell or population of cells, or cDNA produced from such mRNA); a methylome (i.e., the population of methylated sites and the pattern of methylation in a genome); an exome (i.e., protein-coding regions of a genome selected by an exon capture or enrichment method; a microbiome; a mixture of genomes of different organisms: a mixture of genomes of different cell types of an organism; and other complex nucleic acid mixtures comprising large numbers of different nucleic acid molecules (examples include, without limitation, a microbiome, a xenograft, a solid tumor biopsy comprising both normal and tumor cells, etc.), including subsets of the aforementioned types of complex nucleic acids. In one embodiment, such a complex nucleic acid has a complete sequence comprising at least one gigabase (Gb) (a diploid human genome comprises approximately 6 Gb of sequence).

Non-limiting examples of complex nucleic acids include "circulating nucleic acids" (CNA), which are nucleic acids circulating in human blood or other body fluids, including but not limited to lymphatic fluid, liquor, ascites, milk, urine, stool and bronchial lavage, for example, and can be distinguished as either cell-free (CF) or cell-associated nucleic acids (reviewed in Pinzani et al., Methods 50:302-307, 2010), e.g., circulating fetal cells in the bloodstream of a expecting mother (see, e.g., Kavanagh et al., J. Chromatol. B 878:1905-1911, 2010) or circulating tumor cells (CTC) from the bloodstream of a cancer patient (see, e.g., Allard et al., Clin Cancer Res. 10:6897-6904, 2004). Another example is genomic DNA from a single cell or a small number of cells, such as, for example, from biopsies (e.g., fetal cells biopsied from the trophectoderm of a blastocyst; cancer cells from needle aspiration of a solid tumor, etc.). Another example is pathogens, e.g., bacteria cells, virus, or other pathogens. In a tissue, in blood or other body fluids, etc.

As used herein, the term "target nucleic acid" (or polynucleotide) or "nucleic acid of interest" refers to any nucleic acid (or polynucleotide) suitable for processing and sequencing by the methods described herein. The nucleic acid may be single stranded or double stranded and may include DNA, RNA, or other known nucleic acids. The target nucleic acids may be those of any organism, including but not limited to viruses, bacteria, yeast, plants, fish, reptiles, amphibians, birds, and mammals (including, without limitation, mice, rats, dogs, cats, goats, sheep, cattle, horses, pigs, rabbits, monkeys and other non-human primates, and humans). A target nucleic acid may be obtained from an individual or from a multiple individuals (i.e., a population). A sample from which the nucleic acid is obtained may contain a nucleic acids from a mixture of cells or even organisms, such as: a human saliva sample that includes human cells and bacterial cells; a mouse xenograft that includes mouse cells and cells from a transplanted human tumor; etc.

Target nucleic acids may be unamplified or they may be amplified by any suitable nucleic acid amplification method known in the art. Target nucleic acids may be purified according to methods known in the art to remove cellular and subcellular contaminants (lipids, proteins, carbohydrates, nucleic acids other than those to be sequenced, etc.), or they may be unpurified, i.e., include at least some cellular and subcellular contaminants, including without limitation intact cells that are disrupted to release their nucleic acids for processing and sequencing. Target nucleic acids can be obtained from any suitable sample using methods known in the art. Such samples include but are not limited to: tissues, isolated cells or cell cultures, bodily fluids (including, but not limited to, blood, urine, serum, lymph, saliva, anal and vaginal secretions, perspiration and semen); air, agricultural, water and soil samples, etc.

High coverage in shotgun sequencing is desired because it can overcome errors in base calling and assembly. As used herein, for any given position in an assembled sequence, the term "sequence coverage redundancy," "sequence coverage" or simply "coverage" means the number of reads representing that position. It can be calculated from the length of the original genome (G), the number of reads (N), and the average read length (L) as N×L/G. Coverage also can be calculated directly by making a tally of the bases for each reference position. For a whole-genome sequence, coverage is expressed as an average for all bases in the assembled sequence. Sequence coverage is the average number of times a base is read (as described above). It is often expressed as "fold coverage," for example, as in "40-fold (or 40×) coverage," meaning that each base in the final assembled sequence is represented on an average of 40 reads.

As used herein, term "call rate" means a comparison of the percent of bases of the complex nucleic acid that are fully called, commonly with reference to a suitable reference sequence such as, for example, a reference genome. Thus, for a whole human genome, the "genome call rate" (or simply "call rate") is the percent of the bases of the human genome that are fully called with reference to a whole human genome reference. An "exome call rate" is the percent of the bases of the exome that are fully called with reference to an exome reference. An exome sequence may be obtained by sequencing portions of a genome that have been enriched by various known methods that selectively capture genomic regions of interest from a DNA sample prior to sequencing. Alternatively, an exome sequence may be obtained by sequencing a whole human genome, which includes exome sequences. Thus, a whole human genome sequence may have both a "genome call rate" and an "exome call rate." There is also a "raw read call rate" that reflects the number of bases that get an A/C/G/T designation as opposed to the total number of attempted bases. (Occasionally, the term "coverage" Is used In place of "call rate," but the meaning will be apparent from the context).

As used herein, the term "haplotype" means a combination of alleles at adjacent locations (loci) on the chromosome that are transmitted together or, alternatively, a set of sequence variants on a single chromosome of a chromosome pair that are statistically associated. Every human individual has two sets of chromosomes, one paternal and the other maternal. Usually DNA sequencing results only in genotypic information, the sequence of unordered alleles along a segment of DNA. Inferring the haplotypes for a genotype separates the alleles in each unordered pair into two separate sequences, each called a haplotype. Haplotype information is necessary for many different types of genetic analysis, including disease association studies and making inference on population ancestries.

As used herein, the term "phasing" (or resolution) means sorting sequence data into the two sets of parental chromosomes or haplotypes. Haplotype phasing refers to the problem of receiving as input a set of genotypes for one individual or a population, i.e., more than one individual, and outputting a pair of haplotypes for each individual, one being paternal and the other maternal. Phasing can involve resolving sequence data over a region of a genome, or as little as two sequence variants In a read or contig, which may be referred to as local phasing, or microphasing. It can also involve phasing of longer contigs, generally including greater than about ten sequence variants, or even a whole genome sequence, which may be referred to as "universal phasing." Optionally, phasing sequence variants takes place during genome assembly.

As used herein, the term "transposon" or "transposable element" means a DNA sequence that can change its position within the genome. In a classic transposition reaction, a transposase catalyzes the random insertion of excised transposons into DNA targets. During cut-and-paste transposition, a transposase makes random, staggered double-stranded breaks in the target DNA and covalently attaches the 3' end of the transferred transposon strand to the 5' end of the target DNA. The transposase/transposon complex inserts an arbitrary DNA sequence at the point of insertion of the transposon into the target nucleic acid. Transposons that insert randomly into the target nucleic acid sequence are preferred. Several transposons have been described and use in in vitro transposition systems. For example, in the Nextera™ technology (Nature Methods 6, November 2009; Epicentre Biotechnologies, Madison, Wis.) The entire complex is not necessary for insertion; free transposon ends are sufficient for integration. When free transposon ends are used, the target DNA is fragmented and the transferred strand of the transposon end oligonucleotide is covalently attached to the 5' end of the target fragment. The transposon ends can be modified by addition of desired sequences, such as PCR primer binding sites, bar codes/tags, etc. The size distribution of the fragments can be controlled by changing the amounts of transposase and transposon ends. Exploiting transposon ends with appended sequences results In DNA libraries that can be used In high-throughput sequencing. Transposon ends may vary in length but are typically 9-40 bases long. Pairs of transposon ends may be inverted complements of each other (i.e., the transposon ends may be inverted terminal repeats).

As used herein, the term "hairpin" (also known as a stem-loop) has its normal meaning in the art and refers to a nucleic acid confirmation in which two regions of the same strand, usually complementary in nucleotide sequence when read in opposite directions, base-pair to form a double helix that ends In an unpaired loop This disclosure from time to time refers to particular features of the invention as "embodiments". The reader is advised that features referred to in this manner may be put together in any combination that is operable, and that various combinations of such features fall within the scope of the invention.

Use of Microdroplets and Emulsions

In some embodiments, the methods of the present invention are performed in emulsion or microfluidic devices.

A reduction of volumes down to picoliter levels can achieve an even greater reduction in reagent and computational costs. In some embodiments, this level of cost reduction is accomplished through the combination of the MT process with emulsion or microfluidic-type devices. The ability to perform all enzymatic steps in the same reaction without DNA purification facilitates the ability to miniaturize and automate this process and results in adaptability to a wide variety of platforms and sample preparation methods.

Recent studies have also suggested an improvement in GC bias after amplification (e.g., by MDA) and a reduction in background amplification by decreasing the reaction volumes down to nanoliter size.

There are currently several types of microfluidics devices (e.g., devices sold by Advanced Liquid Logic, Morrisville, N.C.) or pico/nano-droplet (e.g., RainDance Technologies, Lexington, Mass.) that have pico-/nano-drop making, fusing (3000/second) and collecting functions and could be used in such embodiments of MT.

Amplifying

According to one embodiment, the MT process begins with a short treatment of genomic DNA with a 5' exonuclease to create 3' single-stranded overhangs that serve as MDA initiation sites. The use of the exonuclease eliminates the need for a heat or alkaline denaturation step prior to amplification without introducing bias into the population of fragments. Alkaline denaturation can be combined with the 5' exonuclease treatment, which results in a further reduction in bias. The fragments are amplified, e.g., using an MDA method. In certain embodiments, the MDA reaction is a modified phi29 polymerase-based amplification reaction, although another known amplification method can be used.

In some embodiments, the MDA reaction is designed to introduce uracils into the amplification products. In some embodiments, a standard MDA reaction utilizing random hexamers is used to amplify the fragments in each well. In many embodiments, rather than the random hexamers, random 8-mer primers are used to reduce amplification bias in the population of fragments. In further embodiments, several different enzymes can also be added to the MDA reaction to reduce the bias of the amplification. For example, low concentrations of non-processive 5' exonucleases and/or single-stranded binding proteins can be used to create binding sites for the 8-mers. Chemical agents such as betaine, DMSO, and trehalose can also be used to reduce bias through similar mechanisms.

Fragmentation

According to one embodiment, after DNA amplification of DNA, the amplification product, or amplicons, is subjected to a round of fragmentation. In some embodiments the CoRE method is used to further fragment the fragments in each well following amplification. In order to use the CoRE method, the MDA reaction used to amplify the fragments in each well is designed to incorporate uracils into the MDA products. The fragmenting of the MDA products can also be achieved via sonication or enzymatic treatment.

If a CoRE method is used to fragment the MDA products, amplified DNA is treated with a mix of uracil DNA glycosylase (UDG), DNA glycosylase-lyase endonuclease VIII, and T4 polynucleotide kinase to excise the uracil bases and create single base gaps with functional 5' phosphate and 3' hydroxyl groups. Nick translation through use of a polymerase such as Taq polymerase results in double-stranded blunt end breaks, resulting in ligatable fragments of a size range dependent on the concentration of dUTP added In the MDA reaction. In some embodiments, the CoRE method used involves removing uracils by polymerization and strand displacement by phi29.

Following fragmentation of the MDA products, the ends of the resultant fragments can be repaired. Such repairs can be necessary, because many fragmentation techniques can result in termini with overhanging ends and termini with functional groups that are not useful in later ligation reactions, such as 3' and 5' hydroxyl groups and/or 3' and 5' phosphate groups. In many aspects of the present invention, it is useful to have fragments that are repaired to have blunt ends, and in some cases, it can be desirable to alter the chemistry of the termini such that the correct orientation of phosphate and hydroxyl groups is not present, thus preventing "polymerization" of the target sequences. The control over the chemistry of the termini can be provided using methods known in the art. For example, in some circumstances, the use of phosphatase eliminates all the phosphate groups, such that all ends contain hydroxyl groups. Each end can then be selectively altered to allow ligation between the desired components. One end of the fragments can then be "activated", In some embodiments by treatment with alkaline phosphatase.

MT Using One of a Small Number of Cells as the Source of Complex Nucleic Acids

According to one embodiment, an MT method is used to analyze the genome of an individual cell or a small number of cells (or a similar number of nuclei isolated from cells). The process for isolating DNA in this case is similar to the methods described above, but may occur in a smaller volume.

As discussed above, isolating long fragments of genomic nucleic acid from a cell can be accomplished by a number of different methods. In one embodiment, cells are lysed and the intact nucleic are pelleted with a gentle centrifugation step. The genomic DNA is then released through proteinase K and RNase digestion for several hours. The material can then in some embodiments be treated to lower the concentration of remaining cellular waste—such treatments are well known in the art and can include without limitation dialysis for a period of time (e.g., from 2-16 hours) and/or dilution. Since such methods of isolating the nucleic acid does not involve many disruptive processes (such as ethanol precipitation, centrifugation, and vortexing), the genomic nucleic acid remains largely intact, yielding a majority of fragments that have lengths in excess of 150 kilobases. In some embodiments, the fragments are from about 100 to about 750 kilobases in lengths. In further embodiments, the fragments are from about 150 to about 600, about 200 to about 500, about 250 to about 400, and about 300 to about 350 kilobases in length.

Once isolated, the genomic DNA can be carefully fragmented to avoid loss of material, particularly to avoid loss of sequence from the ends of each fragment, since loss of such material will result In gaps in the final genome assembly. In some cases, sequence loss is avoided through use of an infrequent nicking enzyme, which creates starting sites for a polymerase, such as phi29 polymerase, at distances of approximately 100 kb from each other. As the polymerase creates the new DNA strand, it displaces the old strand, with the end result being that there are overlapping sequences near the sites of polymerase initiation, resulting In very few deletions of sequence.

In some embodiments, a controlled use of a 5' exonuclease (either before or during the MDA reaction) can promote multiple replications of the original DNA from the single cell and thus minimize propagation of early errors through copying of copies.

In one aspect, methods of the present invention produce quality genomic data from single cells. Assuming no loss of DNA, there is a benefit to starting with a low number of cells (10 or less) instead of using an equivalent amount of DNA from a large preparation. Starting with less than 10 cells ensures uniform coverage in long fragments of any given region of the genome. Starting with five or fewer cells allows four times or greater coverage per each 100 kb DNA fragment without increasing the total number of reads above 120 Gb (20 times coverage of a 6 Gb diploid genome). However, a large number of longer DNA fragments (100 kb or longer) are even more beneficial for sequencing from a few cells, because for any given sequence there are only as many overlapping fragments as the number of starting cells and the occurrence of overlapping fragments from both parental chromosomes can be a substantial loss of information.

The first step in MT is generally low bias whole genome amplification, which can be of particular use in single cell genomic analysis. Due to DNA strand breaks and DNA losses in handling, even single molecule sequencing methods would likely require some level of DNA amplification from the single cell. The difficulty in sequencing single cells comes from attempting to amplify the entire genome. Studies performed on bacteria using MDA have suffered from loss of approximately half of the genome in the final assembled sequence with a fairly high amount of variation in coverage across those sequenced regions. This can partially be explained as a result of the initial genomic DNA having nicks and strand breaks which cannot be replicated at the ends and are thus lost during the MDA process. MT provides a solution to this problem through the creation of long overlapping fragments of the genome prior to MDA. According to one embodiment of the invention, in order to achieve this, a gentle process is used to isolate genomic DNA from the cell. The largely intact genomic DNA is then be lightly treated with a frequent nickase, resulting in a semi-randomly nicked genome. The strand-displacing ability of phi29 is then used to polymerize from the nicks creating very long (>200 kb) overlapping fragments. These fragments are then be used as starting template for MT.

Methylation Analysis Using MT

In a further aspect, methods and compositions of the present invention are used for genomic methylation analysis. There are several methods currently available for global genomic methylation analysis. One method involves bisulfate treatment of genomic DNA and sequencing of repetitive elements or a fraction of the genome obtained by methylation-specific restriction enzyme fragmenting. This technique yields information on total methylation, but provides no locus-specific data. The next higher level of resolution uses DNA arrays and is limited by the number of features on the chip. Finally, the highest resolution and the most expensive approach requires bisulfate treatment followed by sequencing of the entire genome. Using MT it is possible to sequence all bases of the genome and assemble a complete diploid genome with digital information on levels of methylation for every cytosine position in the human genome (i.e., 5-base sequencing). Further, MT allow blocks of methylated sequence of 100 kb or greater to be linked to sequence haplotypes, providing methylation haplotyping, information that is impossible to achieve with any currently available method.

In one non-limiting exemplary embodiment, methylation status is obtained in a method in which genomic DNA is first denatured for MDA. Next the DNA is treated with bisulfite (a step that requires denatured DNA). The remaining preparation follows those methods described for example in U.S. application Ser. No. 11/451,692, filed on Jun. 13, 2006 (published as US 2007/0072208) and Ser. No. 12/335,168, filed on Dec. 15, 2008 (published as US 2009/0311691), each of which is hereby incorporated by reference in its entirety for all purposes and in particular for all teachings related to nucleic acid analysis of mixtures of fragments according to long fragment read techniques.

In one aspect. MDA will amplify each strand of a specific fragment independently yielding for any given cytosine position 50% of the reads as unaffected by bisulfite (i.e., the base opposite of cytosine, a guanine is unaffected by bisulfate) and 50% providing methylation status. Reduced DNA complexity helps with accurate mapping and assembly of the less informative, mostly 3-base (A, T, G) reads.

Bisulfite treatment has been reported to fragment DNA. However, careful titration of denaturation and bisulfate buffers can avoid excessive fragmenting of genomic DNA. A 50% conversion of cytosine to uracil can be tolerated in MT allowing a reduction in exposure of the DNA to bisulfite to minimize fragmenting. In some embodiments, some degree of fragmenting is acceptable as it would not affect haplotyping.

Using MT for Analysis of Cancer Genomes

It has been suggested that more than 90% of cancers harbor significant losses or gains in regions of the human genome, termed aneuploidy, with some individual cancers having been observed to contain in excess of four copies of some chromosomes. This increased complexity in copy number of chromosomes and regions within chromosomes makes sequencing cancer genomes substantially more difficult. The ability of MT techniques to sequence and assemble very long (>100 kb) fragments of the genome makes it well suited for the sequencing of complete cancer genomes.

Error-Reduction by Sequencing a Target Nucleic Acid

According to one embodiment, even if MT-based phasing is not performed and a standard sequencing approach is used, a target nucleic acid is fragmented (if necessary), and the fragments are tagged before amplification. An advantage of MT is that errors introduced as a result of amplification (or other steps) can be identified and corrected by comparing the sequence obtained from multiple overlapping long fragments. For example, a base call (e.g., identifying a particular base such as A, C, G, or T) at a particular position (e.g., with respect to a reference) of the sequence data can be accepted as true if the base call is present In sequence data from two or more long fragments (or other threshold number), or in a substantial majority of long fragments (e.g., in at least 51, 60, 70, or 80 percent), where the denominator can be restricted to the fragments having a base call at the particular position. A base call can include changing one allele of a het or potential het. A base call at the particular position can be accepted as false if it is present in only one long fragment (or other threshold number of long fragments), or in a substantial minority of long fragments (e.g., less than 10, 5, or 3 fragments or as measure with a relative number, such as 20 or 10 percent). The threshold values can be predetermined or dynamically determined based on the sequencing data. A base call at the particular position may be converted/accepted as "no call" if it is not present in a substantial minority and in a substantial majority of expected fragments (e.g., in 40-60 percent). In some embodiments and implementations, various parameters may be used (e.g., in distribution, probability, and/or other functions or statistics) to characterize what may be considered a substantial minority or a substantial majority of fragments. Examples of such parameters include, without limitation, one or more of, number of base calls identifying a particular base; coverage or total number of called bases at a particular position; number and/or identities of distinct fragments that gave rise to sequence data that includes a particular base call: total number of distinct fragments that gave rise to sequence data that includes at least one base call at a particular position; the reference base at the particular position; and others. In one embodiment, a combination of the above parameters for a particular base call can be input to a function to determine a score (e.g., a probability) for the particular base call. The scores can be compared to one or more threshold values as part of determining if a base call is accepted (e.g., above a threshold), in error (e.g., below a threshold), or a no call (e.g., if all of the scores for the base calls are below a threshold). The determination of a base call can be dependent on the scores of the other base calls.

As one basic example, if a base call of A is found in more than 35% (an example of a score) of the fragments that contain a read for the position of interest and a base call of C is found in more than 35% of these fragments and the other base calls each have a score of less than 20%, then the position can be considered a het composed of A and C, possibly subject to other criteria (e.g., a minimum number of fragments containing a read at the position of interest). Thus, each of the scores can be input into another function (e.g., heuristics, which may use comparative or fuzzy logic) to provide the final determination of the base call(s) for the position.

As another example, a specific number of fragments containing a base call may be used as a threshold. For instance, when analyzing a cancer sample, there may be low prevalence somatic mutations. In such a case, the base call may appear in less than 10% of the fragments covering the position, but the base call may still be considered correct, possibly subject to other criteria. Thus, various embodiments can use absolute numbers or relative numbers, or both (e.g., as inputs into comparative or fuzzy logic). And, such numbers of fragments can be input into a function (as mentioned above), as well as thresholds corresponding to each number, and the function can provide a score, which can also be compared to a one or more thresholds to make a final determination as to the base call at the particular position.

A further example of an error correction function relates to sequencing errors in raw reads leading to a putative variant call inconsistent with other variant calls and their haplotypes. If 20 reads of variant A are found in 9 and 8 fragments belonging to respective haplotypes and 7 reads of variant G are found in 6 wells (5 or 6 of which are shared with fragments with A-reads), the logic can reject variant G as a sequencing error because for the diploid genome only one variant can reside at a position in each haplotype. Variant A is supported with substantially more reads, and the G-reads substantially follow fragments of A-reads indicating that they are most likely generate by wrongly reading G instead of A. If G reads are almost exclusively in separate fragments from A, this can indicates that G-reads are wrongly mapped or they come from a contaminating DNA.

Identifying Expansions in Regions with Short Tandem Repeats

A short tandem repeat (STR) in DNA is a segment of DNA with a strong periodic pattern. STRs occur when a pattern of two or more nucleotides are repeated and the repeated sequences are directly adjacent to each other; the repeats may be perfect or imperfect, i.e., there may be a few base pairs that do not match the periodic motif. The pattern generally ranges in length from 2 to 5 base pairs (bp). STRs typically are located in non-coding regions, e.g., in introns. A short tandem repeat polymorphism (STRP) occurs when homologous STR loci differ in the number of repeats between individuals. STR analysis is often used for determining genetic profiles for forensic purposes. STRs occurring in the exons of genes may represent hypermutable regions that are linked to human disease (Madsen at al, BMC Genomics 9:410, 2008).

In human genomes (and genomes of other organisms) STRs include trinucleotide repeats, e.g., CTG or CAG repeats. Trinucleotide repeat expansion, also known as triplet repeat expansion, is caused by slippage during DNA replication, and is associated with certain diseases categorized as trinucleotide repeat disorders such as Huntington Disease. Generally, the larger the expansion, the more likely it is to cause disease or increase the severity of disease. This property results in the characteristic of "anticipation" seen in trinucleotide repeat disorders, that is, the tendency of age of onset of the disease to decrease and the severity of symptoms to increase through successive generations of an affected family due to the expansion of these repeats. Identification of expansions in trinucleotide repeats may be useful for accurately predict age of onset and disease progression for trinucleotide repeat disorders.

Expansion of STRs such as trinucleotide repeats can be difficult to identify using next-generation sequencing methods. Such expansions may not map and may be missing or underrepresented in libraries. Using MT, it is possible to see a significant drop in sequence coverage in an STR region. For example, a region with STRs will characteristically have a lower level of coverage as compared to regions without such repeats, and there will be a substantial drop in coverage in that region if there is an expansion of the region, observable in a plot of coverage versus position in the genome.

For example, if the sequence coverage is about 20 on average, the region with the expansion region will have a significant drop, e.g., to 10 if the affected haplotype has zero coverage in the expansion region. Thus, a 50% drop would occur. However, if the sequence coverage for the two haplotypes is compared, the coverage is 10 in the normal haplotype and 0 in the affected haplotype, which is a drop of 10 but an overall percentage drop of 100%. Or, one can analyze the relative amounts, which is 2:1 (normal vs. coverage in expansion region) for the combined sequence coverage, but is 10:0 (haplotype 1 vs. haplotype 2), which is infinity or zero (depending on how the ratio is formed), and thus a large distinction.

Diagnostic Use of Sequence Data

Sequence data generated using the methods of the present invention are useful for a wide variety of purposes. According to one embodiment, sequencing methods of the present invention are used to identify a sequence variation in a sequence of a complex nucleic acid, e.g., a whole genome sequence, that is informative regarding a characteristic or medical status of a patient or of an embryo or fetus, such as the sex of an embryo or fetus or the presence or prognosis of a disease having a genetic component, including, for example, cystic fibrosis, sickle cell anemia, Marfan syndrome, Huntington's disease, and hemochromatosis or various cancers, such as breast cancer, for example. According to another embodiment, the sequencing methods of the present invention are used to provide sequence information beginning with between one and 20 cells from a patient (including but not limited to a fetus or an embryo) and assessing a characteristic of the patient on the basis of the sequence.

Cancer Diagnostics

Whole genome sequencing is a valuable tool in assessing the genetic basis of disease. A number of diseases are known for which there is a genetic basis, e.g., cystic fibrosis, One application of whole genome sequencing is to understanding cancer. The most significant impact of next-generation sequencing on cancer genomics has been the ability to re-sequence, analyze and compare the matched tumor and normal genomes of a single patient as well as multiple patient samples of a given cancer type. Using whole genome sequencing the entire spectrum of sequence variations can be considered, including germline susceptibility loci, somatic single nucleotide polymorphisms (SNPs), small insertion and deletion (indel) mutations, copy number variations (CNVs) and structural variants (SVs).

In general, the cancer genome is comprised of the patient's germ line DNA, upon which somatic genomic alterations have been superimposed. Somatic mutations identified by sequencing can be classified either as "driver" or "passenger" mutations. So-called driver mutations are those that directly contribute to tumor progression by conferring a growth or survival advantage to the cell. Passenger mutations encompass neutral somatic mutations that have been acquired during errors in cell division, DNA replication, and repair; these mutations may be acquired while the cell is phenotypically normal, or following evidence of a neoplastic change.

Historically, attempts have been made to elucidate the molecular mechanism of cancer, and several "driver" mutations, or biomarkers, such as HER2/neu2, have been identified. Based on such genes, therapeutic regimens have been developed to specifically target tumors with known genetic alterations. The best defined example of this approach is the targeting of HER2/neu in breast cancer cells by trastuzumab (Herceptin). Cancers, however, are not simple monogenetic diseases, but are instead characterized by combinations of genetic alterations that can differ among individuals. Consequently, these additional perturbations to the genome may render some drug regimens ineffective for certain individuals.

Cancer cells for whole genome sequencing may be obtained from biopsies of whole tumors (including microbiopsies of a small number of cells), cancer cells isolated from the bloodstream or other body fluids of a patient, or any other source known In the art.

Pre-Implantation Genetic Diagnosis

One application of the methods of the present invention is for pre-implantation genetic diagnosis. About 2 to 3% of babies born have some type of major birth defect. The risk of some problems, due to abnormal separation of genetic material (chromosomes), increases with the mother's age. About 50% of the time these types of problems are due to Down Syndrome, which is a third copy of chromosome 21 (Trisomy 21). The other half result from other types of chromosomal anomalies, including trisomies, point mutations, structural variations, copy number variations, etc. Many of these chromosomal problems result in a severely affected baby or one which does not survive even to delivery.

In medicine and (clinical) genetics pre-implantation genetic diagnosis (PGD or PIGD) (also known as embryo screening) refers to procedures that are performed on embryos prior to implantation, sometimes even on oocytes prior to fertilization. PGD can permit parents to avoid selective pregnancy termination. The term pre-implantation genetic screening (PGS) is used to denote procedures that do not look for a specific disease but use PGD techniques to identify embryos at risk due, for example, to a genetic condition that could lead to disease. Procedures performed on sex cells before fertilization may instead be referred to as methods of oocyte selection or sperm selection, although the methods and aims partly overlap with PGD.

Preimplantation genetic profiling (PGP) is a method of assisted reproductive technology to perform selection of embryos that appear to have the greatest chances for successful pregnancy. When used for women of advanced maternal age and for patients with repetitive in vitro fertilization (IVF) failure, PGP is mainly carried out as a screening for detection of chromosomal abnormalities such as aneupiody, reciprocal and Robertsonian translocations, and other abnormalities such as chromosomal inversions or deletions. In addition, PGP can examine genetic markers for characteristics, including various disease states The principle behind the use of PGP is that, since it is known that numerical chromosomal abnormalities explain most of the cases of pregnancy loss, and a large proportion of the human embryos are aneuploid, the selective replacement of euploid embryos should increase the chances of a successful IVF treatment. Whole-genome sequencing provides an alternative to such methods of comprehensive chromosome analysis methods as array-comparative genomic hybridization (aCGH), quantitative PCR and SNP microarrays. Whole full genome sequencing can provide information regarding single base changes, insertions, deletions, structural variations and copy number variations, for example.

As PGD can be performed on cells from different developmental stages, the biopsy procedures vary accordingly. The biopsy can be performed at all preimplantation stages, including but not limited to unfertilized and fertilized oocytes (for polar bodies, PBs), on day three cleavage-stage embryos (for blastomeres) and on blastocysts (for trophectoderm cells).

Sequencing Systems and Data Analysis

In some embodiments, sequencing of DNA samples (e.g., such as samples representing whole human genomes) may be performed by a sequencing system. Two examples of sequencing systems are illustrated in FIG. 5.

Figure 5A:
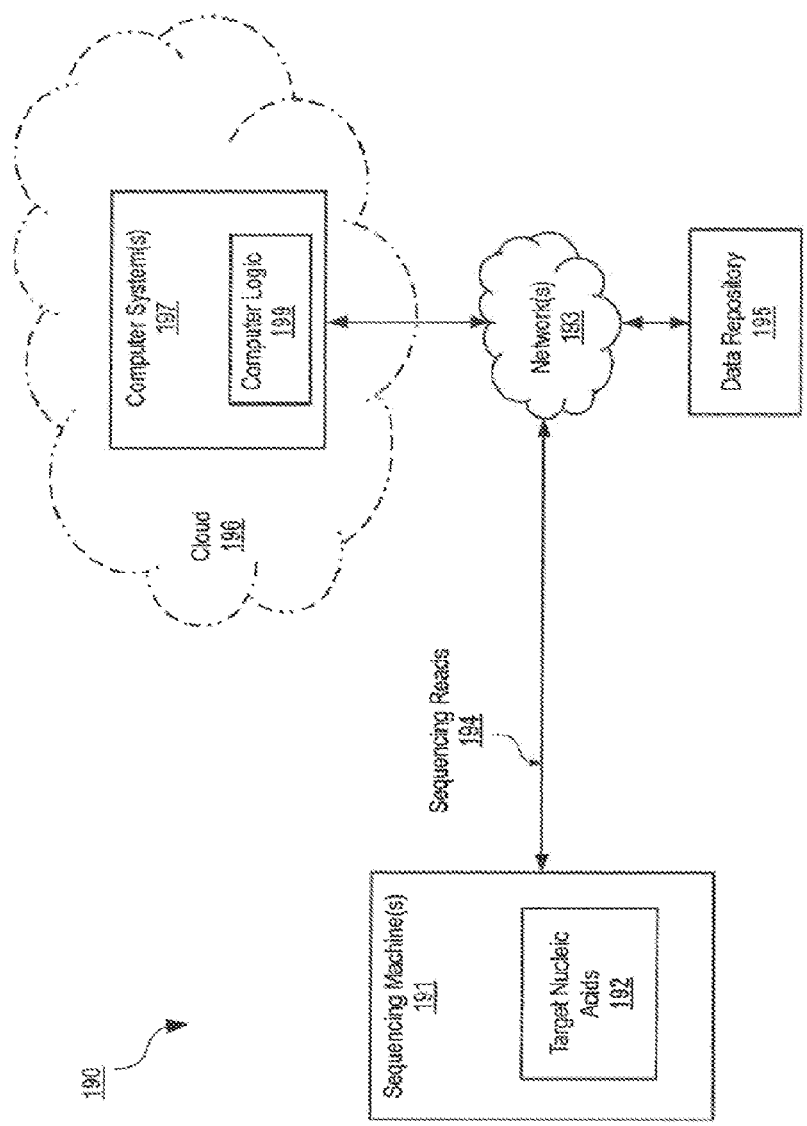
FIGS. 5A and 5B show examples of sequencing systems.
Figure 5B:
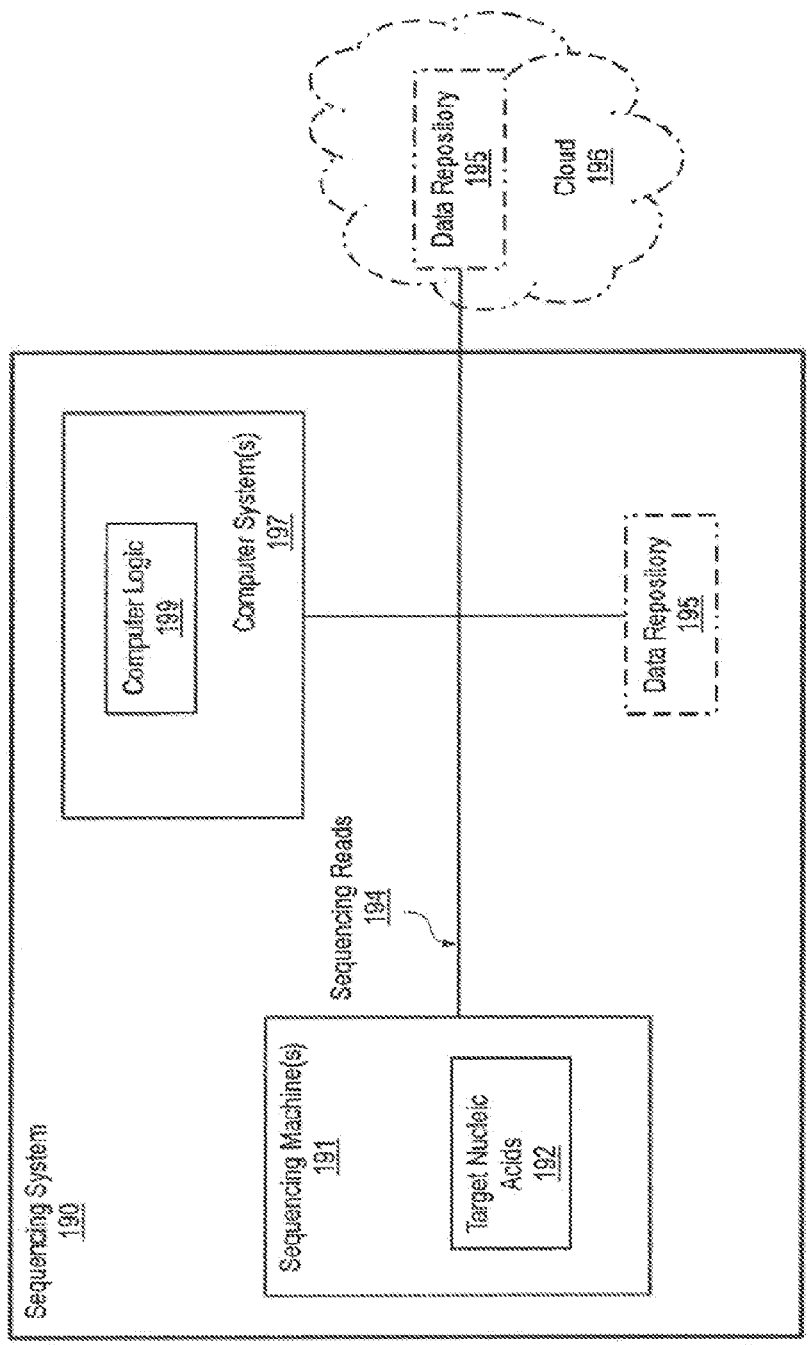

FIGS. 5A and 5B are block diagrams of example sequencing systems 190 that are configured to perform the techniques and/or methods for nucleic acid sequence analysis according to the embodiments described herein. A sequencing system 190 can include or be associated with multiple subsystems such as, for example, one or more sequencing machines such as sequencing machine 191, one or more computer systems such as computer system 197, and one or more data repositories such as data repository 195. In the embodiment illustrated in FIG. 5A, the various subsystems of system 190 may be communicatively connected over one or more networks 193, which may include packet-switching or other types of network infrastructure devices (e.g., routers, switches, etc.) that are configured to facilitate information exchange between remote systems. In the embodiment illustrated in FIG. 5B, sequencing system 190 is a sequencing device in which the various subsystems (e.g., such as sequencing machine(s) 191, computer system(s) 197, and possibly a data repository 195) are components that are communicatively and/or operatively coupled and integrated within the sequencing device.

In some operational contexts, data repository 195 and/or computer system(s) 197 of the embodiments illustrated in FIGS. 5A and 5B may be configured within a cloud computing environment 196. In a cloud computing environment, the storage devices comprising a data repository and/or the computing devices comprising a computer system may be allocated and instantiated for use as a utility and on-demand; thus, the cloud computing environment provides as services the infrastructure (e.g., physical and virtual machines, raw/block storage, firewalls, load-balancers, aggregators, networks, storage clusters, etc.), the platforms (e.g., a computing device and/or a solution stack that may include an operating system, a programming language execution environment, a database server, a web server, an application server, etc.), and the software (e.g., applications, application programming interfaces or APIs, etc.) necessary to perform any storage-related and/or computing tasks.

It is noted that in various embodiments, the techniques described herein can be performed by various systems and devices that include some or all of the above subsystems and components (e.g., such as sequencing machines, computer systems, and data repositories) in various configurations and form factors; thus, the example embodiments and configurations illustrated in FIGS. 5A and 58B are to be regarded in an illustrative rather than a restrictive sense.

Sequencing machine 191 is configured and operable to receive target nucleic acids 192 derived from fragments of a biological sample, and to perform sequencing on the target nucleic acids. Any suitable machine that can perform sequencing may be used, where such machine may use various sequencing techniques that include, without limitation, sequencing by hybridization, sequencing by ligation, sequencing by synthesis, single-molecule sequencing, optical sequence detection, electro-magnetic sequence detection, voltage-change sequence detection, and any other now-known or later-developed technique that is suitable for generating sequencing reads from DNA. In various embodiments, a sequencing machine can sequence the target nucleic acids and can generate sequencing reads that may or may not include gaps and that may or may not be mate-pair (or paired-end) reads. As illustrated in FIGS. 5A and 5B, sequencing machine 191 sequences target nucleic acids 192 and obtains sequencing reads 194, which are transmitted for (temporary and/or persistent) storage to one or more data repositories 195 and/or for processing by one or more computer systems 197.

Data repository 195 may be implemented on one or more storage devices (e.g., hard disk drives, optical disks, solid-state drives, etc.) that may be configured as an array of disks (e.g., such as a SCSI array), a storage cluster, or any other suitable storage device organization. The storage device(s) of a data repository can be configured as internal/integral components of system 190 or as external components (e.g., such as external hard drives or disk arrays) attachable to system 190 (e.g., as illustrated in FIG. 58B), and/or may be communicatively interconnected in a suitable manner such as, for example, a grid, a storage cluster, a storage area network (SAN), and/or a network attached storage (NAS) (e.g., as illustrated in FIG. 5A). In various embodiments and implementations, a data repository may be implemented on the storage devices as one or more file systems that store information as files, as one or more databases that store information in data records, and/or as any other suitable data storage organization.

Computer system 197 may include one or more computing devices that comprise general purpose processors (e.g., Central Processing Units, or CPUs), memory, and computer logic 199 which, along with configuration data and/or operating system (OS) software, can perform some or all of the techniques and methods described herein, and/or can control the operation of sequencing machine 191. For example, any of the methods described herein (e.g., for error correction, haplotype phasing, etc.) can be totally or partially performed by a computing device including a processor that can be configured to execute logic 199 for performing various steps of the methods. Further, although method steps may be presented as numbered steps, it is understood that steps of the methods described herein can be performed at the same time (e.g., in parallel by a cluster of computing devices) or in a different order. The functionalities of computer logic 199 may be implemented as a single integrated module (e.g., in an integrated logic) or may be combined in two or more software modules that may provide some additional functionalities.

In some embodiments, computer system 197 may be a single computing device. In other embodiments, computer system 197 may comprise multiple computing devices that may be communicatively and/or operatively interconnected in a grid, a cluster, or in a cloud computing environment. Such multiple computing devices may be configured in different form factors such as computing nodes, blades, or any other suitable hardware configuration. For these reasons, computer system 197 in FIGS. 5A and 5B is to be regarded in an illustrative rather than a restrictive sense.

Figure 6:
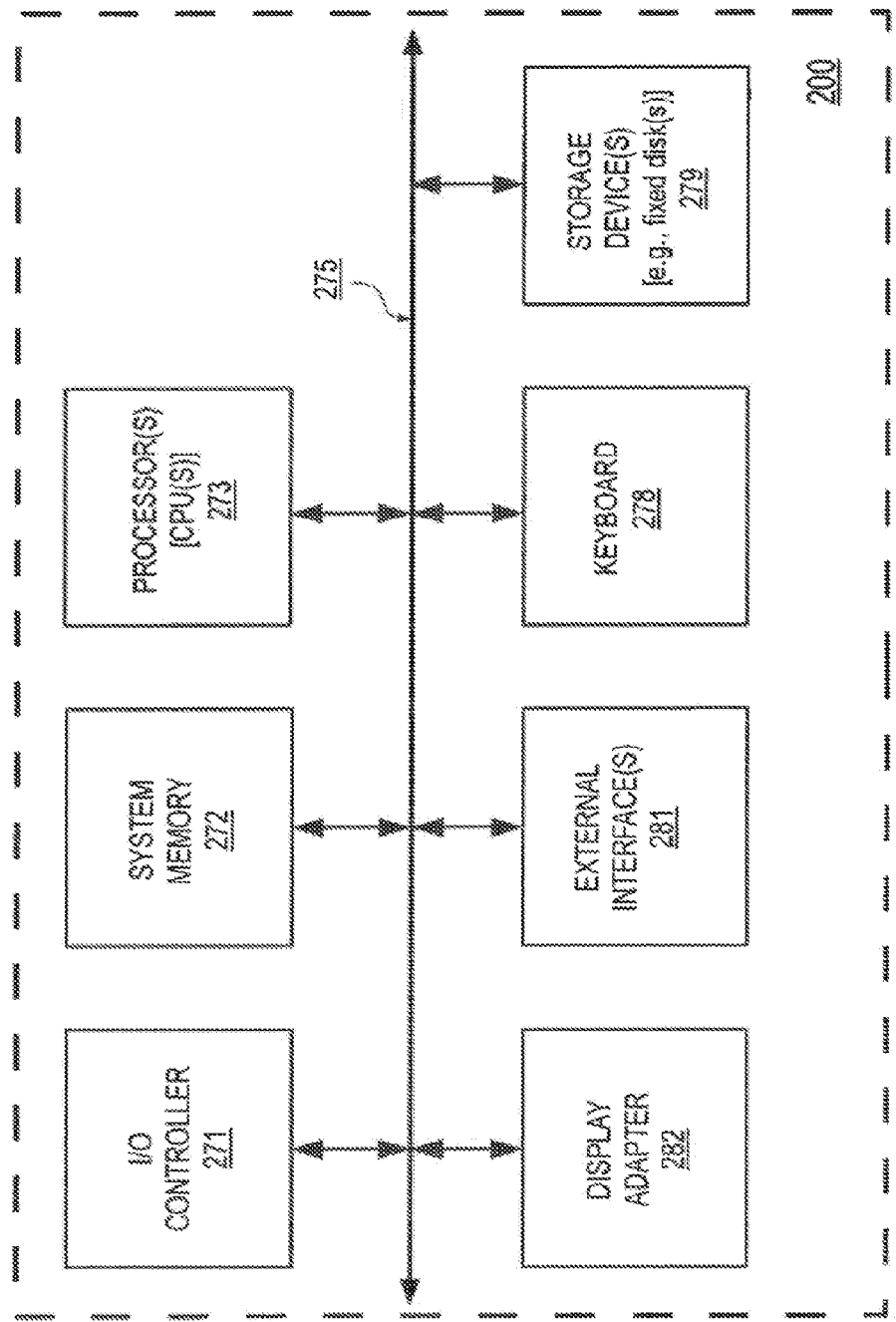
FIG. 6 shows an example of a computing device that can be used in, or in conjunction with, a sequencing machine and/or a computer system.

FIG. 6 is a block diagram of an example computing device 200 that can be configured to execute instructions for performing various data-processing and/or control functionalities as part of sequencing machine(s) and/or computer system(s).

In FIG. 6, computing device 200 comprises several components that are interconnected directly or indirectly via one or more system buses such as bus 275. Such components may include, but are not limited to, keyboard 278, persistent storage device(s) 279 (e.g., such as fixed disks, solid-state disks, optical disks, and the like), and display adapter 282 to which one or more display devices (e.g., such as LCD monitors, flat-panel monitors, plasma screens, and the like) may be coupled. Peripherals and input/output (I/O) devices, which couple to I/O controller 271, can be connected to computing device 200 by any number of means known in the art including, but not limited to, one or more serial ports, one or more parallel ports, and one or more universal serial buses (USBs). External interface(s) 281 (which may include a network interface card and/or serial ports) can be used to connect computing device 200 to a network (e.g., such as the Internet or a local area network (LAN)). External interface(s) 281 may also include a number of input interfaces that can receive information from various external devices such as, for example, a sequencing machine or any component thereof. The interconnection via system bus 275 allows one or more processors (e.g., CPUs) 273 to communicate with each connected component and to execute (and/or control the execution of) instructions from system memory 272 and/or from storage device(s) 279, as well as the exchange of information between various components. System memory 272 and/or storage device(s) 279 may be embodied as one or more computer-readable non-transitory storage media that store the sequences of instructions executed by processor(s) 273, as well as other data. Such computer-readable non-transitory storage media include, but is not limited to, random access memory (RAM), read-only memory (ROM), an electro-magnetic medium (e.g., such as a hard disk drive, solid-state drive, thumb drive, floppy disk, etc.), an optical medium such as a compact disk (CD) or digital versatile disk (DVD), flash memory, and the like. Various data values and other structured or unstructured information can be output from one component or subsystem to another component or subsystem, can be presented to a user via display adapter 282 and a suitable display device, can be sent through external interface(s) 281 over a network to a remote device or a remote data repository, or can be (temporarily and/or permanently) stored on storage device(s) 279.

Any of the methods and functionalities performed by computing device 200 can be implemented in the form of logic using hardware and/or computer software in a modular or integrated manner. As used herein, "logic" refers to a set of instructions which, when executed by one or more processors (e.g., CPUs) of one or more computing devices, are operable to perform one or more functionalities and/or to return data in the form of one or more results or data that is used by other logic elements. In various embodiments and implementations, any given logic may be implemented as one or more software components that are executable by one or more processors (e.g., CPUs), as one or more hardware components such as Application-Specific Integrated Circuits (ASICs) and/or Field-Programmable Gate Arrays (FPGAs), or as any combination of one or more software components and one or more hardware components. The software component(s) of any particular logic may be implemented, without limitation, as a standalone software application, as a client in a client-server system, as a server in a client-server system, as one or more software modules, as one or more libraries of functions, and as one or more static and/or dynamically-linked libraries. During execution, the instructions of any particular logic may be embodied as one or more computer processes, threads, fibers, and any other suitable run-time entities that can be instantiated on the hardware of one or more computing devices and can be allocated computing resources that may include, without limitation, memory, CPU time, storage space, and network bandwidth.

Techniques and Algorithms for the MT Process
Base-Calling

In some embodiments, data extraction will rely on two types of image data: bright-field images to demarcate the positions of all DNBs on a surface, and sets of fluorescence images acquired during each sequencing cycle. Data extraction software can be used to identify all objects with the bright-field images and then for each such object, the software can be used to compute an average fluorescence value for each sequencing cycle. For any given cycle, there are four data points, corresponding to the four images taken at different wavelengths to query whether that base is an A, G, C or T. These raw data points (also referred to herein as "base calls") are consolidated, yielding a discontinuous sequencing read for each DNB.

A computing device can assemble the population of identified bases to provide sequence information for the target nucleic acid and/or identify the presence of particular sequences in the target nucleic acid. For example, the computing device may assemble the population of identified bases in accordance with the techniques and algorithms described herein by executing various logic; an example of such logic is software code written in any suitable programming language such as Java, C++, Perl, Python, and any other suitable conventional and/or object-oriented programming language. When executed in the form of one or more computer processes, such logic may read, write, and/or otherwise process structured and unstructured data that may be stored in various structures on persistent storage and/or in volatile memory; examples of such storage structures include, without limitation, files, tables, database records, arrays, lists, vectors, variables, memory and/or processor registers, persistent and/or memory data objects instantiated from object-oriented classes, and any other suitable data structures. In some embodiments, the identified bases are assembled into a complete sequence through alignment of overlapping sequences obtained from multiple sequencing cycles performed on multiple DNBs. As used herein, the term "complete sequence" refers to the sequence of partial or whole genomes as well as partial or whole target nucleic acids. In further embodiments, assembly methods performed by one or more computing devices or computer logic thereof utilize algorithms that can be used to "piece together" overlapping sequences to provide a complete sequence. In still further embodiments, reference tables are used to assist in assembling the identified sequences into a complete sequence. A reference table may be compiled using existing sequencing data on the organism of choice. For example human genome data can be accessed through the National Center for Biotechnology Information at ftp.ncbi.nih.gov/refseq/release, or through the J. Craig Venter Institute. All or a subset of human genome information can be used to create a reference table for particular sequencing queries. In addition, specific reference tables can be constructed from empirical data derived from specific populations, including genetic sequence from humans with specific ethnicities, geographic heritage, religious or culturally-defined populations, as the variation within the human genome may slant the reference data depending upon the origin of the information contained therein.

In any of the embodiments of the invention discussed herein, a population of nucleic acid templates and/or DNBs may comprise a number of target nucleic acids to substantially cover a whole genome or a whole target polynucleotide. As used herein, "substantially covers" means that the amount of nucleotides (i.e., target sequences) analyzed contains an equivalent of at least two copies of the target polynucleotide, or in another aspect, at least ten copies, or in another aspect, at least twenty copies, or in another aspect, at least 100 copies. Target polynucleotides may include DNA fragments, including genomic DNA fragments and cDNA fragments, and RNA fragments. Guidance for the step of reconstructing target polynucleotide sequences can be found in the following references, which are incorporated by reference: Lander et al, Genomics, 2: 231-239 (1988); Vingron et al, J. Mol. Biol., 235:1-12 (1994); and like references.

In some embodiments, four images, one for each color dye, are generated for each queried position of a complex nucleotide that is sequenced. The position of each spot in an image and the resulting intensities for each of the four colors is determined by adjusting for crosstalk between dyes and background intensity. A quantitative model can be fit to the resulting four-dimensional dataset. A base is called for a given spot, with a quality score that reflects how well the four intensities fit the model.

Base calling of the four images for each field can be performed in several steps by one or more computing devices or computer logic thereof. First, the image intensities are corrected for background using modified morphological "image open" operation. Since the locations of the DNBs line up with the camera pixel locations, the intensity extraction is done as a simple read-out of pixel intensities from the background corrected images. These intensities are then corrected for several sources of both optical and biological signal cross-talks, as described below. The corrected intensities are then passed to a probabilistic model that ultimately produces for each DNB a set of four probabilities of the four possible base call outcomes. Several metrics are then combined to compute the base call score using pre-fitted logistic regression.

Intensity Correction

Several sources of biological and optical cross-talks are corrected using linear regression model implemented as computer logic that is executed by one or more computing devices. The linear regression was preferred over de-convolution methods that are computationally more expensive and produced results with similar quality. The sources of optical cross-talks include filter band overlaps between the four fluorescent dye spectra, and the lateral cross-talks between neighboring DNBs due to light diffraction at their close proximities. The biological sources of cross-talks include incomplete wash of previous cycle, probe synthesis errors and probe "slipping" contaminating signals of neighboring positions, Incomplete anchor extension when interrogating "outer" (more distant) bases from anchors. The linear regression is used to determine the part of DNB intensities that can be predicted using intensities of either neighboring DNBs or Intensities from previous cycle or other DNB positions. The part of the intensities that can be explained by these sources of cross-talk is then subtracted from the original extracted intensities. To determine the regression coefficients, the intensities on the left side of the linear regression model need to be composed primarily of only "background" intensities, i.e., intensities of DNBs that would not be called the given base for which the regression is being performed. This requires pre-calling step that is done using the original intensities. Once the DNBs that do not have a particular base call (with reasonable confidence) are selected, a computing device or computer logic thereof performs a simultaneous regression of the cross-talk sources:

$$I_{background}{}^{Base} \approx I_{DNBneighbor1}{}^{Base} + \ldots + I_{DNBneighborN}{}^{Base} + I_{DNB}{}^{Base2} + I_{DNB}{}^{Base3} + I_{DNB}{}^{Base4} + I_{DNBpreviousCycle}{}^{Base} + I_{DNBotherPosition1}{}^{Base} + \ldots + I_{DNBotherPositionN}{}^{Base} + \varepsilon$$

The neighbor DNB cross-talk is corrected both using the above regression. Also, each DNB is corrected for its particular neighborhood using a linear model involving all neighbors over all available DNB positions.

Base Call Probabilities

Calling bases using maximum intensity does not account for the different shapes of background intensity distributions of the four bases. To address such possible differences, a probabilistic model was developed based on empirical probability distributions of the background intensities. Once the intensities are corrected, a computing device or computer logic thereof pre-calls some DNBs using maximum intensities (DNBs that pass a certain confidence threshold) and uses these pre-called DNBs to derive the background intensity distributions (distributions of intensities of DNBs that are not called a given base). Upon obtaining such distributions, the computing device can compute for each DNB a tail probability under that distribution that describes the empirical probability of the intensity being background intensity. Therefore, for each DNB and each of the four intensities, the computing device or logic thereof can obtain and store their probabilities of being background ($p_{BG}{}^A$, $p_{BG}{}^C$, $p_{BG}{}^G$, $p_{BG}{}^T$). Then the computing device can compute the probabilities of all possible base call outcomes using these probabilities. The possible base call outcomes need to describe also spots that can be double or in general multiple-occupied or not occupied by a DNB. Combining the computed probabilities with their prior probabilities (lower prior for multiple-occupied or empty spots) gives rise to the probabilities of the 16 possible outcomes:

$$p^A = \frac{! p_{BG}^A + p_{BG}^C + p_{BG}^G + p_{BG}^T}{\sum p} * p_{SingleBase}^{prior}$$

$$p^{AC} = \frac{! p_{BG}^A + ! p_{BG}^C + p_{BG}^G + p_{BG}^T}{\sum p} * p_{DoubleOccupied}^{prior}$$

$$p^{ACG} = \frac{! p_{BG}^A + ! p_{BG}^C + ! p_{BG}^G + p_{BG}^T}{\sum p} * p_{TripleOccupied}^{prior}$$

$$p^{ACGT} = \frac{! p_{BG}^A + ! p_{BG}^C + ! p_{BG}^G + ! p_{BG}^T}{\sum p} * p_{QuadrupleOccupied}^{prior}$$

-continued $$p^N = \frac{p_{BG}^A + p_{BG}^C + p_{BG}^G + p_{BG}^T}{\sum p} * p_{EmptySpot}^{prior}$$

These 16 probabilities can then be combined to obtain a reduced set of four probabilities for the four possible base-calls. That is:

$$p_{Abase}{}^A = p^A + \frac{1}{2}(p^{AC} + p^{AG} + p^{AT}) + \frac{1}{3}(p^{ACG} + p^{ACT} + p^{AGT}) + \frac{1}{4}p^{ACGT} + \frac{1}{4}p^N$$

Score Computation

Logistic regression was used to derive the score computation formula. A computing device or computer logic thereof fitted the logistic regression to mapping outcomes of the basecall using several metrics as inputs. The metrics included probability ratio between the called base and the next highest base, called base intensity, indicator variable of the base call identity, and metrics describing the overall clustering quality of the field. All metrics were transformed to be collinear with log-odds-ratio between concordant and discordant calls. The model was refined using cross-validation. The logit function with the final logistic regression coefficients was used to compute the scores in production.

Mapping and Assembly

In further embodiments, read data is encoded in a compact binary format and includes both a called base and quality score. The quality score is correlated with base accuracy. Analysis software logic, Including sequence assembly software, can use the score to determine the contribution of evidence from individual bases with a read.

Reads may be "gapped" due to the DNB structure. Gap sizes vary (usually +/−1 base) due to the variability inherent in enzyme digestion. Due to the random-access nature of cPAL, reads may occasionally have an unread base ("nocall") in an otherwise high-quality DNB. Read pairs are mated.

Mapping software logic capable of aligning read data to a reference sequence can be used to map data generated by the sequencing methods described herein. When executed by one or more computing devices, such mapping logic will generally be tolerant of small variations from a reference sequence, such as those caused by individual genomic variation, read errors, or unread bases. This property often allows direct reconstruction of SNPs. To support assembly of larger variations, including large-scale structural changes or regions of dense variation, each arm of a DNB can be mapped separately, with mate pairing constraints applied after alignment.

As used herein, the term "sequence variant" or simply "variant" includes any variant, including but not limited to a substitution or replacement of one or more bases; an insertion or deletion of one or more bases (also referred to as an "indel"); Inversion; conversion; duplication, or copy number variation (CNV); trinucleotide repeat expansion; structural variation (SV; e.g., Intrachromosomal or interchromosomal rearrangement, e.g., a translocation); etc. In a diploid genome, a "heterozygosity" or "het" is two different alleles of a particular gene in a gene pair. The two alleles may be different mutants or a wild type allele paired with a mutant. The present methods can also be used in the analysis of non-diploid organisms, whether such organisms are haploid/monoploid (N=1, where N=haploid number of chromosomes), or polyploid, or aneuploid.

Assembly of sequence reads can in some embodiments utilize software logic that supports DNB read structure (mated, gapped reads with non-called bases) to generate a diploid genome assembly that can in some embodiments be leveraged off of sequence information generating MT methods of the present invention for phasing heterozygote sites.

Methods of the present invention can be used to reconstruct novel segments not present in a reference sequence. Algorithms utilizing a combination of evidential (Bayesian) reasoning and de Bruijin graph-based algorithms may be used in some embodiments. In some embodiments, statistical models empirically calibrated to each dataset can be used, allowing all read data to be used without pre-filtering or data trimming. Large scale structural variations (including without limitation deletions, translocations, and the like) and copy number variations can also be detected by leveraging mated reads.

Phasing MT Data

FIG. 7 describes the main steps in the phasing of MT data. These steps are as follows:

(1) Graph Construction Using MT Data:

One or more computing devices or computer logic thereof generates an undirected graph, where the vertices represent the heterozygous SNPs, and the edges represent the connection between those heterozygous SNPs. The edge is composed of the orientation and the strength of the connection. The one or more computing devices may store such graph in storage structures include, without limitation, files, tables, database records, arrays, lists, vectors, variables, memory and/or processor registers, persistent and/or memory data objects instantiated from object-oriented classes, and any other suitable temporary and/or persistent data structures.

(2) Graph Construction Using Mate Pair Data:

Step 2 is similar to step 1, where the connections are made based on the mate pair data, as opposed to the MT data. For a connection to be made, a DNB can be found with the two heterozygous SNPs of interest in the same read (same arm or mate arm).

(3) Graph Combination:

A computing device or computer logic thereof represents of each of the above graphs is via an N×N sparse matrix, where N is the number of candidate heterozygous SNPs on that chromosome. Two nodes can only have one connection in each of the above methods. Where the two methods are combined, there may be up to two connections for two nodes. Therefore, the computing device or computer logic thereof may use a selection algorithm to select one connection as the connection of choice. The quality of the mate-pair data is significantly inferior to that of the MT data. Therefore, only the MT-derived connections are used.

(4) Graph Trimming:

A series of heuristics were devised and applied, by a computing device, to stored graph data In order to remove some of the erroneous connections. More precisely, a node can satisfy the condition of at least two connections in one direction and one connection in the other direction; otherwise, it is eliminated.

(5) Graph Optimization:

A computing device or computer logic thereof optimized the graph by generating the minimum-spanning tree (MST). The energy function was set to −|strength|. During this process, where possible, the lower strength edges get eliminated, due to the competition with the stronger paths. Therefore, MST provides a natural selection for the strongest and most reliable connections.

(6) Contig Building:

Once the minimum-spanning tree is generated and/or stored in computer-readable medium, a computing device or logic thereof can re-orient all the nodes with taking one node (here, the first node) constant. This first node is the anchor node. For each of the nodes, the computing device then finds the path to the anchor node. The orientation of the test node is the aggregate of the orientations of the edges on the path.

(7) Universal Phasing:

After the above steps, a computing device or logic thereof phases each of the contigs that are built in the previous step(s). Here, the results of this part are referred to as pre-phased, as opposed to phased, indicating that this is not the final phasing. Since the first node was chosen arbitrarily as the anchor node, the phasing of the whole contig is not necessarily in-line with the parental chromosomes. For universal phasing, a few heterozygous SNPs on the contig for which trio information is available are used. These trio heterozygous SNPs are then used to identify the alignment of the contig. At the end of the universal phasing step, all the contigs have been labeled properly and therefore can be considered as a chromosome-wide contig.

Contig Making

Figure 8:
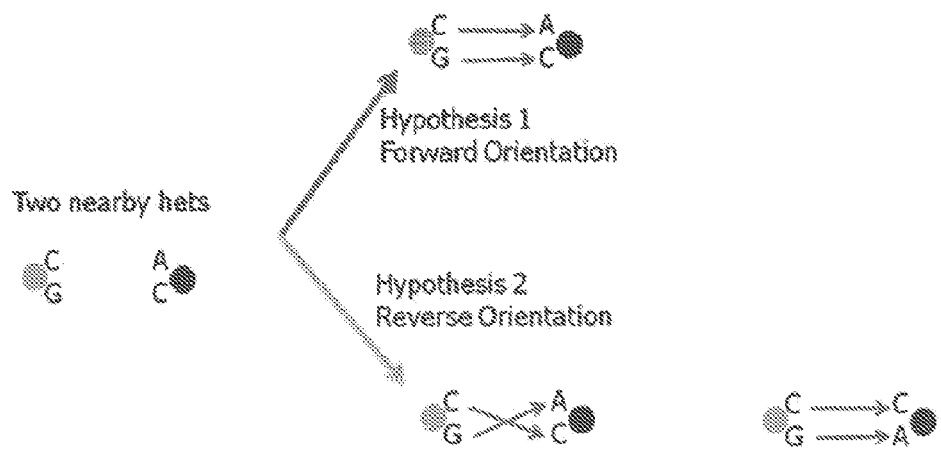
FIG. 8 shows pairwise analysis of nearby heterozygous SNPs.

In order to make contigs, for each heterozygous SNP-pair, a computing device or computer logic thereof tests two hypotheses: the forward orientation and reverse orientation. A forward orientation means that the two heterozygous SNPs are connected the same way they are originally listed (initially alphabetically). A reverse orientation means that the two heterozygous SNPs are connected In reverse order of their original listing. FIG. 8 depicts the pairwise analysis of nearby heterozygous SNPs involving the assignment of forward and reverse orientations to a heterozygous SNP-pair.

Figure 9:
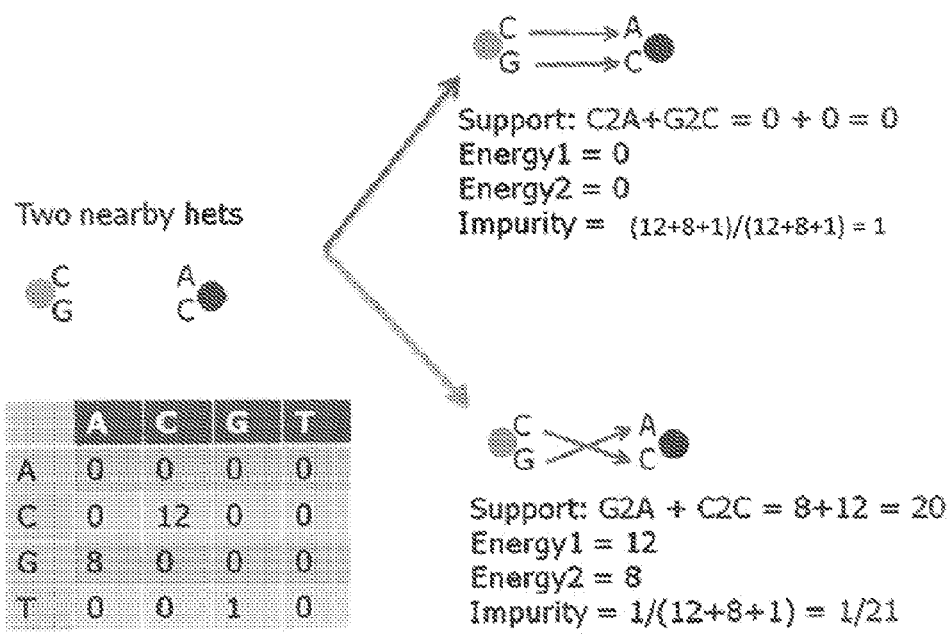
FIG. 9 shows an example of the selection of an hypothesis and the assignment of a score to the hypothesis.

Each orientation will have a numerical support, showing the validity of the corresponding hypothesis. This support is a function of the 16 cells of the connectivity matrix shown in FIG. 9, which shows an example of the selection of a hypothesis, and the assignment of a score to it. To simplify the function, the 16 variables are reduced to 3: Energy1, Energy2 and Impurity. Energy 1 and Energy2 are two highest value cells corresponding to each hypothesis. Impurity is the ratio of the sum of all the other cells (than the two corresponding to the hypothesis) to the total sum of the cells In the matrix. The selection between the two hypotheses is done based on the sum of the corresponding cells. The hypothesis with the higher sum is the winning hypothesis. The following calculations are only used to assign the strength of that hypothesis. A strong hypothesis is the one with a high value for Energy1 and Energy2, and a low value for impurity.

Figure 10:
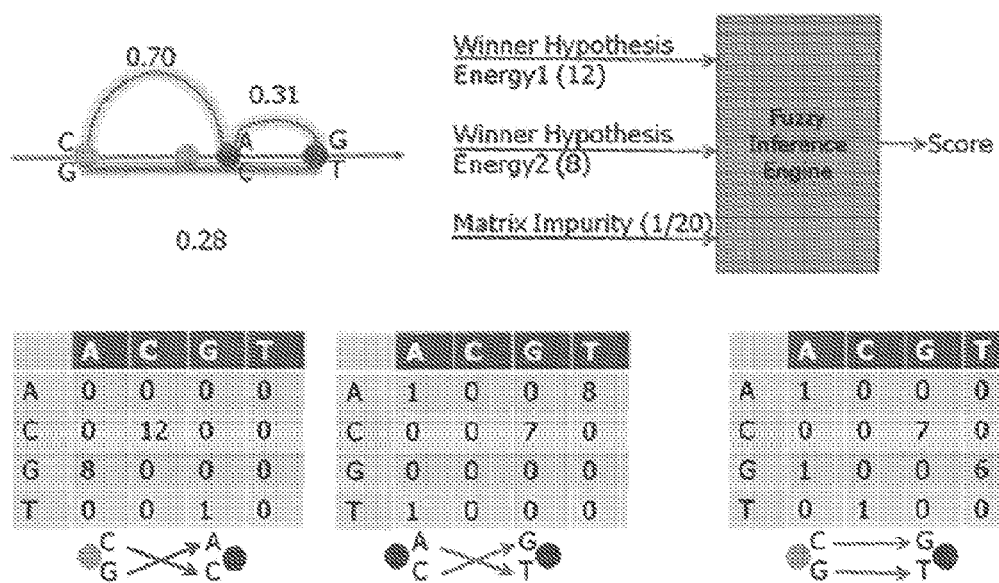
FIG. 10 shows graph construction.

The three metrics Energy1, Energy2 and Impurity are fed into a fuzzy inference system (FIG. 10), in order to reduce their effects into a single value—score—between (and including) 0 and 1. The fuzzy interference system (FIS) is implemented as a computer logic that can be executed by one or more computing devices.

The connectivity operation is done for each heterozygous SNP pair that is within a reasonable distance up to the expected contig length (e.g., 20-50 Kb). FIG. 6 shows graph construction, depicting some exemplary connectivities and strengths for three nearby heterozygous SNPs.

The rules of the fuzzy inference engine are defined as follows:

(1) If Energy1 is small and Energy2 is small, then Score is very small.

(2) If Energy1 is medium and Energy2 is small, then Score is small.

(3) If Energy1 is medium and Energy2 is medium, then Score is medium.

(4) If Energy1 is large and Energy2 is small, then Score is medium.

(5) If Energy1 is large and Energy2 is medium, then Score is large.

(6) If Energy1 is large and Energy2 is large, then Score is very large.

(7) If Impurity Is small, then Score Is large.

(8) If Impurity is medium, then Score is small.

(9) If Impurity is large, then Score is very small.

For each variable, the definition of Small, Medium and Large is different, and is governed by its specific membership functions.

Figure 11:
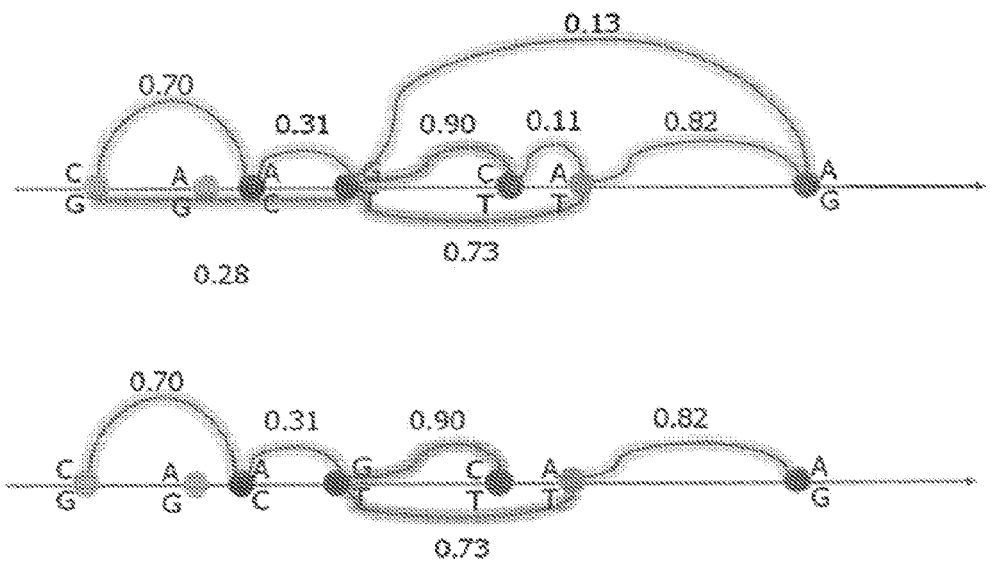
FIG. 11 shows graph optimization.

After exposing the fuzzy inference system (FIS) to each variable set, the contribution of the input set on the rules is propagated through the fuzzy logic system, and a single (de-fuzzified) number is generated at the output—score. This score is limited between 0 and 1, with 1 showing the highest quality After the application of the FIS to each node pair, a computing device or computer logic thereof constructs a complete graph. FIG. 11 shows an example of such graph. The nodes are colored according to the orientation of the winning hypothesis. The strength of each connection is derived from the application of the FIS on the heterozygous SNP pair of interest. Once the preliminary graph is constructed (the top plot of FIG. 11), the computing device or computer logic thereof optimizes the graph (the bottom plot of FIG. 11) and reduces it to a tree. This optimization process is done by making a Minimum Spanning Tree (MST) from the original graph. The MST guarantees a unique path from each node to any other node.

Figure 12:
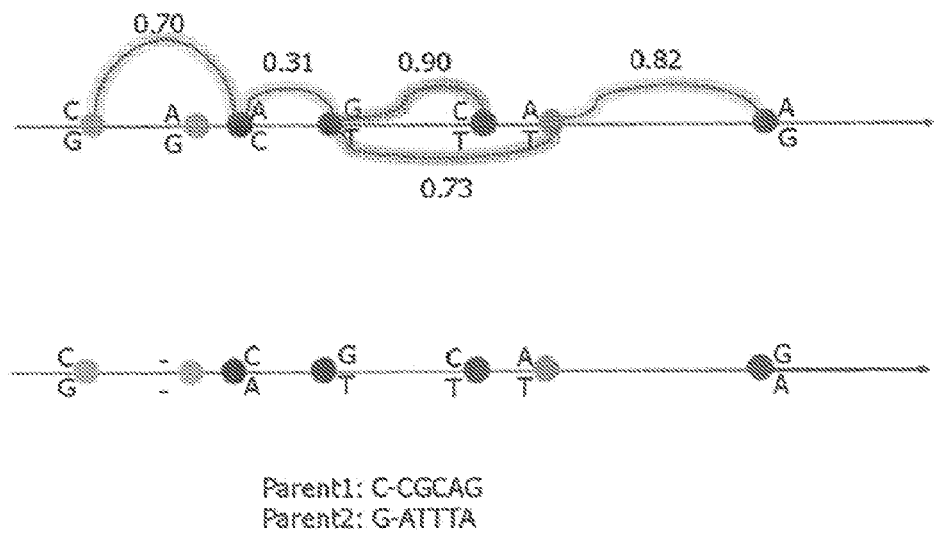
FIG. 12 shows contig alignment.

FIG. 11 shows graph optimization. In this application, the first node on each contig is used as the anchor node, and all the other nodes are oriented to that node. Depending on the orientation, each hit would have to either flip or not, in order to match the orientation of the anchor node. FIG. 12 shows the contig alignment process for the given example. At the end of this process, a phased contig is made available.

Figure 13:
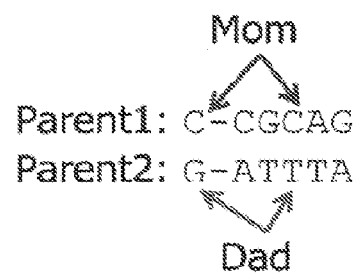
FIG. 13 shows parent-assisted universal phasing.

At this point In the process of phasing, the two haplotypes are separated. Although it is known that one of these haplotypes comes from the Mom and one from the Dad, it is not known exactly which one comes from which parent. In the next step of phasing, a computing device or computer logic thereof attempts to assign the correct parental label (Mom/Dad) to each haplotype. This process is referred to as the Universal Phasing. In order to do so, one needs to know the association of at least a few of the heterozygous SNPs (on the contig) to the parents. This information can be obtained by doing a Trio (Mom-Dad-Child) phasing. Using the trio's sequenced genomes, some loci with known parental associations are identified—more specifically when at least one parent is homozygous. These associations are then used by the computing device or computer logic thereof to assign the correct parental label (Mom/Dad) to the whole contigs, that is, to perform parent-assisted universal phasing (FIG. 13).

In order to guarantee high accuracy, the following may be performed: (1) when possible (e.g., in the case of NA19240), acquiring the trio information from multiple sources, and using a combination of such sources; (2) requiring the contigs to include at least two known trio-phased loci; (3) eliminating the contigs that have a series of trio-mismatches in a row (indicating a segmental error); and (4) eliminating the contigs that have a single trio-mismatch at the end of the trio loci (indicating a potential segmental error).

Figure 14:
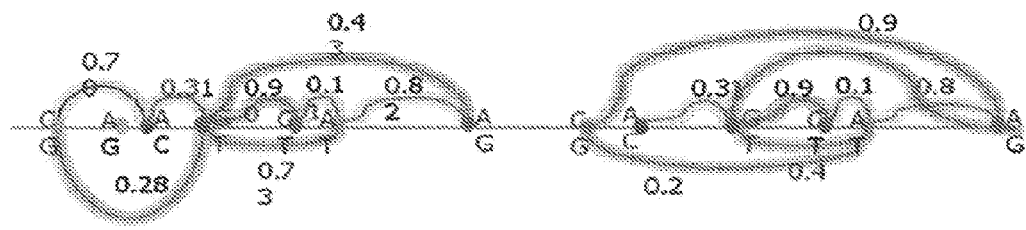
FIG. 14 shows natural contig separations.

FIG. 14 shows natural contig separations. Whether parental data are used or not, contigs often do not continue naturally beyond a certain point. Reasons for contig separation are: (1) more than usual DNA fragmentation or lack of amplification in certain areas, (2) low heterozygous SNP density, (3) poly-N sequence on the reference genome, and (4) DNA repeat regions (prone to mis-mapping).

Figure 15:
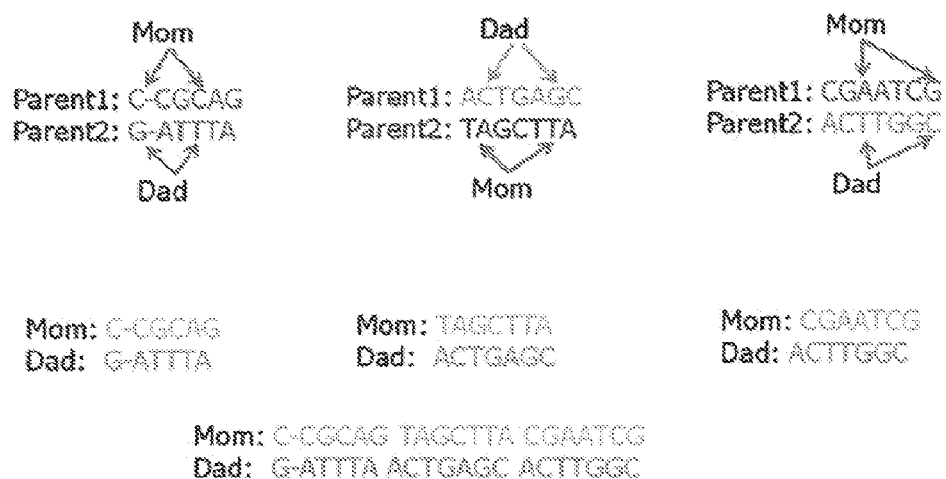
FIG. 15 shows universal phasing.

FIG. 15 shows Universal Phasing. One of the major advantages of Universal Phasing is the ability to obtain the full chromosomal "contigs." This is possible because each contig (after Universal Phasing) carries haplotypes with the correct parental labels. Therefore, all the contigs that carry the label Mom can be put on the same haplotype; and a similar operation can be done for Dad's contigs.

Figure 16:
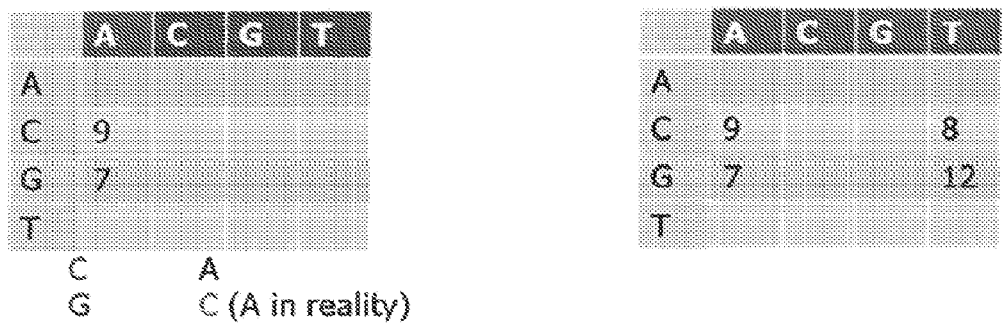
FIG. 16 shows error detection using MT.
Figure 17:
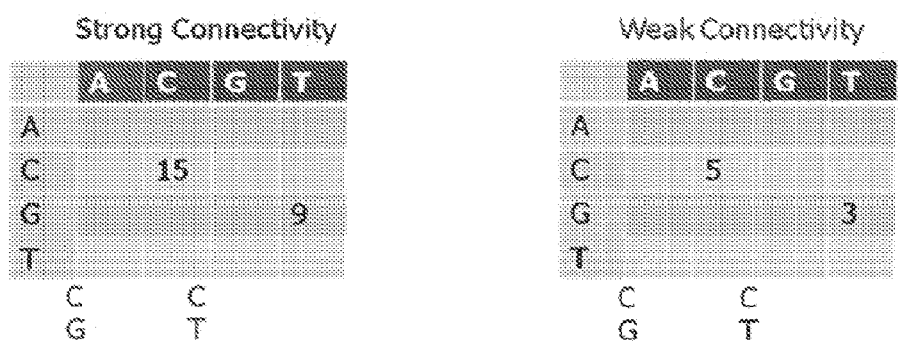
FIG. 17 shows an example of a method of decreasing the number of false negatives in which a confident heterozygous SNP call could be made despite a small number of reads.

Another of the major advantages of the MT process is the ability to dramatically increase the accuracy of heterozygous SNP calling. FIG. 16 shows two examples of error detection resulting from the use of the MT process. The first example is shown in FIG. 16 (left), in which the connectivity matrix does not support any of the expected hypotheses. This is an indication that one of the heterozygous SNPs is not really a heterozygous SNP. In this example, the A/C heterozygous SNP is in reality a homozygous locus (A/A), which was mislabeled as a heterozygous locus by the assembler. This error can be identified, and either eliminated or (in this case) corrected. The second example is shown in FIG. 17 (right), in which the connectivity matrix for this case supports both hypotheses at the same time. This is a sign that the heterozygous SNP calls are not real.

A "healthy" heterozygous SNP-connection matrix is one that has only two high cells (at the expected heterozygous SNP positions, i.e., not on a straight line). All other possibilities point to potential problems, and can be either eliminated, or used to make alternate basecalls for the loci of interest.

Another advantage of the MT process is the ability to call heterozygous SNPs with weak supports (e.g., where it was hard to map DNBs due to the bias or mismatch rate). Since the MT process requires an extra constraint on the heterozygous SNPs, one could reduce the threshold that a heterozygous SNP call requires in a non-MT assembler. FIG. 17 demonstrates an example of this case in which a confident heterozygous SNP call could be made despite a small number of reads. In FIG. 17 (right) under a normal scenario the low number of supporting reads would have prevented any assembler to confidently call the corresponding heterozygous SNPs. However, since the connectivity matrix is "clean," one could more confidently assign heterozygous SNP calls to these loci.

Annotating SNPs in Splice Sites

Introns in transcribed RNAs need to be spliced out before they become mRNA. Information for splicing is embedded within the sequence of these RNAs, and is consensus based. Mutations in splicing site consensus sequence are causes to many human diseases (Faustino and Cooper, Genes Dev. 17:419-437, 2011). The majority of splice sites conform to a simple consensus at fixed positions around an exon. In this regard, a program was developed to annotate Splice Site mutations. In this program, consensus splice position models was used (accessible from the College of Computer, Mathematical and Natural Sciences website, per Steve Mount). A look-up is performed for a pattern: CAG|G in the 5'-end region of an exon ("|" denotes the beginning of exon), and MAG|GTRAG in the 3'-end region of the same exon ("|" denotes the ending of exon). Here M={A,C}, R={A,G}. Further, splicing consensus positions are classified into two types: type I, where consensus to the model is 100% required; and type II, where consensus to the model is preserved in >50% cases. Presumably, a SNP mutation in a type I position will cause the splicing to miss, whereas a SNP in a type II position will only decrease the efficiency of the splicing event.

The program logic for annotating splice site mutations comprises two parts. In part I, a file containing model positions sequences from the input reference genome is generated. In part 2, the SNPs from a sequencing project are compared to these model positions sequences and report any type I and type II mutations. The program logic is exon-centric instead of intron-centric (for convenience in parsing the genome). For a given exon, in its 5'-end we look for the consensus "cAGg" (for positions −3, −2, −1, 0, 0 means the start of exon). Capital letters means type I positions, and lower-case letters means type II positions). In the 3'-end of the exon, a look-up is performed for the consensus "magGTrag" (for position sequence −3, −2, −1, 0, 1, 2, 3, 4). Exons from the genome release that do not confirm to these requirements are simply ignored (~5% of all cases). These exons fall into other minor classes of splice-site consensus and are not investigated by the program logic. Any SNP from the genome sequenced is compared to the model sequence at these genomic positions. Any mismatch in type I will be reported. Mismatch in type II positions are reported if the mutation departs from the consensus.

The above program logic detects the majority of bad splice-site mutations. The bad SNPs that are reported are definitely problematic. But there are many other bad SNPs causing splicing problem that are not detected by this program. For example, there are many introns within the human genome that do not confirm to the above-mentioned consensus. Also, mutations in bifurcation points in the middle of the intron may also cause splice problem. These splice-site mutations are not reported.

Annotation of SNPs Affecting Transcription Factor Binding Sites (TFBS).

JASPAR models are used for finding TFBSs from the released human genome sequences (either build 36 or build 37). JASPAR Core is a collection of 130 TFBS positional frequency data for vertebrates, modeled as matrices (Bryne et al., Nucl. Acids Res. 36:D102-D106, 2008; Sandelin at al., Nucl. Acids Res. 23:D91-Dg4, 2004). These models are downloaded from the JASPAR website (jaspar.genereg.net/cgi-bin/jaspar_db.pl?rm=browse&db=core&tax_group=vertebrates). (These models are converted into Position Weight Matrices (PWMs) using the following formula: $wi = \log 2 [(fi+p\ Ni^{1/2})/(Ni+Ni^{1/2})/p]$, where: fi is the observed frequency for the specific base at position I; Ni is the total observations at the position; and p the background frequency for the current nucleotide, which is defaulted to 0.25 (Wasserman and Sandelin, Nature Reviews, Genetics 5:P276-287, 2004). A specific program, mast (meme.sd-sc.edu/meme/mast-intro.html), is used to search sequence segments within the genome for TFBS-sites. A program was run to extract TFBS-sites in the reference genome. The outline of steps is as follows: (i) For each gene with mRNA, extract [−5000, 1000] putative TFBS-containing regions from the genome, with 0 being the mRNA starting location. (ii) Run mast-search of all PWM-models for the putative TFBS-containing sequences. (iii) Select those hits above a given threshold. (iv) For regions with multiple or overlapping hits, select only 1-hit, the one with the highest mast-search score.

With the TFBS model-hits from the reference genome generated and/or stored in suitable computer-readable medium, a computing device or computer logic thereof can identify SNPs which are located within the hit-region. These SNPs will impact on the model, and a change in the hit-score. A second program was written to compute such changes In the hit-score, as the segment containing the SNP is run twice into the PWM model, once for the reference, and the second time for the one with the SNP substitution. A SNP causing the segment hit score to drop more than 3 is identified as a bad SNP.

Selection of genes with two bad SNPs. Genes with bad SNPs are classified into two categories: (1) those affecting the AA-sequence transcribed; and (2) those affecting the transcription binding site. For AA-sequence affecting, the following SNP subcategories are included:

(1) Nonsense or Nonstop Variations.

These mutations either cause a truncated protein or an extended protein. In either situation, the function of the protein product is either completely lost or less efficient.

(2) Splice Site Variations.

These mutations cause either the splice site for an intron to be destroyed (for those positions required to be 100% of a certain nucleotide by the model) or severely diminished (for those sites required to be >50% for a certain nucleotide by the model. The SNP causes the splice-site nucleotide to mutate to another nucleotide that is below 50% of consensus as predicted by the splice-site consensus sequence model). These mutations will likely produce proteins which are truncated, missing exons, or severely diminishing in protein product quantity.

(3) Polyphen2 Annotation of AA Variations.

For SNPs that cause change In amino-acid sequence of a protein, but not its length, Polyphen2 (Adzhubei et al., Nat. Methods 7:248-249, 2010) was used as the main annotation tool. Polyphen2 annotates the SNP with "benign", "unknown, "possibly damaging", and "probably damaging". Both "possibly damaging" and "probably damaging" were identified as bad SNPs. These category assignments by Polyphen2 are based on structural predictions of the Polyphen2 software.

For transcription-binding site mutations the 75% of maxScore of the models was used based on the reference genome as a screening for TFBS-binding sites. Any model-hit in the region that is <=75% of maxScore are removed. For those remaining, if a SNP causes the hit-score to drop 3 or more, it is considered as a detrimental SNP.

Two classes of genes are reported. Class 1 genes are those that had at least 2-bad AA-affecting mutations. These mutations can be all on a single allele (Class 1.1), or spread on 2 distinct alleles (Class 1.2). Class 2 genes are a superset of the Class 1 set. Class 2 genes are genes contain at least 2-bad SNPs, Irrespective it is AA-affecting or TFBS-site affecting. But a requirement is that at least 1 SNP is AA-affecting. Class 2 genes are those either in Class 1, or those that have 1 detrimental AA-mutation and 1 or more detrimental TFBS-affecting variations. Class 2.1 means that all these detrimental mutations are from a single allele, whereas Class 2.2 means that detrimental SNPs are coming from two distinct alleles.

The foregoing techniques and algorithms are applicable to methods for sequencing complex nucleic acids, optionally in conjunction with MT processing prior to sequencing (MT in combination with sequencing may be referred to as "MT sequencing"), which are described in detail as follows. Such methods for sequencing complex nucleic acids may be performed by one or more computing devices that execute computer logic. An example of such logic is software code written in any suitable programming language such as Java, C++, Perl, Python, and any other suitable conventional and/or object-oriented programming language. When executed in the form of one or more computer processes, such logic may read, write, and/or otherwise process structured and unstructured data that may be stored in various structures on persistent storage and/or in volatile memory; examples of such storage structures include, without limitation, files, tables, database records, arrays, lists, vectors, variables, memory and/or processor registers, persistent and/or memory data objects instantiated from object-oriented classes, and any other suitable data structures.

Improving Accuracy in Long-Read Sequencing

In DNA sequencing using certain long-read technologies (e.g., nanopore sequencing), long (e.g., 10-100 kb) read lengths are available but generally have high false negative and false positive rates. The final accuracy of sequence from such long-read technologies can be significantly enhanced using haplotype information (complete or partial phasing) according to the following general process.

First, a computing device or computer logic thereof aligns reads to each other. A large number of heterozygous calls are expected to exist in the overlap. For example, if two to five 100 kb fragments overlap by a minimum of 10%, this results in >10 kb overlap, which could roughly translate to 10 heterozygous loci. Alternatively, each long read is aligned to a reference genome, by which a multiple alignment of the reads would be implicitly obtained.

Once the multiple read alignments have been achieved, the overlap region can be considered. The fact that the overlap could include a large number (e.g., N=10) of het loci can be leveraged to consider combinations of hats. This combinatorial modality results in a large space ($4^N$ or $4\hat{}N$; if N=10, then $4^N=\sim 1$ million) of possibilities for the haplotypes. Of all of these $4^N$ points in the N-dimensional space, only two points are expected to contain biologically viable information, i.e., those corresponding to the two haplotypes. In other words, there is a noise suppression ratio of $4^N/2$ (here $10^6/2$ or ~500,000). In reality, much of this $4^N$ space is degenerate, particularly since the sequences are already aligned (and therefore look alike), and also because each locus does not usually carry more than two possible bases (if it is a real het). Consequently, a lower bound for this space is actually $2^N$ (if N=10, then $2^N=\sim 1000$). Therefore, the noise suppression ratio could only be $2^N/2$ (here 1000/2=500), which is still quite impressive. As the number of the false positives and false negatives grow, the size of the space expands from $2^N$ to $4^N$, which in turn results in a higher noise suppression ratio. In other words, as the noise grows, it will automatically be more suppressed. Therefore, the output products are expected to retain only a very small (and rather constant) amount of noise, almost independently from the input noise. (The tradeoff is the yield loss in the noisier conditions.) Of course, these suppression ratios are altered if (1) the errors are systematic (or other data idiosyncrasies), (2) the algorithms are not optimal. (3) the overlapping sections are shorter, or (4) the coverage redundancy is less. N is any integer greater than one, such as 2, 3, 5, 10, or more.

The following methodology is useful for increasing the accuracy of the long-read sequencing methods, which could have a large initial error rate.

First, a computing device or computer logic thereof aligns a few reads, for instance 5 reads. Assuming reads are ~100 kb, and the shared overlap is 10%, this results in a 10 kb overlap in the 5 reads or more, such as 10-20 reads. Also assume there is a het In every 1 Kb. Therefore, there would be a total of 10 hets in this common region.

Next, the computing device or computer logic thereof fills in in a portion (e.g., just non-zero elements) or the whole matrix of $alpha^{10}$ possibilities (where alpha is between 2 and 4) for the above 10 candidate hets. In one implementation only 2 out of $alpha^{10}$ cells of this matrix is high density (e.g., as measured by a threshold, which can be predetermined or dynamic). These are the cells that correspond to the real hets. These two cells can be considered substantially noise-free centers. The rest will contain mostly 0 and occasionally 1 memberships, especially if the errors are not systematic. If the errors are systematic, there may be a clustering event (e.g., a third cell that has more than just 0 or 1), which makes the task more difficult. However, even in this case, the cluster membership for the false cluster should be significantly weaker (e.g., as measured by an absolute or relative amount) than that of the two expected clusters. The trade-off in this case is that the starting point would include more multiple sequences aligned, which relates directly to having longer reads or larger coverage redundancy.

The above step assume that the two viable clusters are observed among the overlapped reads. For a large number of false positives, this would not be the case. If this is the case, in the alpha-dimensional space, the expected two clusters will be blurred, i.e., instead of being single points with high density, they will be blurred clusters of M points around the cells of interest, where these cells of interest are the noise-free centers that are at the center of the cluster. This enables the clustering methods to capture the locality of the expected points, despite the fact that the exact sequence is not represented in each read. A cluster event may also occur when the clusters are blurred (i.e. there could be more than two centers), but in a similar manner as described above, a score (e.g., the total counts for the cells of a cluster) can be used to distinguish a weaker cluster from the two real clusters, for a diploid organism. The two real clusters can be used to create contigs, as described herein, for various regions, and the contigs can be matched into two groups to form haplotypes for a large region of the complex nucleic acid.

Finally, the computing device or computer logic thereof the population-based (known) haplotypes can be used to increase confidence and/or to provide extra guidance in finding the actual clusters. A way to enable this method is to provide each observed haplotype a weight, and to provide a smaller but non-zero value to the unobserved haplotypes. By doing so, one achieves a bias toward the natural haplotypes that have been observed in the population of interest.

Converting Long Reads to Virtual MT

The algorithms that are designed for MT (including the phasing algorithm) can be used for long reads by assigning a random virtual tag (with uniform distribution) to each of the long fragments. The virtual tag has the benefit of enabling a true uniform distribution for each code. MT cannot achieve this level of uniformity due to the difference In the pooling of the codes and the difference in the decoding efficiency of the codes. A ratio of 3:1 (and up to 10:1) can be easily observed in the representation of any two codes in MT. However, the virtual MT process results in a true 1:1 ratio between any two codes.

In view of the foregoing description, according to one aspect of the invention, methods are provided for determining a sequence of a complex nucleic acid (for example, a whole genome) of one or more organisms, that is, an individual organism or a population of organisms. Such methods comprise: (a) receiving at one or more computing devices a plurality of reads of the complex nucleic acid; and (b) producing, with the computing devices, an assembled sequence of the complex nucleic acid from the reads, the assembled sequence comprising less than 1.0, 0.8, 0.7, 0.6, 0.5, 0.4, 0.3, 0.2, 0.1, 0.08, 0.07, 0.06, 0.05 or 0.04 false single nucleotide variant per megabase at a call rate of 70, 75, 80, 85, 90 or 95 percent or greater, wherein the methods are performed by one or more computing devices. In some aspects, a computer-readable non-transitory storage medium stores one or more sequences of instructions that comprise instructions which, when executed by one or more computing devices, cause the one or more computing devices to perform the steps of such methods.

According to one embodiment, in which such methods involve haplotype phasing, the method further comprises identifying a plurality of sequence variants in the assembled sequence and phasing the sequence variants (e.g., 70, 75, 80, 85, 90, 95 percent or more of the sequence variants) to produce a phased sequence, i.e., a sequence wherein sequence variants are phased. Such phasing information can be used in the context of error correction. For example, according to one embodiment, such methods comprise identifying as an error a sequence variant that is inconsistent with the phasing of at least two (or three or more) phased sequence variants.

According to another such embodiment, in such methods the step of receiving the plurality of reads of the complex nucleic acid comprises a computing device and/or a computer logic thereof receiving a plurality of reads from each of a plurality of long fragments of the complex nucleic acid. Information regarding such fragments is useful for correcting errors or for calling a base that otherwise would have been a "no call." According to one such embodiment, such methods comprise a computing device and/or a computer logic thereof calling a base at a position of said assembled sequence on the basis of preliminary base calls for the position from two or more long fragments. For example, methods may comprise calling a base at a position of said assembled sequence on the basis of preliminary base calls from at least two, at least three at least four or more than four long fragments. In some embodiments, such methods may comprise identifying a base call as true if it is present at least two, at least three, at least four long fragments or more than four long fragments. In some embodiments, such methods may comprise identifying a base call as true if it is present at least a majority (or at least 60%, at least 75%, or at least 80%) of the fragments for which a preliminary base call is made for that position in the assembled sequence. According to another such embodiment, such methods comprise a computing device and/or a computer logic thereof identifying a base call as true if it is present three or more times in reads from two or more long fragments.

According to another such embodiment, the long fragment from which the reads originate is determined by identifying a tag (or unique pattern of tags) that is associated with the fragment. Such tags optionally comprise an error-correction or error-detection code (e.g., a Reed-Solomon error correction code). According to one embodiment of the invention, upon sequencing a fragment and tag, the resulting read comprises tag sequence data and fragment sequence data.

According to another embodiment, such methods further comprise: a computing device and/or a computer logic thereof providing a first phased sequence of a region of the complex nucleic acid in the region comprising a short tandem repeat; a computing device and/or a computer logic thereof comparing reads (e.g., regular or mate-pair reads) of the first phased sequence of the region with reads of a second phased sequence of the region (e.g., using sequence coverage); and a computing device and/or a computer logic thereof identifying an expansion of the short tandem repeat in one of the first phased sequence or the second phased sequence based on the comparison.

According to another embodiment, the method further comprises a computing device and/or a computer logic thereof obtaining genotype data from at least one parent of the organism and producing an assembled sequence of the complex nucleic acid from the reads and the genotype data.

According to another embodiment, the method further comprises a computing device and/or a computer logic thereof performing steps that comprise: aligning a plurality of the reads for a first region of the complex nucleic acid, thereby creating an overlap between the aligned reads; identifying N candidate hets within the overlap; clustering the space of $2^N$ to $4^N$ possibilities or a selected subspace thereof, thereby creating a plurality of clusters; Identifying two clusters with the highest density, each identified cluster comprising a substantially noise-free center, and repeating the foregoing steps for one or more additional regions of the complex nucleic acid.

According to another embodiment, such methods further comprise providing an amount of the complex nucleic acid, and sequencing the complex nucleic acid to produce the reads.

According to another embodiment, in such methods the complex nucleic acid is selected from the group consisting of a genome, an exome, a transcriptome, a methylome, a mixture of genomes of different organisms, and a mixture of genomes of different cell types of an organism.

According to another aspect of the invention, an assembled human genome sequence is provided that is produced by any of the foregoing methods. For example, one or more computer-readable non-transitory storage media stores an assembled human genome sequence that is produced by any of the foregoing methods. According to another aspect, a computer-readable non-transitory storage medium stores one or more sequences of instructions that comprise instructions which, when executed by one or more computing devices, cause the one or more computing devices to perform any, some, or all of the foregoing methods.

According to another aspect of the invention, methods are provided for determining a whole human genome sequence, such methods comprising: (a) receiving, at one or more computing devices, a plurality of reads of the genome; and (b) producing, with the one or more computing devices, an assembled sequence of the genome from the reads comprising less than 600 false heterozygous single nucleotide variants per gigabase at a genome call rate of 70% or greater. According to one embodiment, the assembled sequence of the genome has a genome call rate of 70% or more and an exome call rate of 70% or greater. In some aspects, a computer-readable non-transitory storage medium stores one or more sequences of instructions that comprise instructions which, when executed by one or more computing devices, cause the one or more computing devices to perform any of the methods of the invention described herein.

According to another aspect of the invention, methods are provided for determining a whole human genome sequence, such methods comprising: (a) receiving, at one or more computing devices, a plurality of reads from each of a plurality of long fragments, each long fragment comprising one or more fragments of the genome; and (b) producing, with the one or more computing devices, a phased, assembled sequence of the genome from the reads that comprises less than 1000 false single nucleotide variants per gigabase at a genome call rate of 70% or greater. In some aspects, a computer-readable non-transitory storage medium stores one or more sequences of instructions that comprise instructions which, when executed by one or more computing devices, cause the one or more computing devices to perform such methods.

Kits

In one aspect the invention provides kits useful for the practice of MT as described herein. Kit contents may include one, two, three or more of the following components:

A. Libraries i) A library of barcodes flanked by transposon ends (i.e., a library of tagged transposons). In some embodiments the transposon ends are inverted terminal repeats. In some embodiments the transposon ends are 9-40 bases In length. In some embodiments the bar codes are 6-20 bases in length. In some embodiments the tagged transposons also comprise amplification primer binding sites (e.g., where most of or the entire library has the same primer binding sites). In some embodiments the tagged transposons comprise at least two amplification primer binding sites. In some embodiments the two amplification primer binding sites hybridize to the same primer sequence. In some embodiments the kit comprises amplification primer(s) that hybridize to primer binding sequences of the tagged transposons.

ii) A library of clonal barcodes comprising a plurality of $10^4$ or more distinct sources of clonal bar codes. In some embodiments the clonal bar codes are tagged transposons as described in (i). In some embodiments the clonal bar codes are immobilized on a carrier or support, such as a polymer, bead, dendrimer or magnetic particle. In some embodiments the sources of clonal bar codes are created by emulsion PCR. In some embodiments the sources of clonal bar codes are created using a mix-and-divide combinatorial synthesis. In some embodiments the clonal barcodes are attached to the support with a linker (e.g., where most of or the entire library has the same linker). In some embodiments, the linker is cleavable such that the barcode sequence may be released from the support by treatment with a cleaving agent. In some embodiments the cleaving agent is a restriction endonuclease or nickase.

iii) A library of concatamers comprising monomers, wherein the monomers comprise bar codes. In some embodiments the monomers comprise primer binding sites and/or transposon end sequences and/or restriction endonuclease recognition sites (e.g., where most of or the entire library shares the same sites or sequences). In some embodiments the monomers comprise tagged transposons as described in (i).

iv) A library of templates suitable for rolling circle amplification, wherein the templates comprise a monomer as described in (iii). In some embodiments the kit contains a an enzyme (e.g., phi29 polymerase) suitable for converting the templates into concatemers.

v) A library of hairpin or stem-loop oligonucleotides, wherein the library comprises a plurality of at least about $10^4$ barcodes, each oligonucleotide comprising two copies of a barcode sequence (which may be in the loop portion of the oligonucleotide). In some embodiments each oligonucleotide comprises two amplification primer binding sites positioned between the copies of barcode sequence. In some embodiments oligonucleotides comprise random or semi random sequences at the 5' and 3' termini. In some embodiments the sequences are 3-8 bases in length or 3-5 bases in length.

In some embodiments, libraries (i)-(v) comprise at least about $10^4$, at least about $10^6$, at least about $10^6$, or at least about $10^7$ different barcodes. In some embodiments, libraries (i)-(iv) comprise at least about $10^4$, at least about $10^6$, at least about $10^6$, or at least about $10^7$ different sources of clonal barcodes.

B. Enzymes i) Transposase, e.g., a transposase that acts on the library of barcodes;

ii) DNA polymerase (e.g., DNA polymerase I, Klenow fragment, Taq I);

iii) phi29 polymerase;

iv) Exonuclease (e.g., Exonuclease III);

v) Restriction endonuclease;

vi) DNA ligase;

vii) alkaline phosphatase;

viii) Nicking enzymes;

ix) Endonuclease (e.g., Vvn);

x) Uracil-based or ribo-based DNA cleaving components (e.g., uracil DNA glycosylase).

The kit may also include one or more tubes; a mobility limiting agent (e.g., agarose or PEG), and reagents for isolating high molecular weight DNA from eukaryotic cells. The kit components may be packaged together and the package may contain or be accompanied by printed instructions for using the kit.

Compositions

In one aspect, the invention provides a composition (e.g., a mixture in a single tube or vessel) comprising any of libraries (i)-(v), described above, and genomic DNA as described hereinabove. The genomic DNA may be, for example, from an animal, such as a mammal (e.g., human), a plant, a fungus. The composition may comprise more than one genome equivalent of genomic DNA. In various embodiments the mixture may comprise at least 5 genome equivalents, at least 10 genome equivalents, at least 25 genome equivalents, at least 50 genome equivalents, at least 100 genome equivalents, at least 500 genome equivalents, or at least 1000 genome equivalents, such as from 5-20 genome equivalents, such as from 5-100 genome equivalents, such as from 50-1000 genome equivalents. In some embodiments the genomic DNA comprises only naturally occurring sequences and does not comprise adaptors or linkers. The composition may comprise one or more enzymes independently selected from a transposase, a DNA polymerase, a restriction endonuclease, a DNA ligase and alkaline phosphatase.

While this invention has been disclosed with reference to specific aspects and embodiments, it is apparent that other embodiments and variations of this invention may be devised by others skilled in the art without departing from the true spirit and scope of the invention.

For all purposes in the United States of America, each and every publication and patent document cited in this disclosure is incorporated herein by reference as if each such publication or document was specifically and individually indicated to be incorporated herein by reference. Citation of publications and patent documents is not intended as an indication that any such document is pertinent prior art, nor does it constitute an admission as to its contents or date.

The invention claimed is:

1. A method of producing tagged long fragments comprising target DNA sequences in a homogeneous reaction without the use of physical compartmentalization, the method comprising:
   (a) obtaining a plurality of double-stranded long fragments comprising target DNA sequences;
   (b) inserting multiple copies of a common adaptor sequence into at least some long fragments of the plurality of double-stranded long fragments to produce a plurality of adaptored long fragments that comprise the target DNA sequences and the common adaptor sequence, wherein said inserting comprises nicking on both strands of said at least some long fragments to produce nick sites with free 3' termini, and
   i) introducing gaps at the nick sites and ligating the common adaptor sequence at the free 3' termini, or
   ii) using controlled nick translation (CNT) to translate the nick sites and ligating the common adaptor sequence at 3' termini produced by the CNT;
   (c) combining at least some adaptored long fragments of the plurality of adaptored long fragments in a single mixture with a population of beads under conditions that promote interaction of individual adaptored long fragments with single beads, thereby producing a plurality of individual adaptored long fragments that are each associated with a single bead, wherein
   (i) each bead in the population of beads comprises at least 1000 copies of the same oligonucleotide immobilized thereon, said oligonucleotide comprising a tag-containing sequence and a sequence complementary to the common adaptor sequence,
   (ii) each tag-containing sequence comprises a tag sequence, and
   (iii) the population of beads comprises, in aggregate, at least 100,000 different tag sequences;
   (d) producing tagged long fragments in the single mixture, wherein said producing comprises incorporating into each of a plurality of the individual adaptored long fragments multiple copies of the tag sequence from the single bead with which the individual adaptored long fragment is associated.

2. The method of claim 1 wherein the tag-containing sequence comprises PCR primer binding sites.

3. The method of claim 1 wherein the target DNA sequences comprise genomic DNA sequence from a diploid organism and the plurality of adaptored long fragments in the single mixture comprises more than a haploid amount of genomic DNA from the diploid organism.

4. The method of claim 1 wherein the target DNA sequences comprise bacterial sequences from a mixture of bacterial DNA in a microbiome sample.

5. The method of claim 1 further comprising: (e) producing tagged subfragments of the tagged long fragments, wherein the tagged subfragments of the same tagged long fragment comprise the tag sequence from said same tagged long fragment.

6. The method of claim 5 wherein producing the tagged subfragments in step (e) comprises performing an amplification reaction to produce a plurality of amplicons from the tagged long fragments.

7. The method of claim 5 wherein producing the tagged subfragments in step (e) comprises annealing the oligonucleotides immobilized on each bead comprising the tag-containing sequence to the common adaptor sequence, and extending the oligonucleotides to form the tagged subfragments.

8. The method of claim 5 comprising the steps of:
   sequencing the tagged subfragments to produce a plurality of informative sequence reads, wherein said informative sequence reads include sequence of the target DNA sequences and at least one tag sequence;
   combining informative sequence reads from the plurality of informative sequence reads to produce assembled sequence(s) of the target DNA sequences, wherein the combining comprises determining that informative sequence reads comprising the same tag sequence originated from tagged subfragments produced from the same tagged long fragment.

9. The method of claim 1 wherein the target DNA sequences comprise genomic DNA sequences from an animal.

10. The method of claim 9 wherein the genomic DNA sequences are human genomic DNA sequences.

11. The method of claim 1 wherein said inserting comprises nicking on both strands of said at least some long fragments to produce nick sites with free 3' termini, introducing gaps at the nick sites, and ligating the common adaptor sequences at the free 3' termini.

12. The method of claim 11 further comprising: (e) producing tagged subfragments of the tagged long fragments, wherein the tagged subfragments of the same tagged long fragment comprise the tag sequence from said same tagged long fragment.

13. The method of claim 12 wherein producing the tagged subfragments in step (e) comprises performing an amplification reaction to produce a plurality of amplicons from the tagged long fragments.

14. The method of claim 12 wherein producing the tagged subfragments in step (e) comprises annealing the oligonucleotides immobilized on each bead comprising the tag-containing sequence to the common adaptor sequence, and extending the oligonucleotides to form the tagged subfragments.

15. The method of claim 12 comprising the steps of sequencing the tagged subfragments to produce a plurality of informative sequence reads, wherein said informative sequence reads include sequence of the target DNA sequences and at least one tag sequence;
   combining informative sequence reads from the plurality of informative sequence reads to produce assembled sequence(s) of the target DNA sequences, wherein the combining comprises determining that informative sequence reads comprising the same tag sequence originated from tagged subfragments produced from the same tagged long fragment.

16. The method of claim 11 wherein the target DNA sequences comprise genomic DNA sequences from an animal.

17. The method of claim 16 wherein the genomic DNA sequences are human genomic DNA sequences.

18. The method of claim 1, wherein said inserting comprises nicking on both strands of said at least some long fragments to produce nick sites with free 3' termini and using CNT to translate the nicks and ligating the common adaptor sequence at the free 3' termini produced by CNT.

19. The method of claim 18 further comprising: (e) producing tagged subfragments of the tagged long fragments, wherein the tagged subfragments of the same tagged long fragment comprise the tag sequence from said same tagged long fragment.

20. The method of claim 19 wherein producing the tagged subfragments in step (e) comprises performing an amplification reaction to produce a plurality of amplicons from the tagged long fragments.

21. The method of claim 19 wherein producing the tagged subfragments in step (e) comprises annealing the oligonucleotides immobilized on each bead comprising the tag-containing sequence to the common adaptor sequence, and extending the oligonucleotides to form the tagged subfragments.

22. The method of claim 19 comprising the steps of:
   sequencing the tagged subfragments to produce a plurality of informative sequence reads, wherein said informative sequence reads include sequence of the target DNA sequences and at least one tag sequence;
   combining informative sequence reads from the plurality of informative sequence reads to produce assembled sequence(s) of the target DNA sequences, wherein the combining comprises determining that informative sequence reads comprising the same tag sequence originated from tagged subfragments produced from the same tagged long fragment.

23. The method of claim 18 wherein the target DNA sequences comprise genomic DNA sequences from an animal.

24. The method of claim 23 wherein the genomic DNA sequences are human genomic DNA sequences.

\* \* \* \* \*

SEQUENCE LISTING

```
<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 1
ccgcagtagc ttacgaatcg                                               20

<210> SEQ ID NO 2
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 2
gatttaactg agcacttggc                                               20
```